(12) United States Patent
Torii et al.

(10) Patent No.: US 9,044,525 B2
(45) Date of Patent: Jun. 2, 2015

(54) POLYACRYLIC ACID (SALT)-BASED WATER ABSORBENT RESIN POWDER AND METHOD FOR PRODUCING THE SAME

(75) Inventors: Kazushi Torii, Hyogo (JP); Reiko Nakatsuru, Hyogo (JP); Yasuhisa Nakashima, Hyogo (JP); Katsuyuki Wada, Hyogo (JP); Kunihiko Ishizaki, Hyogo (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 0 days.

(21) Appl. No.: 14/129,792
(22) PCT Filed: Jun. 29, 2012
(86) PCT No.: PCT/JP2012/066765
§ 371 (c)(1),
(2), (4) Date: Mar. 10, 2014
(87) PCT Pub. No.: WO2013/002387
PCT Pub. Date: Jan. 3, 2013

(65) Prior Publication Data
US 2014/0193641 A1    Jul. 10, 2014

(30) Foreign Application Priority Data
Jun. 29, 2011 (JP) .................................. 2011-145006

(51) Int. Cl.
*A61L 15/26* (2006.01)
*A61L 15/60* (2006.01)
(Continued)

(52) U.S. Cl.
CPC ............ *A61L 15/26* (2013.01); *Y10T 428/2982* (2015.01); *C08F 20/06* (2013.01);
(Continued)

(58) Field of Classification Search
CPC ......... A61L 15/26; A61L 15/60; C08F 20/06; C08J 233/02; C08J 3/245
USPC ............ 428/402; 252/194; 525/451; 524/556
See application file for complete search history.

(56) References Cited

U.S. PATENT DOCUMENTS

| 4,703,067 A | 10/1987 | Mikita et al. |
| 5,002,986 A | 3/1991 | Fujiura et al. |

(Continued)

FOREIGN PATENT DOCUMENTS

| CN | 1610707 A | 4/2005 |
| EP | 450922 A2 | 10/1991 |

(Continued)

OTHER PUBLICATIONS

International Preliminary Report on Patentability for PCT/JP2012/066765 dated Jan. 16, 2014, and English translation thereof.
(Continued)

*Primary Examiner* — Michael M Bernshteyn
(74) *Attorney, Agent, or Firm* — Roylance, Abrams, Berdo & Goodman, L.L.P.

(57) ABSTRACT

Provided is a water absorbent resin having excellent liquid permeability, water absorbent speed, anti-impact stability, and weather resistance. Provided is a polyacrylic acid (salt)-based water absorbent resin powder in which the water absorption capacity without load (CRC) is 30 to 45 [g/g], the water absorption capacity under load (AAP 0.3) is 20 to 35 [g/g], the water absorption capacity under load (AAP 0.7) is 10 to 28 [g/g], and the weight average particle diameter (D50) is 300 to 500 μm, characterized by including p-methoxyphenol; having a degradable soluble component (0.05% L-A (saline) for 2 hours/60° C., one hour extraction rinse/room temperature) of 40% by weight or less; and having a internal gas bubbles ratio of 0.1 to 2.5%, as specified by the following equation.

(Internal gas bubbles ratio)[%]={(True density)−(Apparent density)}/(True density)×100

20 Claims, 2 Drawing Sheets

(51) Int. Cl.
  *C08F 20/06* (2006.01)
  *C08J 3/24* (2006.01)
  *C08K 5/00* (2006.01)
  *C08L 33/02* (2006.01)
  *C08K 5/17* (2006.01)

(52) U.S. Cl.
  CPC ............. *C08J 2333/02* (2013.01); *C08L 33/02* (2013.01); *C08J 3/245* (2013.01); *C08K 5/0091* (2013.01); *C08K 5/175* (2013.01); *A61L 15/60* (2013.01)

(56) References Cited

U.S. PATENT DOCUMENTS

| | | | |
|---|---|---|---|
| 5,118,719 | A | 6/1992 | Lind |
| 5,124,188 | A | 6/1992 | Roe et al. |
| 5,154,713 | A | 10/1992 | Lind |
| 5,314,420 | A | 5/1994 | Smith et al. |
| 5,399,591 | A | 3/1995 | Smith et al. |
| 5,451,613 | A | 9/1995 | Smith et al. |
| 5,462,972 | A | 10/1995 | Smith et al. |
| 5,562,646 | A | 10/1996 | Goldman et al. |
| 5,624,967 | A | 4/1997 | Hitomi et al. |
| 5,712,316 | A | 1/1998 | Dahmen et al. |
| 5,856,370 | A | 1/1999 | Chmelir |
| 5,985,944 | A | 11/1999 | Ishizaki et al. |
| 6,107,358 | A | 8/2000 | Harada et al. |
| 6,136,873 | A | 10/2000 | Hahnle et al. |
| 6,291,636 | B1 | 9/2001 | Miyake et al. |
| 6,414,214 | B1 | 7/2002 | Engelhardt et al. |
| 6,562,879 | B1 | 5/2003 | Hatsuda et al. |
| 6,576,713 | B2 | 6/2003 | Ishizaki et al. |
| 6,641,064 | B1 | 11/2003 | Dentler et al. |
| 6,750,262 | B1 | 6/2004 | Hahnle et al. |
| 6,817,557 | B2 | 11/2004 | Kakita et al. |
| 6,849,665 | B2 | 2/2005 | Frenz et al. |
| 6,939,914 | B2 | 9/2005 | Qin et al. |
| 7,169,843 | B2 | 1/2007 | Smith et al. |
| 7,173,086 | B2 | 2/2007 | Smith et al. |
| 2002/0128618 | A1 | 9/2002 | Frenz et al. |
| 2004/0110914 | A1* | 6/2004 | Nakahara et al. .......... 526/317.1 |
| 2005/0063313 | A1 | 3/2005 | Nanavati et al. |
| 2005/0176834 | A1 | 8/2005 | Hintz et al. |
| 2005/0245684 | A1 | 11/2005 | Daniel et al. |
| 2005/0256469 | A1 | 11/2005 | Qin et al. |
| 2007/0014338 | A1 | 1/2007 | Ozluturk et al. |
| 2007/0015860 | A1 | 1/2007 | Frank |
| 2007/0293617 | A1 | 12/2007 | Riegel et al. |
| 2008/0125533 | A1 | 5/2008 | Riegel et al. |
| 2008/0202987 | A1 | 8/2008 | Weismantel et al. |
| 2008/0287631 | A1 | 11/2008 | Nitschke |
| 2010/0041550 | A1 | 2/2010 | Riegel et al. |
| 2010/0042612 | A1 | 2/2010 | Gomaa |
| 2010/0268181 | A1 | 10/2010 | Ziemer et al. |
| 2012/0258851 | A1 | 10/2012 | Nakatsuru et al. |
| 2013/0026412 | A1 | 1/2013 | Machida et al. |

FOREIGN PATENT DOCUMENTS

| | | | |
|---|---|---|---|
| EP | 595803 | B1 | 2/2002 |
| EP | 1521601 | B1 | 5/2008 |
| JP | 11349687 | A | 12/1999 |
| JP | 2003246810 | A | 9/2003 |
| WO | 9115362 | A1 | 10/1991 |
| WO | 9422502 | A1 | 10/1994 |
| WO | 9502002 | A1 | 1/1995 |
| WO | 9717397 | A1 | 5/1997 |
| WO | 0052087 | A1 | 9/2000 |
| WO | 2006082189 | A1 | 8/2006 |
| WO | 2006082197 | A1 | 8/2006 |
| WO | 2008025652 | A1 | 3/2008 |
| WO | 2008025655 | A2 | 3/2008 |
| WO | 2008025656 | A1 | 3/2008 |
| WO | 2011040530 | A1 | 4/2011 |
| WO | 2011078298 | A1 | 6/2011 |
| WO | WO 2011078298 | A1 * | 6/2011 |
| WO | 2011126079 | A1 | 10/2011 |

OTHER PUBLICATIONS

Wiley-VCH, "Modern Superabsorbent Polymer Technology", pp. 197-199.
International Search Report for PCT/JP2012/066765 dated Oct. 2, 2012.
Chinese Office Action, dated Mar. 11, 2015, issued for CN Appln. No. 201280032337.X, and its English translation.
Extended European Search Report, dated Mar. 4, 2015, issued in related EP Application No. 12804802.2.
Chinese Office Action, dated Jul. 11, 2014, issued for CN Appln. No. 201280032337.X, and its English translation.

* cited by examiner

US 9,044,525 B2

POLYACRYLIC ACID (SALT)-BASED WATER ABSORBENT RESIN POWDER AND METHOD FOR PRODUCING THE SAME

TECHNICAL FIELD

The present invention relates to a polyacrylic acid (salt)-based water absorbent resin powder and a method for producing the same. More particularly, the present invention relates to a water absorbent resin powder exhibiting an excellent water absorbing property in a paper diaper, and specifically a polyacrylic acid (salt)-based water absorbent resin powder which exhibits high water absorbing performance (in particular, high water absorbent speed) and is excellent in terms of coloration, residual monomers, impact resistance, powder carriability, resistance to urine, and resistance to light, and a method for producing the same.

BACKGROUND ART

Water absorbent resin (SAP/Super Absorbent Polymer) is a water-swellable water-insoluble polymer gelling agent. The water absorbent resin is widely used, mainly disposable use, for absorbing articles such as a paper diaper and sanitary napkin, and further for an agriculture/horticulture water retaining agent, an industrial waterproofing agent, and the like. For such water absorbent resin, many monomers and hydrophilic polymers have been proposed as raw materials. Especially, polyacrylic acid (salt)-based water absorbent resin in which acrylic acid and/or its salt is used as its monomer is used most popularly in industries because of its high water absorbing ability (Non-Patent Literature 1).

The water absorbent resin is produced via a polymerizing step, a drying step, and if necessary a non-dried matter removing step, a pulverizing step, a classification step, a surface crosslinking step, or the like (Patent Literatures 1 to 5, and 50). Meanwhile, the water absorbent resin is required to have many functions (properties) in order to cope with functional sophistication of paper diapers which are one major application of the water absorbent resin. More specifically, the water absorbent resin is required to satisfy many properties such as, not only a high water absorption capacity, but also gel strength, water soluble component, a water absorbent speed, a water absorption capacity under load, liquid permeability, particle size distribution, an anti-urine property, an antimicrobial property, impact resistance (an anti-damaging property), powder fluidity, a deodorant property, anti-coloration (degree of whiteness), low dustiness, and the like. Therefore, many crosslinking techniques, additives, modifications in steps in the production, and the like have been proposed.

Among those properties, the liquid permeability is considered as a more important factor in association with a recent increase (for example, 50% by weight or more) in an amount of the water absorbent resin used in paper diapers. Furthermore, methods and techniques for improving liquid permeability against pressure and liquid permeability without load, such as SFC (Saline Flow Conductivity, see Patent Literature 6) or GBP (Gel Bed Permeability, see Patent Literatures 7 to 9), have been proposed.

Various combinations of a plurality of parameters (including the liquid permeability) of the properties have been also proposed. There have been known a technique for defining impact resistance (FI) (Patent Literature 10), a technique for defining a water absorbent speed or the like (FSR/Vortex) (Patent Literature 11), and a technique for defining the product of liquid diffusivity (SFC) and core absorption quantity after 60 minutes (DA60) (Patent Literature 12).

As the method for improving the liquid permeability such as SFC and GBP, there have been known a technique for adding plaster before or during polymerization (Patent Literature 13), a technique for adding spacers (Patent Literature 14), a technique for using a nitrogen-containing polymer having 5 to 17 [mol/kg] of nitrogen atoms which can be protonated (Patent Literature 15), a technique for using polyamine and polyvalent metal ions or polyvalent anions (Patent Literature 16), a technique for covering, with polyamine, water absorbent resin having a pH of less than 6 (Patent Literature 17), and a technique for using polyammonium carbonate (Patent Literature 18). In addition, there have been known a technique for using polyamine having water soluble component of not less than 3%, and a technique for defining a suction index (WI) or gel strength (Patent Literatures 19 to 21). There have been also known techniques for using polyvalent metal salt while controlling, during polymerization, methoxyphenol that is a polymerization inhibitor, in order to improve coloration and the liquid permeability (Patent Literatures 22 and 23). Moreover, there has been known a technique for polishing particles so as to attain a high bulk specific gravity (Patent Literature 24).

Moreover, in addition to the liquid permeability, the water absorbent speed is also a significant basic property of the water absorbent resin. As one method for improving the water absorbent speed, a technique to increase a specific surface area in order to attain a greater water absorbent speed has been known. More specifically, a technique for controlling to attain fine particle diameter (Patent Literature 25), techniques for granulating fine particles with a large surface area (Patent Literatures 26 to 28), a technique for freeze-drying a hydrogel to cause the hydrogel to be porous (Patent Literature 29), techniques for performing granulation and surface crosslinking of particles simultaneously (Patent Literatures 30 to 32), techniques for foaming polymerization (Patent Literatures 33 to 48), techniques for post-polymerization foaming and crosslinking (Patent Literature 49), and the like have been proposed.

More specifically, as to the foaming polymerization, the following techniques have been known regarding a foaming agent for treating a monomer: techniques for using a carbonate (Patent Literatures 33 to 40), techniques for using an organic solvent (Patent Literatures 41 and 42), techniques for using an inert gas (Patent Literatures 43 to 45), techniques for using an azo compound (Patent Literatures 46 and 47), and a technique for using insoluble inorganic powder (Patent Literature 48), and the like. A technique of foaming after polymerization (Patent Literature 49) and, in Patent Literature 50, a technique of controlling particle size distribution of a gel during drying (Patent Literature 50) have also been known. A technique of using a reducing agent in combination with a chelating agent, or the like for lowering residual monomers has also been known (Patent Literature 51).

Further, as an unpublished prior application on the priority date of the present application (Jun. 29, 2011), a technique of controlling internal gas bubbles ratio for improving water absorption is disclosed in Patent Literatures 52 and 53.

CITATION LIST

Patent Literatures

Patent Literature 1: U.S. Pat. No. 6,576,713
Patent Literature 2: U.S. Pat. No. 6,817,557
Patent Literature 3: U.S. Pat. No. 6,291,636
Patent Literature 4: U.S. Pat. No. 6,641,064

Patent Literature 5: U.S. Patent Application Publication No. 2008/0287631
Patent Literature 6: U.S. Pat. No. 5,562,646
Patent Literature 7: U.S. Patent Application Publication No. 2005/0256469
Patent Literature 8: U.S. Pat. No. 7,169,843
Patent Literature 9: U.S. Pat. No. 7,173,086
Patent Literature 10: U.S. Pat. No. 6,414,214
Patent Literature 11: U.S. Pat. No. 6,849,665
Patent Literature 12: U.S. Patent Application Publication No. 2008/125533
Patent Literature 13: U.S. Patent Application Publication No. 2007/293617
Patent Literature 14: U.S. Patent Application Publication No. 2002/0128618
Patent Literature 15: U.S. Patent Application Publication No. 2005/0245684
Patent Literature 16: International Publication No. WO 2006/082197 pamphlet
Patent Literature 17: U.S. Patent Application Publication No. 2008/202987
Patent Literature 18: International Publication No. WO 2006/082189 pamphlet
Patent Literature 19: International Publication No. WO 2008/025652 pamphlet
Patent Literature 20: International Publication No. WO 2008/025656 pamphlet
Patent Literature 21: International Publication No. WO 2008/025655 pamphlet
Patent Literature 22: U.S. Patent Application Publication No. 2010/041550
Patent Literature 23: U.S. Patent Application Publication No. 2010/042612
Patent Literature 24: U.S. Pat. No. 6,562,879
Patent Literature 25: U.S. Patent Application Publication No. 2007/015860
Patent Literature 26: U.S. Pat. No. 5,624,967
Patent Literature 27: U.S. Patent Application Publication No. 2007/015860
Patent Literature 28: U.S. Pat. No. 5,002,986
Patent Literature 29: U.S. Pat. No. 6,939,914
Patent Literature 30: U.S. Pat. No. 5,124,188
Patent Literature 31: EP No. 0595803
Patent Literature 32: EP No. 0450922
Patent Literature 33: U.S. Pat. No. 5,118,719
Patent Literature 34: U.S. Pat. No. 5,154,713
Patent Literature 35: U.S. Pat. No. 5,314,420
Patent Literature 36: U.S. Pat. No. 5,399,591
Patent Literature 37: U.S. Pat. No. 5,451,613
Patent Literature 38: U.S. Pat. No. 5,462,972
Patent Literature 39: International Publication No. WO 95/02002 pamphlet
Patent Literature 40: U.S. Patent Application Publication No. 2005/063313
Patent Literature 41: International Publication No. WO 94/022502 pamphlet
Patent Literature 42: U.S. Pat. No. 4,703,067
Patent Literature 43: International Publication No. WO 97/017397 pamphlet
Patent Literature 44: International Publication No. WO 00/052087 pamphlet
Patent Literature 45: U.S. Pat. No. 6,107,358
Patent Literature 46: U.S. Pat. No. 5,856,370
Patent Literature 47: U.S. Pat. No. 5,985,944
Patent Literature 48: U.S. Patent Application Publication No. 2010/268181
Patent Literature 49: EP No. 1521601
Patent Literature 50: JP-A No. 11-349687
Patent Literature 51: International Publication No. WO 2011/040530 pamphlet
Patent Literature 52: International Publication No. WO 2011/078298 pamphlet
Patent Literature 53: International Publication No. WO 2011/126079 pamphlet Non-Patent Literatures Non-Patent Literature 1: Modern Superabsorbent Polymer Technology (1998) (particularly, p. 197 to 199)

SUMMARY OF INVENTION

Technical Problem

As described above, in order to improve physical properties of water absorbent resin, many proposals such as surface crosslinking techniques, additives, modifications in steps in the production, and the like have been made. Among these properties, liquid permeability and a water absorbent speed are significant as basic physical properties of the water absorbent resin, and therefore many improvement techniques have been proposed so far.

In this regard, inventors of the present invention filed, as an unpublished prior application on the priority date of the present application, Patent Literature 52 (International Publication No. WO 2011/078298 pamphlet) and Patent Literature 53 (International Publication No. WO 2011/126079 pamphlet) and found that the internal gas bubbles ratio is important for further improvement of water absorbent speed.

However, none of the techniques was able to provide a paper diaper with sufficient water absorbing ability and, in particular, it was not entirely sufficient in terms of weather resistance, impact resistance, coloration, residual monomers, or the like.

Under the circumstances, an object of the present invention is to provide a polyacrylic acid (salt)-based water absorbent resin powder which is excellent in at least one of an absolute water absorption amount [g], a reversion amount (Re-Wet [g]), and an anti-caking property (blocking resistance during moisture absorption) as a paper diaper and excellent weather resistance in addition to excellent liquid permeability (for example, SFC) and water absorbent speed (for example, FSR), and a method for producing the same.

Solution to Problem

For solving the problems described above, it was found that, in addition to Patent Literature 51 (International Publication No. WO 2011/040530 pamphlet), by increasing water absorption capacity (CRC) of Patent Literatures 52 and 53, controlling internal gas bubbles ratio to 0.1 to 2.5%, and also controlling an amount of p-methoxyphenol, which is not described in Patent Literature 53, the above problems can be solved.

Specifically, the polyacrylic acid (salt)-based water absorbent resin powder according to the present invention enables providing a polyacrylic acid (salt)-based water absorbent resin powder in which the water absorption capacity without load (CRC) is 30 to 45 [g/g], the water absorption capacity under load (AAP 0.3) is 20 to 35 [g/g], the water absorption capacity under load (AAP 0.7) is 10 to 28 [g/g], and the weight average particle diameter (D50) is 300 to 500 μm, and it includes p-methoxyphenol, has a degradable soluble component (0.05% L-A (saline) for 2 hours/60° C., one hour extraction rinse/room temperature) of 40% by weight or less, and a internal gas bubbles ratio of 0.1 to 2.5%, as specified by the following equation. Further, the water absorbent resin powder of the present invention preferably contains a metal chelating agent. It also preferably contains inorganic microparticles.

(Internal gas bubbles ratio)[%]={(True density)−(Apparent density)}/(True density)×100

Further, according to the method for producing a polyacrylic acid (salt)-based water absorbent resin powder of the present invention (a first method), provided is a method for producing a water absorbent resin powder which has internal gas bubbles ratio of 0.1 to 2.5% as specified by the following equation, in which the method includes steps of performing foaming polymerization or boiling polymerization of an aqueous monomer solution containing p-methoxyphenol and also acrylic acid as a main component, kneading and grain refining a water-containing gel-like polymer having gas bubbles obtained from the polymerization, heating and drying it at 150 to 250° C. after gel-crushing, pulverizing and classifying a dried product to have an average particle diameter of 300 to 500 μm, and surface crosslinking the pulverized and classified product with internal gas bubbles ratio 0.1 to 2.5% so that the water absorption capacity without load (CRC) is 30 to 45 [g/g], the water absorption capacity under load (AAP 0.3) is 20 to 35 [g/g], and the water absorption capacity under load (AAP 0.7) is 10 to 28 [g/g]. Further, according to the present invention, a metal chelating agent is preferably blended in, and also preferably inorganic microparticles are blended in.

(Closed cell proportion)[%]={(True density)−(Apparent density)}/(True density)×100

Further, according to the method for producing a polyacrylic acid (salt)-based water absorbent resin powder of the present invention (a second method), provided is a method for producing a water absorbent resin powder which has closed cell proportion of 0.1 to 2.5% as specified by the following equation, in which the method includes steps of performing foaming polymerization or boiling polymerization of an aqueous monomer solution containing p-methoxyphenol and also acrylic acid as a main component, obtaining a water absorbent resin which contains p-methoxyphenol and has closed cell proportion of 0.1 to 2.5%, adding a chelating agent during the polymerization or after the polymerization so that the water absorption capacity without load (CRC) is 30 to 45 [g/g], the water absorption capacity under load (AAP 0.3) is 20 to 35 [g/g] and the water absorption capacity under load (AAP 0.7) is 10 to 28 [g/g]. Also preferably, inorganic microparticles are blended in.

From the viewpoint of the water absorption capacity, according to both the first method and the second method, water soluble component of the water adsorbent resin powder is preferably 40% by weight or less, more preferably 30% by weight or less, and still more preferably 20% by weight or less. The lower limit of 10% by weight or so is sufficient. Fe ion amount in the monomer is preferably 3 ppm or less, and more preferably 0.1 to 3 ppm. Further, an inorganic reducing agent is blended in, and a polyvalent metal ion is additionally blended in. Also preferably, a chelating agent and water-insoluble inorganic microparticles are used in combination.

Advantageous Effects of Invention

A polyacrylic acid (salt)-based water absorbent resin powder having excellent water absorption ability as a paper diaper, and a method for producing it are provided.

According to the production method of the present invention, as a water absorbent resin powder having excellent liquid permeability (for example, SFC) or water absorbent speed (for example, FSR), a water absorbent resin powder excellent in terms of resistance to urine, anti-impact stability, and coloration as well as excellent in terms of weather resistance can be obtained.

DESCRIPTION OF EMBODIMENTS

Figure 1:
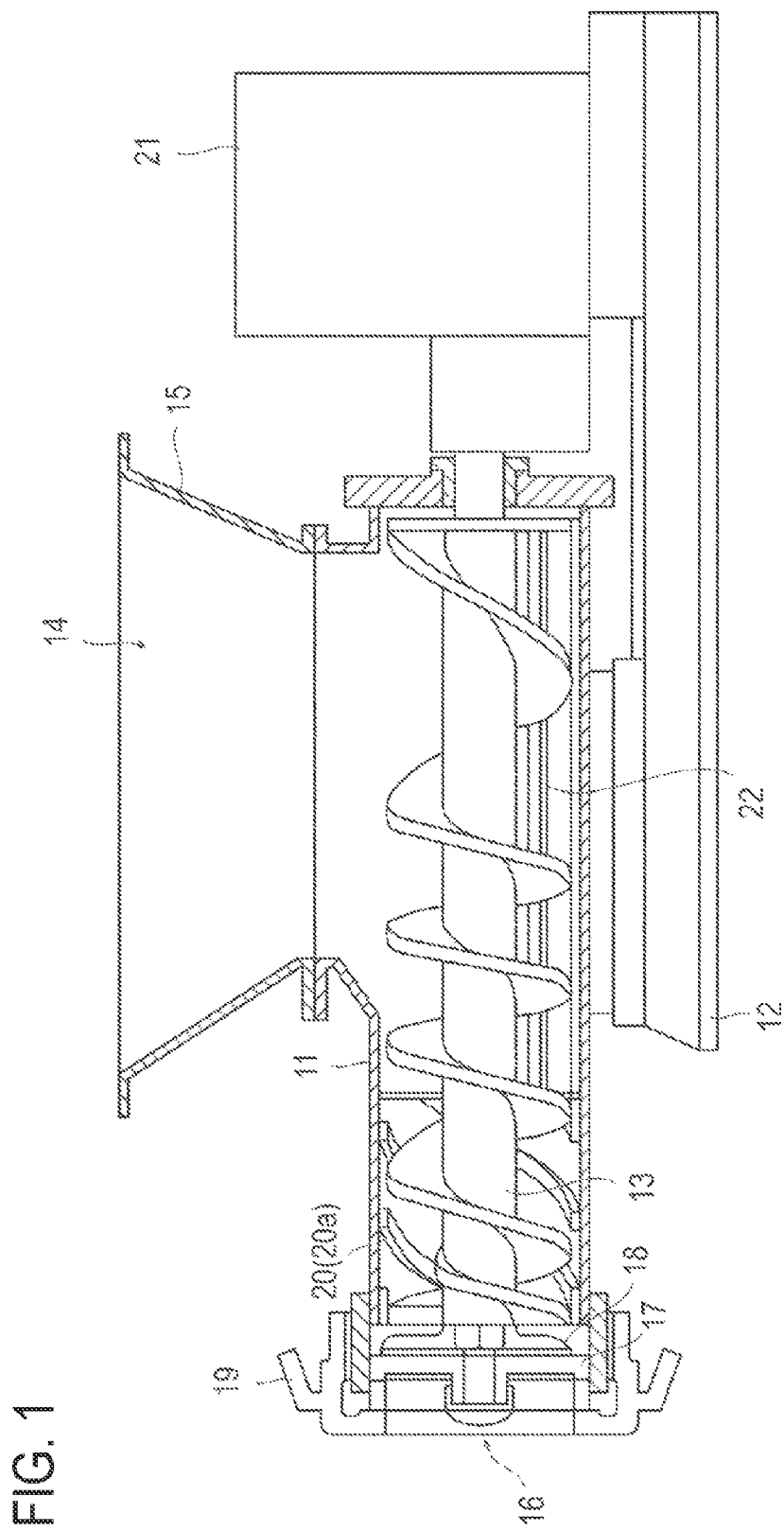
FIG. 1 is a schematic diagram illustrating the configuration of a screw type extruder which is used for the gel-crushing step of a water-containing gel-like crosslinked polymer.

Hereinbelow, the polyacrylic acid (salt)-based water absorbent resin powder according to the present invention and the method for producing it are explained in detail. However, the scope of the present invention is not constricted by those explanations, and those other than the following exemplification can be carried out by appropriately changing them within such the range that the gist of the present invention is not deteriorated.

[1] Definition of Terms (1-1) "Water Absorbent Resin" and "Water Absorbent Resin Powder"

A water absorbent resin in the present invention means a water-swellable water-insoluble polymer gelling agent. In addition, "water-swellable" refers to that CRC (water absorption capacity without load) defined in ERT 442.2-02 is 5 [g/g] or more, and "water-insoluble" refers to that Ext (water soluble component) defined in ERT 470.2-02 is 0 to 50% by weight.

The water absorbent resin can be suitably designed depending on the application. Although it is not particularly limited thereto, it is preferably a hydrophilic crosslinked polymer in which an unsaturated monomer having a carboxyl group is crosslinking-polymerized. Further, it is not limited to that the total amount (100% by weight) is a polymer, but it may contain an additive or the like within the range that aforementioned performance is maintained. That is, even a water absorbent resin composition is also collectively referred to as a water absorbent resin in the present invention.

Further, the "water absorbent resin powder" indicates a water absorbent resin which has constant flowability as powder. For example, it means a water absorbent resin having measurable flow rate (flowing rate) defined by ERT 450.2-02 or a water absorbent resin to be sieve-classified by PSD (particle size distribution) defined by ERT 420.2-02. Specifically, it means a water absorbent resin having a particle diameter of 5 mm or less as defined by sieve classification.

(1-2) "Polyacrylic Acid (Salt)"

In the present invention, the term "polyacrylic acid (salt)" means a polymer, which contains a graft component arbitrarily, and whose main component is acrylic acid and/or its salt (hereinafter, can be referred to as acrylic acid (salt)) as its repeating unit. More specifically, what is meant by the "polyacrylic acid (salt)" is a polymer in which acrylic acid (salt) essentially accounts for 50% by mol to 100% by mol in the total monomer content (excluding an internal crosslinking agent) to be polymerized, preferably a polymer in which acrylic acid (salt) accounts for 70% by mol to 100% by mol in the total monomer content, more preferably a polymer in which acrylic acid (salt) accounts for 90% by mol to 100% by mol in the total monomer content, and particularly preferably a polymer in which acrylic acid (salt) accounts for substantially 100% by mol in the total monomer content. Moreover, in a case where a polyacrylic acid salt is used as a polymer, a water-soluble salt is essentially contained, and a main component of neutralization salt is preferably a monovalent salt, more preferably an alkali metal salt or an ammonium salt, still more preferably an alkali metal salt, and particularly preferably a sodium salt. Meanwhile, although it is not particularly limited, the shape is preferably particle shape or powder shape.

(1-3) "EDANA" and "ERT"

"EDANA" is abbreviation of European Disposables and Nonwovens Associations. "ERT" is abbreviation of EDANA Recommended Test Methods, which is a water absorbent resin measuring method adopted as the European standard (substantially global standard). In the present invention, unless otherwise specified, measurement is carried out according to the ERT master copy (prior literature: 2002 revised version).

(a) "CRC" (ERT 441.2-02)

"CRC" is abbreviation of Centrifuge Retention Capacity, and means water absorption capacity without load (hereinafter, may be referred to as "absorption capacity"). Specifically, CRC is an absorption capacity (unit; [g/g]) measured by allowing 0.2 g of water absorbent resin in unwoven bag to freely swell with a 0.9% by weight aqueous solution of sodium chloride in a largely excess amount for 30 minutes and then draining the water by using a centrifugal separator. CRC of a water-containing gel-like crosslinked polymer (hereinafter referred to as "gel CRC") was also measured under a condition where a sample and a free swelling time were changed to 0.4 g and 24 hours, respectively.

(b) "AAP" (ERT 442.2-02)

"AAP" is abbreviation of Absorption Against Pressure, and means absorption capacity measured under load. Specifically, AAP is absorption capacity (unit; [g/g]) measured by allowing 0.9 g of water absorbent resin to swell with a 0.9% by weight aqueous solution of sodium chloride for 1 hour under a load of 2.06 kPa (0.3 psi, 21 [g/cm$^2$]). Although it is referred to as Absorption Under Pressure in ERT 442.2-02, they are substantially identical with each other. In the present invention and Examples, AAP was measured after changing the load to 4.83 kPa (0.7 psi, 49 [g/cm$^2$]).

(c) "Ext" (ERT 470.2-02)

"Ext" is abbreviation of extractables, and means water soluble component (water soluble component amount). Specifically, it is an amount of dissolved polymer (unit; % by weight) after adding 1.0 g of water absorbent resin into 200 ml of a 0.9% by weight aqueous solution of sodium chloride, stirring at 500 rpm for 16 hours using a 35 mm stirrer chip (other name: 16 hour water soluble component). Measurement of the amount of dissolved polymer is performed by pH titration. A water soluble component of a water-containing gel-like crosslinked polymer (hereinafter referred to as "gel Ext") was also measured under a condition where a sample and a stirring time were changed to 5.0 g and 24 hours, respectively.

(d) "PSD" (ERT 420.2-02)

"PSD" is abbreviation of Particle Size Distribution, and means particle size distribution measured by sieve-classification. Here, a weight average particle diameter (D50), a particle size distribution, and its width (logarithmic standard deviation (σζ)) are measured by the same method as one described in "(1) Average Particle Diameter and Distribution of Particle Diameter" in the specification of EP No. 0349240 (in more detail, EP 1594556 B1). Further, for measuring a particle diameter of a water-containing gel-like crosslinked polymer of a particle shape, the measurement is carried out in view of the method disclosed in JP-A No. 2000-063527.

(e) "Residual Monomers" (ERT 410.2-02)

"Residual monomers" mean quantity of monomers left in water absorbent resin (hereinafter referred to as "residual monomers"). Specifically, residual monomers are quantity (unit; ppm) of monomers dissolved by stirring, at 500 rpm for 1 hour by use of a 35 mm stirrer chip, in 200 ml of a 0.9% by weight aqueous solution of sodium chloride to which 1.0 g of water absorbent resin has been added. The quantity of dissolved monomers is measured by HPLC (high performance liquid chromatography).

(f) "Moisture Content" (ERT 430.2-02)

"Moisture content" means moisture content of water absorbent resin. Specifically, the moisture content (unit; % by weight) is a value calculated from drying loss obtained by drying 4 g of water absorbent resin at 105° C. for 3 hours. In the present invention and the Examples, measurement was made after changing the water absorbent resin to 1 g and drying temperature condition to 180° C.

(g) "Density" (ERT 460.2-02)

"Density" means bulk specific gravity of a water absorbent resin. Specifically, the density is weight (unit; [g/ml]) of a water absorbent resin filling a 100 mL container into which 100 g of the water absorbent resin which has been supplied into a device satisfying EDANA standards is freely dropped.

(h) "Flow Rate" (ERT 450.2-02)

"Flow rate" means a flow rate of water absorbent resin. Specifically, the flow rate is a period of time (unit; sec) required for discharging, from an opening in an undermost part of a device satisfying EDANA standards, 100 g of water absorbent resin which has been supplied into the device.

(1-4) "Liquid Permeability"

"Liquid permeability" in the present invention indicates a flowing of a liquid between particles of swollen gel under load or without load. The "liquid permeability" is measured typically as SFC (Saline Flow Conductivity) or GBP (Gel Bed Permeability).

"SFC" is liquid permeability of water absorbent resin to a 0.69% by weight aqueous solution of sodium chloride under a load of 2.06 kPa (0.3 psi), and measured according to the SFC test method described in U.S. Pat. No. 5,669,894. Moreover, "GBP" is liquid permeability of water absorbent resin to a 0.69% by weight sodium aqueous solution of chloride wherein the water absorbent resin is under load or allowed to freely swell. GBP is measured according to the GBP test method described in International Publication No. WO 2005/016393 pamphlet.

(1-5) "FSR"

"FSR" of the present inventions is abbreviation of Free Swell Rate, and means a water absorbent speed (free swell rate). Specifically, FSR is a rate (unit; [g/g/s]) at which 1 g of water absorbent resin absorbs 20 g of a 0.9% by weight aqueous solution of sodium chloride.

(1-6) "Gel-Crushing", "Weight Average Molecular Weight of Water Soluble Component", and "Gel Grinding Energy (GGE, GGE (2))"

Disclosures in [0045] to [0053] of Patent Literature 53 (International Publication No. WO 2011/126079 pamphlet), which is an unpublished prior application on the priority date of the present application, are also applied to the present invention.

(1-7) Others

In this specification, the expression "X to Y" for expressing a range means "not less than X and not more than Y". The weight unit "t (ton)" means "Metric ton". Moreover, "weight" and "mass", "% by weight" and "% by mass", and "parts by weight" and "parts by mass" are synonymous with each other correspondingly herein. Further, unless otherwise specified, "ppm" means "ppm by weight" or "ppm by mass". Further, the expression " . . . acid (salt)" means " . . . acid and/or salt thereof". The expression "(meth)acrylic" means "acrylic and/ or methacrylic".

[2] Polyacrylic Acid (Salt)-Based Water Absorbent Resin Powder

The polyacrylic acid (salt)-based water absorbent resin powder according to the present invention is a water absorbent resin powder in which the water absorption capacity without load (CRC) is 30 to 45 [g/g], the water absorption capacity under load (AAP 0.3) is 20 to 35 [g/g], the water absorption capacity under load (AAP 0.7) is 10 to 28 [g/g], and the weight average particle diameter (D50) is 300 to 500 μm, and it includes p-methoxyphenol, has a degradable soluble component (0.05% L-A (saline) for 2 hours/60° C., one hour extraction rinse/room temperature) of 40% by weight or less, and a internal gas bubbles ratio of 0.1 to 2.5%, as defined by the following equation.

(Internal gas bubbles ratio)[%]={(True density)−(Apparent density)}/(True density)×100

Hereinbelow, each constitution of the polyacrylic acid (salt)-based water absorbent resin powder according to the present invention and a method for controlling it are explained.

(2-1) Internal Gas Bubbles Ratio

According to the present invention, the internal gas bubbles ratio is further controlled compared to Patent Literature 51. Specifically, the polyacrylic acid (salt)-based water absorbent resin powder according to the present invention is controlled such that it has the internal gas bubbles ratio of 0.1 to 2.5%, as defined by the following equation. The internal gas bubbles ratio can be measured by the method described in the Examples, similar to Patent Literatures 52 and 53. Specifically, it can be defined by the following principles.

(Internal gas bubbles ratio)[%]={(True density)−(Apparent density)}/(True density)×100

What is meant by "true density" in the present invention is density (unit; [g/cm$^3$]) which is fixedly determined from chemical composition (repeating unit of a polymer, minute raw materials such as the crosslinking agent, graft component used arbitrarily, etc.) with respect to water absorbent polyacrylic acid (salt)-based resin which is sufficiently dried (moisture content of preferably less than 1% by weight, more preferably less than 0.5% by weight, and particularly preferably less than 0.1% by weight). Therefore, the true density of the water absorbent polyacrylic acid (salt)-based resin having the same solid content is substantially constant, even though it may vary slightly due to its neutralization rate, the type of its salts (for example, sodium polyacrylate or the like having a neutralization rate of 75% by mol), or the minute raw materials.

Meanwhile, what is meant by "apparent density" in the present invention is density (unit; [g/cm$^3$]) determined in consideration of pores (in other words, internal gas bubbles or closed-cells) that are present inside the particles of the polyacrylic acid (salt)-based water absorbent resin powder.

Figure 2:
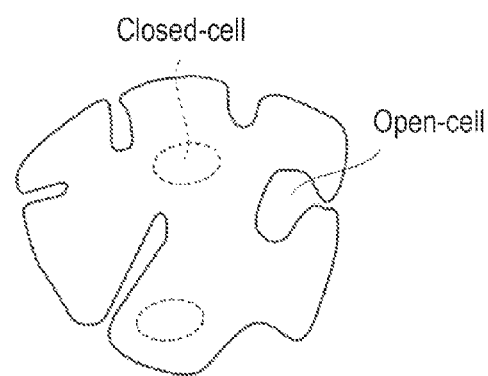
FIG. 2 is a cross-sectional view schematically illustrating the closed-cell and open-cell in the water absorbent resin powder.

For example, a water absorbent resin obtained by foaming polymerization or water absorbent resin having been subjected to the granulation step has a space (open-cell; open pore) on the surface, which space is communicated with its outside, and a space (void; internal gas bubble, closed-cell; closed pore) inside, which space is not communicated with its outside, as illustrated in FIG. 2. Thus, when the density of the water absorbent resin is measured by dry density measurement, the apparent density is obtained from the volume not including the open pore (open-cell) but including the closed pore (closed-cell) because introduced gas cannot enter the closed pore, it can enter the open pore. Regarding the apparent density of water absorbent resin, Non-Patent Literature 1, pages 197 to 199, discloses that water absorbent resin having been subjected to 40 to 60 mesh-cut is measured by wet measurement in which the measurement is carried out by use of methanol. The apparent density of the present invention is characterized in being measured by the dry measurement for all particle sizes. It is found that the internal gas bubbles ratio defined by using such apparent density is important for improvement of the physical properties of the water absorbent resin.

The density (true density and apparent density) of the water absorbent resin can be accurately measured by the dry density measurement in which a predetermined gas is used. The dry density measurement for solid is based on such measurement principle that has been well known in an isovolumetric swelling method in which volume of the solid is measured by use of a particular gas. Specifically, assuming that the volume of gas bubbles of a sample, $V_{CELL}$, and the volume of the gas bubbles expanded, $V_{exp}$, are known, the volume of the sample, $V_{SAMP}$, can be obtained by measuring pressures (gage pressures) $P_{1g}$ and $P_{2g}$, and the density of the sample can be obtained by dividing the weight of the sample by volume of the sample after separately measuring the weight (see, Shimadzu Corporation; http://www.shimadzu.co.jp/powder/lecture/middle/m04.html).

The true density is fixedly determined from the chemical composition (mainly, the repeating unit of the polymer). Thus, a known value may be used as the true density. If there is unknown value for the true density of the water absorbent resin because the true density is varied slightly due to the minute raw materials or the like, the true density may be determined by a method described below in Examples. Further, the water absorbent resin has substantially no closed-cell by being subjected to pulverization by which the closed-cells in the water absorbent resin are broken or converted into open-cells. Therefore, the density of the water absorbent resin thus subjected to pulverization can be regarded as the true density. Here, the "open-cells" are gas bubbles communicating with outside, and are not counted into the volume of the water absorbent resin in the dry density measurement. Thus, the closed-cells and the open-cells can be easily distinguished from each other by the dry density measurement.

Meanwhile, the internal gas bubbles ratio (other name; closed-cell ratio) of the water absorbent resin powder of the present invention is 0.1 to 2.5%. The lower limit is within the above range, 0.2% or more, 0.3% or more, 0.5% or more, 0.7% or more, or 0.8% or more, which is more preferable in that order. Further, the upper limit is within the above range, 2.0% or less, 1.7% or less, 1.5% or less, 1.3% or less, or 1.2% or less, which is more preferable in that order. For example, the internal gas bubbles ratio is preferably 0.5 to 2.5% or 0.2 to 2.0%, more preferably 0.3 to 1.7%, still more preferably 0.5 to 1.5%, and most preferably 0.8 to 1.2%. By controlling the internal gas bubbles ratio to be within the above range, a water absorbent resin powder having water absorbent speed and liquid permeability or anti-impact stability defined in the invention is obtained. The internal gas bubbles ratio can be controlled based on gel grinding energy, increased width of molecular weight of a water soluble component, or the like according to the production method of the present invention. However, a method like foaming polymerization (for example, use of an azo initiator), foaming during drying, or the like may be employed (used in combination). Meanwhile, to excessively lower the internal gas bubbles ratio, high energy for gel-crushing or fine-pulverizing after drying is required and it may cause a decrease in other physical properties. Thus, the desirable lower limit is within the aforementioned range.

Patent Literature 52 (International Publication No. WO 2011/078298 pamphlet) as an unpublished prior application on the priority date of the present application describes producing a water absorbent resin powder, into which fine gas bubbles (closed-cells) are introduced, by adding a surfactant into an aqueous monomer solution, and then polymerizing the aqueous monomer solution. The international application describes employing a internal gas bubbles ratio for calculating how much the closed-cells account for in the water absorbent resin powder, and also describes that the internal gas bubbles ratio is preferably in a range of 2.8% to 6.6%. Further, it describes that having a internal gas bubbles ratio within that range makes it possible to improve a water absorbent speed (FSR) and liquid permeability (SFC) of the water absorbent resin which are the physical properties contradicting each other.

Further, in Table 3 of Patent Literature 52 (Examples 11 and 12 and Comparative examples 10 to 12), although the water absorbent resin powder with a internal gas bubbles ratio of 2.60 to 6.83[%] is disclosed as a water absorbent resin powder having AAP increased to 20 [g/g] or higher by surface crosslinking is disclosed, the problems are solved by the present invention by improving the water absorption capacity (CRC) to 30 to 45 [g/g] and also controlling the internal gas bubbles ratio at a low level. Controlling the water absorption capacity (CRC) can be appropriately made based on the amount of crosslinking agent or use of a chain transfer agent during polymerization, or the amount of surface crosslinking agent or reaction time during surface crosslinking, or the like.

(Method for Controlling Internal Gas Bubbles)

The internal gas bubbles ratio can be controlled based on gel grinding energy, increased width of molecular weight of a water soluble component, or the like according to the production method of the present invention. For controlling the internal gas bubbles ratio, there is a method of controlling an occurrence of gas bubbles at a low level during polymerization or a method of controlling an occurrence of gas bubbles at a low level during drying, or the like. However, the gel-crushing described in Patent Literature 53 (International Publication No. WO 2011/126079 pamphlet), which is an unpublished prior application on the priority date of the present application, that is, the gel-crushing explained below, is preferably used.

(2-2) Amount of MEHQ

Like Patent Literature 51 (International Publication No. 2011/040530 pamphlet), as the water absorbent resin powder according to the present invention contains p-methoxyphenol (amount of MEHQ) preferably at 5 ppm to 60 ppm, preferably 5 ppm to 50 ppm, more preferably 5 ppm to 40 ppm, and still more preferably 5 ppm to ppm, a water absorbent resin powder having more excellent weather resistance can be provided. If the amount of p-methoxyphenol is too much, coloration may be caused. If it is small, the weather resistance may be deteriorated. Meanwhile, Non-Patent Literature 1, chapter "2.5.3. Inhibition" (polymerization inhibitor) (pages 39 to 44) discloses in Tables 2.5 that commercially available water absorbent resins (8 kinds) contain MEHQ in an amount of 16 ppm to 151 ppm. However, Non-Patent Literature 1 does not disclose the effect of the present invention (particularly, coloration prevention and weather resistance by controlling within a predetermined range).

(Method for Addition)

From the viewpoint of the effect, it is preferable that p-methoxyphenol (MEHQ) is uniformly contained inside the water absorbent resin powder. Thus, it is preferable to have a pre-determined amount of MEHQ in monomers for polymerization (an aqueous monomer solution).

Because part of p-methoxyphenol is consumed by polymerization or drying, it can be suitably controlled, the control can be made based on the polymerization and drying, and for example, the amount in a final water absorbent resin powder may be adjusted based on the method described in Patent Literature 51 or related Patent Literature 52.

Specifically, the control can be made by, after polymerizing (with the aforementioned concentration, temperature, polymerization initiator, or the like) an aqueous monomer solution containing acrylic acid (salt) as a main component in which p-methoxyphenol is contained at preferably 5 to 200 ppm, more preferably 5 to 130 ppm, still more preferably 5 to 100 ppm, particularly preferably 5 to 80 ppm, and most preferably 5 to 50 ppm relative to the monomer solid content, drying the water-containing gel-like crosslinked polymer obtained by the polymerization under the condition in the aforementioned preferred range (with the aforementioned temperature, time, wind speed, solid content, or the like).

It is well known that p-methoxyphenol is used in an amount of 200 ppm as a common inhibitor for polymerization of acrylic acid. It is also well known that acrylic acid (boiling point: 143° C.) is purified by distillation during polymerization of a water absorbent resin (for example, U.S. Pat. No. 6,388,000) or an acrylic acid salt is treated with activated carbon. According to such purification by distillation, p-methoxyphenol is substantially removed from acrylic acid, and therefore it cannot be the p-methoxyphenol of the present invention.

According to a more preferred embodiment, a step of neutralizing whole or part of acrylic acid with a base having a Fe content of 0 to 7 ppm is further included before the polymerization step, the polymerization step is a step of performing, under condition including maximum temperature of 130° C. or less and polymerization time of between 0.5 min to 3 hours, aqueous solution polymerization or reverse-phase suspension polymerization of an aqueous monomer solution with a monomer concentration of 30 to 55% by weight, in which acrylic acid (salt) is contained at 90 to 100% by mol in the monomer, using 0.001 to 1% by mol of a polymerization initiator (relative to the monomer), the heating and drying step is a step of drying the water-containing gel-like crosslinked polymer, which has been obtained in a particle shape by polymerization, to have a moisture content of 20% by weight or less at a drying temperature of 100 to 250° C. and with a drying time of 10 to 120 min, and the surface crosslinking step is a step of mixing 0.001 to 10 parts by weight of a surface crosslinking agent relative to 100 parts by weight of the water absorbent resin powder after completion of the pulverizing and classification step, and performing a heating treatment for 1 minute to 2 hours at 70 to 300° C. According to the embodiment, content of p-methoxyphenol in the water absorbent resin powder can be adjusted to the aforementioned range (for example, 5 to 50 ppm).

(Method for Quantification)

Method for quantifying p-methoxyphenol is described in Patent Literature 51. That is, except that the stirring time is changed from 16 hours to 1 hour, p-methoxyphenol contained in the water absorbent resin powder is obtained by performing the same operation as the method of evaluating "Ext" described above and analyzing a filtrate obtained from it. Specifically, by analyzing the filtrate obtained from above operations by high performance liquid chromatography, p-methoxyphenol in the water absorbent resin powder can be obtained. Meanwhile, p-methoxyphenol is expressed in ppm (relative to the water absorbent resin powder).

(2-3) Water-Insoluble Inorganic Microparticles

It is preferable that the water absorbent resin powder according to the present invention further includes water-insoluble inorganic microparticles like Patent Literature 51 (International Publication No. WO 2011/040530 pamphlet). From the viewpoint of improving the liquid permeability (SFC), flowability during water absorption or the like, and also from the viewpoint of improving absolute water absorption amount of a paper diaper indicated in Examples, it is preferable to contain water-insoluble inorganic microparticles, in particular white water-insoluble inorganic microparticles.

The water absorption capacity (CRC) hardly changes even when water-insoluble inorganic microparticles are used. However, as an absolute water absorption amount of a paper diaper or a core described below is improved, it is desirable. Further, by adding white water-insoluble inorganic microparticles, white color hue of an obtained water absorbent resin powder is further improved and gel strength of the water absorbent resin powder is enhanced, and therefore desirable.

Herein, whiteness of the water-insoluble inorganic microparticles is, in terms of the values of L, a, and b, 70 or higher (value L), within ±5 (value a), and within ±10 (value b), preferably 80 or higher (value L), within ±3 (value a), and within ±7 (value b), and more preferably 90 or higher (value L), within ±2 (value a), and within ±5 (value b). Further, water-insoluble inorganic microparticles having higher whiteness than the water absorbent resin powder before mixing (L is preferably 5 or higher, further 7 or higher) are used. Mixing method may be either dry blending or addition into a slurry liquid in which dispersion is made in a solvent (water, in particular) or a solution of surface crosslinking agent. Solvent is 0 (not used) to 10 parts by weight relative to 100 parts by weight of the water absorbent resin powder, for example.

The water-insoluble inorganic microparticles are the microparticles with an average particle diameter in the range of preferably 0.001 to 200 μm, more preferably 0.005 to 50 μm, and still more preferably 0.01 to 10 μm as measured by coulter counter method. Preferably, they are hydrophilic microparticles and examples thereof include metal oxide such as silica (silicon dioxide) or titanium oxide, a complex hydrous oxide containing zinc and silicon, or zinc and aluminum (for example, those exemplified in International Publication No. WO 2005/010102 pamphlet), silicic acid (salt) such as natural zeolite or synthetic zeolite, kaolin, talc, clay, bentonite, calcium phosphate, barium phosphate, silicic acid or its salts, clay, diatomaceous earth, silica gel, zeolite, bentonite, hydroxyapatite, hydrotalcite, vermiculite, pearlite, isolite, activated white clay, silica, silex, strontium ore, fluorite, bauxite, and the like. Of those, silicon dioxide and silicic acid (salt) are more preferable.

The silicon dioxide is, although not particularly limited, preferably amorphous fumed silica produced by a dry method. Silicon dioxide called quartz or the like is not preferable because it has a possibility of causing health problems.

Content of the water-insoluble inorganic microparticles is, relative to the water absorbent resin powder, preferably in the range of 0.05 to 1.0% by weight, more preferably in the range of 0.05 to 0.8% by weight, still more preferably in the range of 0.05 to 0.7% by weight, and particularly preferably in the range of 0.1 to 0.5% by weight. When the content of the water-insoluble inorganic microparticles is 0.05% by weight or more on a surface of the water absorbent resin powder having a internal gas bubbles ratio controlled to a low level, an anti-cracking property (blocking resistance during water absorption) or an absolute water absorption amount by a paper diaper is improved, and thus deterioration in urine resistance can be suppressed. Further, when the content of the water-insoluble inorganic microparticles is 1.0% by weight or less, a decrease in water absorption capacity under load of the water absorbent resin powder can be suppressed.

(Method for Addition)

The water-insoluble inorganic microparticles are used for a water absorbent resin after drying, particularly preferably during or after the surface crosslinking step, or during or after the subsequent second surface crosslinking step, and the surface of the water absorbent resin is coated with the water-insoluble inorganic microparticles. Mixing the water-insoluble inorganic microparticles with a water absorbent resin may be dry blend or addition of slurry containing them as dispersed in a solvent.

(2-4) Amount of Water Soluble Polyvalent Metal

It is preferable that the water absorbent resin powder according to the present invention further includes, similar to Patent Literature 51 (International Publication No. WO 2011/040530 pamphlet) or Patent Literatures 52 and 53, a water soluble polyvalent metal salt (provided that, iron salt is excluded), that is, a water soluble polyvalent metal cation (provided that, iron salt is excluded).

From the viewpoint of enhancing water absorbent speed (vortex) and liquid permeability (SFC), flowability during water absorption or the like, it is preferable that the water absorbent resin powder according to the present invention further contains a polyvalent metal salt and/or a cationic polymer.

The polyvalent metal cation is an organic acid salt or an inorganic acid salt of polyvalent metal. Preferred examples thereof include a polyvalent metal salt of aluminum, zirconium, titanium, calcium, magnesium, zinc, or the like. The polyvalent metal salt may be any one of water soluble and water-insoluble ones. However, a water soluble polyvalent metal salt is preferable and a water soluble polyvalent metal salt which is dissolved at 2% by weight or more, or 5% by weight or more in 25° C. water can be used. Specific examples thereof include inorganic acid salts such as aluminum chloride, aluminum polychloride, aluminum sulfate, aluminum nitrate, potassium aluminum bissulfate, sodium aluminum bissulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium sulfate, or zirconium nitrate, and an organic acid salt such as a lactic acid salt or an acetic acid salt of those polyvalent metals. Also from the viewpoint of a dissolution property in a liquid to be absorbed like urine, it is preferable to use those salts having crystal water. It may be used either singly or in combination of two or more types. The polyvalent metal salt is preferably a trivalent salt or a tetravalent salt, and an aluminum salt or a zirconium salt is used.

The content of the water soluble polyvalent metal salt which is added as powder or solution is, in terms of cation amount (for example, $Al^{3+}$) preferably in the range of 0.001 to 5% by weight, more preferably in the range of 0.001 to 3% by weight, and still more preferably in the range of 0.01 to 2% relative to the water absorbent resin powder. When the content is 5% by weight or less, a decrease in water absorption performance (in particular, water absorption capacity) can be suppressed. Meanwhile, when it is 0.001% by weight or more, the water absorbent speed, liquid permeability (SFC), and flowability during water absorption can be improved. Meanwhile, when it is contained as a powder, the particle diameter is within the same range as the water-insoluble inorganic microparticles.

(Method for Addition)

The water soluble polyvalent metal salt is used, in the form of powder, solution, or slurry liquid, for a water absorbent resin after drying, particularly preferably in the surface crosslinking step or in the following second surface crosslinking step, and the surface of the water absorbent resin is coated or reacted with the polyvalent metal salt. The addition method disclosed in Patent Literature 51 (International Publication No. WO 2011/040530 pamphlet) (1-10), Patent Literature 52 (2-6), or Patent Literature 53 (2-5) can be preferably applied. The disclosures are considered as the disclosure of the present application.

(2-5) Chelating Agent

To solve the problems, in particular to obtain a water absorbent resin powder which is prevented from being deteriorated by urine and coloration, similar to Patent Literature 51 (International Publication No. 2011/040530 pamphlet) and has high water absorption capacity, the water absorbent resin powder of the present invention preferably contains a metal chelating agent (hereinbelow, also simply referred to as a "chelating agent"). As for the chelating agent of the present invention, a polymer compound or a non-polymer compound is preferable from the viewpoint of the effect. Among them, a non-polymer compound is preferable. Specifically, a compound selected from amino polyvalent carboxylic acid, polyvalent organic phosphoric acid, polyvalent inorganic phosphoric acid, and amino polyvalent phosphoric acid is preferable. From the viewpoint of the effect, the molecular weight of the chelating agent is preferably 100 to 5000, and more preferably 200 to 1000. When the chelating agent is contained, a water absorbent resin powder excellent from the viewpoint of coloration or deterioration is obtained. The chelating agent which may be used for the present application is exemplified in paragraphs [0104] to [0108] of Patent Literature 51 [2], and the disclosures are considered as the disclosure of the present application.

Herein, "polyvalent" means that a plurality of the functional group are present in one molecule, and the functional group is preferably present in a number of 2 to 30, further 3 to 20, or 4 to 10. The chelating agents are a water soluble chelating agents. Specifically, it is a water soluble chelating agent, which is dissolved in 1 g or more or further 10 g or more in 100 g (25° C.) water, and further a water soluble non-polymer chelating agent is preferable.

Meanwhile, among the chelating agents exemplified in Patent Literature 51, from the viewpoint of preventing coloration, an aminocarboxylic acid-based metal chelating agent, an amino polyvalent phosphoric acid-based metal chelating agent, and salts thereof are preferably used. Preferred number of the functional group (an acid group, in particular, an acid group consisting of carboxyl group and phosphoric acid group) is within the aforementioned range (2 to 30, further 3 to 20, 4 to 10, or 5 to 9). In particular, diethylenetriamine pentaacetic acid, triethylenetetramine hexaacetic acid, trans-1,2-diaminocyclohexane tetraacetic acid, ethylenediamine tetra(methylenephosphinic acid), ethylenediamine tetra(methylenephosphonic acid), diethylenetriamine penta(methylenephosphonic acid), and salts thereof are preferably used. Among them, diethylenetriamine pentaacetic acid, triethylenetetramine hexaacetic acid, and ethylenediamine tetra(methylenephosphonic acid) are more preferably, and ethylenediamine tetra(methylenephosphonic acid), and salts thereof are most preferable. As for the salt, a monovalent salt is preferable, and examples thereof include an alkali metal salt such as a sodium salt and a potassium salt, an ammonium salt and an amine salt. Among those salts, the sodium salt and the potassium salt are particularly preferable. Among them, diethylenetriamine pentaacetic acid, triethylenetetramine hexaacetic acid, and ethylenediamine tetra(methylenephosphonic acid) are more preferable, and ethylenediamine tetra(methylenephosphonic acid) and salts thereof are most preferable. As for the salt, a monovalent salt is preferable, and examples thereof include an alkali metal salt such as a sodium salt and a potassium salt, an ammonium salt and an amine salt. Among those salts, the sodium salt and the potassium salt are particularly preferable.

Content of the chelating agent is, relative to the water absorbent resin powder, 0.001 to 2% by weight, or further 0.001 to 0.5% by weight, preferably 0.001 to 0.1% by weight, more preferably 0.002 to 0.1% by weight, still more preferably 0.003 to 0.05% by weight, and particularly preferably 0.005 to 0.05% by weight. If the content of the chelating agent is less than 0.001% by weight, urine resistance or color hue with the lapse of time (coloration during storage) is deteriorated, and therefore undesirable. On the other hand, when the content of the chelating agent is more than 0.5% by weight, it is found to have high initial coloration and also the initial color hue (coloration right after production) may be deteriorated, and therefore undesirable.

(Method for Addition)

The chelating agent may be added in any one step or more of the polymerization step, gel-grain refining step, drying step, pulverizing step/classification step, surface crosslinking step, and other steps described below. In the polymerization, the chelating agent may be added during preparing monomers before the polymerization step, or the chelating agent may be added during the polymerization. The addition method of Patent Literature 51 (International Publication No. WO 2011/040530 pamphlet) or Patent Literatures 52 and 53, which are a unpublished prior application at the priority date of the present application, can be preferably applied. Preferably, the metal chelating agent is mixed after the polymerization step.

According to addition during the polymerization, the chelating agent can be evenly contained inside the water absorbent resin powder, and thus uniform prevention of deterioration can be achieved. Further, according to the addition of a chelating agent after the polymerization, in particular after drying, the chelating agent can be contained on a surface of the water absorbent resin powder, and thus deterioration or coloration of a surface of water absorbent resin powder, which is more prone to deterioration or coloration, can be suppressed, and adding them in combination is also preferable. In Patent Literatures 52 and 53 as a prior application, use of a chelating agent during polymerization is disclosed. Due to the reasons described above, in the present invention, the chelating agent is preferably contained on a surface, and also a chelating agent present inside the polymer is also used in combination.

The use amount in those production steps substantially correspond to the content in the obtained water absorbent resin powder. According to the method described in Patent Literature 51, the chelating agent can be suitably quantified by liquid chromatography, ion chromatography or the like after extracting it from a water absorbing agent using water or saline in the same manner as quantification of residual monomers or water soluble component.

(2-6) Amount of Fe Ion

Similar to Patent Literature 51, content of Fe ion in the water absorbent resin powder according to the present invention is (in terms of Fe2O3), preferably 3 ppm or less, more preferably 2 ppm or less, still more preferably 1.5 ppm or less, still more preferably 1 ppm or less, still more preferably 0.5 ppm or less, further still more preferably 0.1 ppm or less, and particularly preferably 0.02 ppm or less, from the viewpoint of preventing coloration. Meanwhile, although lower limit of Fe ion is not particularly limited, it is sufficient to have 0.1 ppm or 0.02 ppm or so from the viewpoint of the effect relative to cost. From the viewpoint of cost for purification of raw materials, it is preferably 0.001 ppm or more, more preferably 0.01 ppm or more, and even more preferably 0.1 ppm or more. Thus, the upper limit and lower limit are selected within the above range, and it is 3 (2, 1, 1.5, 1, 0.5) to 0.1 ppm, for example. For controlling an amount of Fe ion, it is possible to control the amount of Fe ion in the raw materials of the water absorbent resin powder by, in particular, purifying suitably a base used for neutralization, for example by removing Fe contained in NaOH, $Na_2CO_3$. The amount of Fe ion can be measured in the raw materials or the final water absorbent resin powder. In other words, it is preferable that the content of iron ion in the monomer is within the aforementioned range.

Meanwhile, the expression "in terms of $Fe_2O_3$" means that an absolute amount of Fe in Fe only or a compound containing it (for example, $Fe_2O_3$, or iron slats, iron hydroxide, or iron complexes thereof) is expressed as an iron compound represented by $Fe_2O_3$ (molecular weight of 159.7) and it corresponds to the weight after oxidizing all counter parts of Fe. As a Fe portion, the iron amount can be generally calculated as molecular weight of 55.85×2/159.7 (Fe in $Fe_2O_3$).

For example, when acrylic acid is neutralized with NaOH having Fe of 10 ppm (for obtaining an Fe amount based on the amount of $Fe_2O_3$, it is calculated as amount of $Fe_2O_3$×55.85× 2/159.7), from $CH_2$=CHCOOH (molecular weight of 72)+ NaOH (molecular weight of 40, Fe is about 7 ppm)→ $CH_2$=CHCOONa (molecular weight of 94) and for sodium acrylate (molecular weight of 88.55) with neutralization rate of 75% by mol, there is about 3 ppm of the amount of Fe in the obtained sodium polyacrylate (7 ppm×40/88.55=about 3 ppm). Such pre-determined amount of iron promotes degradation of the water absorbent resin powder at the time of disposal after use. However, use of an excess amount of iron serves as a cause of deterioration during use or coloration before use, and therefore undesirable.

(Method for Control)

Control of an iron amount is mainly performed by controlling the base used for neutralization (in particular, caustic soda), and it may be also performed by controlling a trace amount of iron in raw materials (acrylic acid, crosslinking agent, water, or the like) or a resin coat, a glass coat, stainless, or the like of various apparatuses or pipes for water absorbent resin powder such as polymerization reaction apparatus or a monomer pipe. Meanwhile, the iron amount in the base or water absorbent resin powder can be quantified by ICP spectrophotometric analysis described in JIS K1200-6, for example. As a reference literature for quantification method, reference can be made to International Publication No. WO 2008/090961 pamphlet.

(2-7) Reducing Agent

The water absorbent resin powder according to the present invention contains preferably an inorganic or organic reducing agent described in Patent Literature 51, and still more preferably an inorganic reducing agent, a water soluble inorganic compound having reducing inorganic element, or a water soluble organic compound having reducing inorganic element. Meanwhile, the term "water soluble" means the solubility of 1 g or more, further 5 g or more, or particularly 10 g or more in 100 g of water at 25° C.

It is sufficient for the inorganic reducing agent according to the present invention to have a reducing inorganic element. Specific examples thereof include a compound having a reducing sulfur atom or a reducing phosphorus atom. Preferable examples thereof include a compound containing a reducing sulfur atom or a water soluble compound containing a reducing phosphorus atom.

Examples of the inorganic compound containing a sulfur atom as an inorganic reducing agent include, although not particularly limited, sulfite such as sodium sulfite, potassium sulfite, calcium sulfite, zinc sulfite, or ammonium sulfite; hydrogen sulfite such as sodium hydrogen sulfite, potassium hydrogen sulfite, calcium hydrogen sulfite, or ammonium hydrogen sulfite; pyrosulfites such as sodium pyrosulfite, potassium pyrosulfite, or ammonium pyrosulfite; dithionites such as sodium dithionite, potassium dithionite, ammonium dithionite, calcium dithionite, or zinc dithionite; trithionites such as potassium trithionite or sodium trithionite; tetrathionites such as potassium tetrathionite or sodium tetrathionite; thiosulfates such as sodium thiosulfate, potassium thiosulfate, or ammonium thiosulfate; nitrites such as sodium nitrite, potassium nitrite, calcium nitrite, or zinc nitrite; and the like, and examples of an inorganic compound containing a phosphorus atom include sodium hypophosphite, or the like. Among them, sulfites, hydrogen sulfites, pyrosulfites, and dithionates are preferable. Sodium sulfite, sodium hydrogen sulfite, potassium pyrosulfite, and sodium dithionite are more preferable.

Further, examples of the water soluble organic compound containing a sulfur atom as an inorganic reducing agent include, although not particularly limited, 2-hydroxy-2-sulfinate acetic acid sodium formaldehydesulfoxylate, foramidine sulfinic acid, thioglycolic acid tris(2-carboxyethyl)phosphine hydrochloride (TCEP), tributylphosphine (TBP), and the like. Among them, 2-hydroxy-2-sulfinate acetic acid, 2-hydroxy-2-sulfonatoacetic acid, and/or salts thereof are preferably exemplified.

In the present invention, the inorganic reducing agent is, relative to the solid content of monomer or polymer, preferably 0.01 to 1.0% by weight, more preferably 0.05 to 1.0% by weight, and particularly preferably 0.05 to 0.5% by weight. When the content of inorganic reducing agent is 0.01% by weight or more, coloration with the lapse of time or deterioration by urine can be suppressed, and it may also contribute to a decrease in residual monomers. Further, when the content of inorganic reducing agent is 1.0% by weight or less, malodor can be suppressed, and in particular, malodor after absorbing an aqueous liquid can be effectively suppressed.

(Method for Addition)

As for inorganic reducing agent, the addition method described in Patent Literature 51 can be preferably applied, and also it may be added in any one step or more of the polymerization step, gel-grain refining step, drying step, pulverizing step/classification step, surface crosslinking step, and other steps (for example, addition step after crosslinking or the like) described below. For the polymerization step, it may be added at the time of starting polymerization. However, as a reducing agent is generally consumed, it is preferably added during the polymerization or after the polymerization step, and it can be added by including the amount of the reducing agent that is consumed during the production process, in particular the drying step. Preferably, it is added after the polymerization step from the viewpoint of reducing residual monomers. From the viewpoint of preventing coloration, resistance to urine, or preventing malodor, the reducing agent is further mixed after the drying step. For the addition of a reducing agent, powder of reducing agent may be dry-blended. However, from the viewpoint of the effect, in particular, the effect of reducing residual monomers, it is added as an aqueous solution (for example, 0.5 to 20 parts by weight of water relative to 100 parts by weight of the water absorbent resin powder), and preferably the moisture content [%] in a final water absorbent resin is preferably within the range described below.

(2-8) Water Absorption Capacity, Water Absorption Capacity Under Load, Particle Size, and the Like (Additional Physical Properties)

The polyacrylic acid (salt)-based water absorbent resin powder obtained by the production method of the present invention has water absorption capacity without load (CRC) of 30 to 45 [g/g], water absorption capacity under load (AAP 0.3) of 20 to 35 [g/g], and water absorption capacity under load (AAP 0.7) of 10 to 28 [g/g], and also further preferably satisfies the following physical properties. When it is used as a hygienic material, in particular paper diaper, having the water absorbent resin powder as a main component, it is preferable that two or more, in particular, three or more physical properties including AAP are controlled by the polymerization method, surface crosslinking method or the like described above. When the water absorbent resin powder does not satisfy each of the following physical properties, a high concentration paper diaper having the water absorbent resin powder at a concentration of 40% by weight or more may not exhibit sufficient performances.

(a) CRC (Water Absorption Capacity without Load)

CRC (water absorption capacity without load) of the water absorbent resin powder obtainable by the present invention is within the aforementioned range and 30 [g/g] or more, preferably 32 [g/g] or more, 34 [g/g] or more, and particularly preferably 35 [g/g] or more. When CRC is low, there is a tendency that the absorption amount of a paper diaper is lowered. An upper limit of the CRC is not particularly limited. However, considering the balance with the other physical properties (for example, resistance to urine, and liquid permeability), the upper limit is 45 [g/g] or less, 42 [g/g] or less, and preferably 40 [g/g] or less. The CRC can be appropriately controlled by crosslinking agent amount during the polymerization, and the surface crosslinking (secondary crosslinking) after the polymerization. In view of Patent Literatures 52 and 53, control can be suitably made by reducing the crosslinking agent amount during the polymerization (for example, in the range of 0.001 to 0.09% by mol relative to monomer), using a water soluble chain transfer agent (preferably, an inorganic phosphorus-based reducing agent) (for example, in the range of 0.001 to 1% by mol relative to monomer), or the like. Preferred examples of the chain transfer agent are disclosed in International Publication No. WO 2005/027986 pamphlet, and the disclosures are considered as the disclosure of the present application.

(b) AAP (Absorption Against Pressure)

In order to prevent leakage in paper diapers, the water absorbent resin powder obtainable by the present invention has, under a load of 2.06 kPa or 4.8 kPa (preferably 4.8 kPa), AAP (AAP 0.7) of 10 [g/g] or more, 13 [g/g] or more, 16 [g/g] or more, preferably 20 [g/g] or more, more preferably 22 [g/g] or more, and still more preferably 24 [g/g] or more, as an exemplary means for achieving the polymerization and surface crosslinking described above. When it is defined under 2.06 kPa, it is preferably the aforementioned range 20 [g/g] or more, more preferably 22 [g/g] or more, 24 [g/g], and further 26 [g/g] or more, 28 [g/g] or more, and preferably 30 [g/g] or more.

An upper limit of the AAP is not particularly limited. However, considering a balance with the other physical properties, the upper limit is 28 [g/g] or less, and preferably 26 [g/g] or less under the load of 4.8 kPa (AAP 0.7). Further, it is preferably 35 [g/g] or less, more preferably 30 [g/g] or less, and still more preferably 28 [g/g] or less under the load of 2.06 kPa (AAP 0.3).

The water absorbent resin powder according to the present invention has the water absorption capacity under load (AAP 0.3) of 20 to 35 [g/g] and water absorption capacity under load (AAP 0.7) of 10 to 28 [g/g], and they are selected within the aforementioned range. Meanwhile, as the water absorption capacity under load depends on load, it is such that water absorption capacity under load (AAP 0.3)>water absorption capacity under load (AAP 0.7) and the ratio is in the range of 0.3 to 0.95 times or so. Meanwhile, the AAP 0.7 can be improved by surface crosslinking after particle size control, and by performing the surface crosslinking until it is within the aforementioned range, not only the novel water absorbent resin powder of the present invention can be obtained but also AAP or liquid permeability (SFC) can be enhanced in a state in which the water absorbent speed (FSR) is maintained.

Meanwhile, the AAP can be improved by surface crosslinking after particle size control, and by performing the surface crosslinking until it is within the aforementioned range, not only the novel water absorbent resin powder of the present invention can be obtained but also liquid permeability (SFC) can be enhanced in a state in which the water absorbent speed (FSR) is maintained.

(c) Residual Monomers

Residual monomers of the water absorbent resin powder obtainable by the present invention are controlled to be normally 500 ppm or less, preferably in a range of 0 to 400 ppm, more preferably in a range of 0 to 300 ppm, and particularly preferably in a range of 0 to 200 ppm, as an exemplary means for achieving the polymerization, from the viewpoint of safety. The residual monomers can be appropriately controlled by a polymerization initiator during the polymerization, drying conditions for the gel-crushing after the polymerization described below, or by use of the reducing agent (see, Patent Literature 51). Further, controlling the amount of a polymerization inhibitor (in particular, amount of p-methoxyphenol) during polymerization or amount of Fe to be within the aforementioned range is also a preferred way.

(d) Degradable Soluble Component

The water absorbent resin powder according to the present invention has a degradable soluble component (0.05% L-A (saline) for 2 hours/60° C., one hour extraction rinse/room temperature) of preferably 40% by weight or less, further 30% by weight or less, 25% by weight or less, 23% by weight or less, or 20% by weight or less. When the degradable soluble component is more than 40% by weight, gel deterioration caused by urine progresses during use of a paper diaper, serving as a cause of leakage or reversion. For controlling the degradable soluble component, use of the chelating agent, or use of the reducing agent, in particular use of them in combination is preferable. Use of a chain transfer agent during polymerization is also a preferred method, and it is suitably used, or used in combination with the chelating agent.

Lower limit of the degradable soluble component is preferably as low as possible. However, even when a chelating agent is used, it is required to reduce the water absorption capacity (CRC) for lowering the degradable soluble component, and from the viewpoint of the balance with high CRC, it is sufficient to have 5% by weight, or further 10% by weight. When the degradable soluble component or an increase amount of the degradable soluble component (=difference between the degradable soluble component and 16 hour soluble component) is higher than 40% by weight, stability against body fluid such as urine is insufficient, and when the absorbent body is used for actual application for a long period of time, sufficient water absorption performance cannot be exhibited.

In general, the degradable soluble component depends on a crosslinked structure of the water absorbent resin powder. When there is a compact crosslinked structure, there is a tendency that the degradable soluble component is reduced but the water absorption capacity (CRC) increases. In the present invention, it was found that the amount of the degradable soluble component can be controlled to a pre-determined range also by controlling the crosslinked structure of the water absorbent resin powder, that is, an amount of an internal crosslinking agent during the polymerization step.

In the present invention, a water absorbent resin powder having a small increase amount of the degradable soluble component is obtained, and thus an increase in soluble component is small even under the deterioration condition described below (L-ascorbic acid). As a result, stable absorption is exhibited with the type of urine (change in an amount of deteriorating component such as L-ascorbic acid). Increase amount of the degradable soluble component is preferably 40% or less, and also preferably 30% or less, 20% or less, 10% or less, or 5% or less in this order. The lower limit may also have a negative value, and it is preferably −20% or more, more preferably −10% or more, and still more preferably 0% or more. Meanwhile, having the increase amount of the degradable soluble component in the aforementioned range can be achieved by the production method of the present invention which uses a chelating agent or a reducing agent.

(e) Powder Blocking Ratio After Moisture Absorption Test

Powder blocking ratio after moisture absorption test is preferably 0 to 30% by weight, more preferably 0 to 20% by weight, still more preferably 0 to 10% by weight, and particularly preferably 0 to 5% by weight. Powder blocking ratio after moisture absorption test is measured by the method described in Examples given below.

When blocking ratio against moisture absorption is 30% by weight or less, flowability of powder is good when a paper diaper or the like is produced, and thus it becomes easy to produce a paper diaper. The powder blocking ratio is achieved by use of the (2-3) water-insoluble inorganic microparticles or other surfactants.

That is, the powder flowability after moisture absorption test (anti-caking property) is preferably 70 to 100% by weight, more preferably 80 to 100% by weight, still more preferably 90 to 100% by weight, and particularly preferably 95 to 100% by weight. "Powder flowability after moisture absorption test" is calculated by subtracting "powder blocking ratio after moisture absorption test" from 100% by weight.

(f) Particle Size

From the viewpoint of enhancing physical properties of the water absorbent resin powder obtained from the present invention, the weight average particle diameter (D50) of the water absorbent resin particle after classification is preferably 300 to 500 μm, more preferably 320 to 500 μm, and still more preferably 350 to 450 μm. Further, fine particles passable through a sieve with 150 μm mesh (JIS standard sieve) are preferably as little as possible, and relative to the entire water absorbent resin particles, it is preferably 0 to 5% by weight, more preferably 0 to 3% by weight, and still more preferably 0 to 1% by weight. Further, coarse particles non-passable through a sieve with 850 μm mesh or more (or 710 μm or more) (JIS standard sieve) are also preferably as little as possible, and relative to the entire water absorbent resin particles, it is preferably 0 to 5% by weight, more preferably 0 to 3% by weight, and still more preferably 0 to 1% by weight. Further, in the present invention, the ratio of the particles having a particle diameter of from 150 μm to less than 850 μm, or from 150 μm to less than 710 μm is controlled to preferably 95% by weight or more, and more preferably 98% by weight or more (upper limit is 100% by weight) relative to the entire water absorbent resin particles. The logarithmic standard deviation ($\sigma\zeta$) of the particle size distribution is preferably 0.20 to 0.50, more preferably 0.25 to 0.50, still more preferably 0.25 to 0.45, and particularly preferably 0.30 to 0.40.

The particle size is suitably controlled by polymerization, pulverizing, classification, granulation, or recovery of fine powder, and by preferably containing granulated particles or recycled fine powder in the water absorbent resin powder of the present invention (for example, 1 to 30% by weight of the total is recycled as fine powder), the water absorbent speed is increased and the particle size can be also controlled. Granulation can be confirmed based on an electron microscopic image or particle size shift caused by impact, in view of U.S. Pat. No. 7,473,470.

Preferably, according to granulation, average particle diameter of the water absorbent resin powder of the present invention is increased by 1.01 to 2 times, 1.05 to 1.5 times, or 1.08 to 1.3 times the particle diameter before the granulation, and it is also increased by the range of 10 to 300 μm or 20 μm to 100 μm.

Particle size is measured by the same method as one described in "(1) Average Particle Diameter and Distribution of Particle Diameter" in page 7, lines 25 through 43 in the specification of EP No. 0349240 (more specifically, EP No. 1594556 B). Meanwhile, a standard sieve (mesh) to be used for particle size measurement can be added as appropriate in accordance with a particle size of a target to be measured. For example, standard sieves having respective mesh sizes of, for example, 710 μm, 600 μm or the like can be added in view of EP No. 1594556 B. The particle size before the surface crosslinking is preferably also applied to the particle size after the surface crosslinking and also to a final product. In other words, the aforementioned particles size is also applicable to the water absorbent resin powder according to the present invention.

(g) Ext (Water Soluble Component)

Ext (water soluble component/ERT 410.02-02) of the water absorbent resin powder obtained from the present invention is, to prevent stickiness or the like during use of a paper diaper under the influence of eluted liquid portion, preferably 35% by weight or less, more preferably 25% by weight or less, 20% by weight or less, stll more preferably 15% by weight or less, and particularly preferably 10% by weight or less. The Ext can be suitably controlled by increasing the amount of crosslinking agent during polymerization and the amount of water soluble component during gel-crushing thereafter. Meanwhile, since lowering the water soluble component generally causes a decrease in the water absorption capacity (CRC) or a decrease in productivity, it is sufficient to have the lower limit of 10% by weight (or 13% by weight, or further 15% by weight). Thus, from the viewpoint of the balance, it may be in the range of 10 to 35% by weight, 10 to 25% by weight, or 10 to 20% by weight. Further, the lower limit may be 13% by weight or 15% by weight.

(h) Moisture Content

Moisture content (%) in the water absorbent resin powder obtained from the present invention is controlled to the range of 0.1 to 15% by weight, 0.5 to 10% by weight, or 1 to 8% by weight. When the moisture content is excessively low, the water absorbent resin powder is inferior in terms of anti-impact stability or dust prevention. On the other hand, when the moisture content is excessively high, the water absorption capacity is lowered or there is a problem like aggregation or coloration with the lapse of time. There is also an advantage that, with the moisture content at a predetermined amount, residual monomers or residual crosslinking agents are lowered during storage or use of a reducing agent.

(i) Water Absorbent Speed

From the viewpoint of water absorption by a paper diaper, FSR (International Publication No. WO 2009/016055 pamphlet) as water absorbent speed is 0.20 [g/g/s] or more, 0.25 [g/g/s] or more, 0.30 [g/g/s] or more, 0.32 [g/g/s] or more, 0.35 [g/g/s] or more, or 0.37 [g/g/s] or more. From the viewpoint of the balance with other physical properties, upper limit of FSR is 2.0 [g/g/s] or less, or further 1.0 [g/g/s] or so. Vortex water absorbent speed is also 90 seconds or less, 60 seconds or less, or 40 seconds or less, and the lower limit is 1 second or more, or 10 seconds or more. The water absorbent speed can be controlled by the production method of the present invention. Since a more significant effect is obtained by increasing the water absorbent speed of the present invention, increasing FSR, in particular with FSR in the aforementioned range, and in particular with FSR 0.30 [g/g/s] or more, it can be preferably applied to the method for producing the water absorbent resin powder having high water absorbent speed.

(j) "Density" (ERT 460.2-02)

"Density" as bulk density is in the range of 0.58 [g/cm$^3$] or more, 0.60 to 0.85 [g/cm$^3$], 0.61 to 0.80 [g/cm$^3$], or 0.62 to 0.78 [g/cm$^3$] by controlling internal gas bubbles ratio of the present invention. By increasing the bulk density, cost relating to transport or storage can be reduced due to compacting, and also the liquid permeability can be enhanced.

(k) Surface Tension

When surface tension is excessively low, Re-Wet is increased in a paper diaper. Thus, the surface tension defined in U.S. Pat. No. 7,473,739 is controlled at a high value, that is, 64 [N/m] or higher, 66 [N/m] or higher, 68 [N/m] or higher, and 70 [N/m] or higher in the order. The upper limit is generally 75 [N/m] or so, and the control can be made by not using a surfactant, reducing its amount, or the like.

(1) Initial Color Hue (Other Name: Initial Coloration)

The water absorbent resin powder according to the present invention can be preferably used as a hygienic material such as paper diaper, and thus it is preferably a white powder. Preferably, YI (Yellow Index) value is 0 to 25, and more preferably 0 to 10 from the viewpoint of clean feel. Meanwhile, initial color hue means color hue after production of the water absorbent resin powder, and it generally corresponds to the color hue measured before factory shipment. Further, for storage under an atmosphere of 30° C. or lower and relative humidity of 50% RH, for example, it indicates the value measured within a year after production.

(m) Color Hue with the Lapse of Time (Other Name: Coloration with the Lapse of Time)

The water absorbent resin powder according to the present invention can be preferably used as a hygienic material such as a paper diaper, and thus it is preferable to maintain it in a significantly clean and white state even in a long term storage state under high humidity or temperature condition. The long term storage state can be determined as follows, as an accelerated test for color stability after long term storage, the water absorbent resin powder is exposed for 7 days to an atmosphere with the temperature of 70±1° C. and relative humidity of 65±1% RH, and YI (Yellow Index) value of the water absorbent resin powder is measured including the examples shown below. The water absorbent resin powder according to the present invention has YI value of preferably 0 to 50, and more preferably 0 to 30 after the accelerated test for color stability after long term storage.

Meanwhile, the YI (Yellow Index) value can be measured by the method described in the Examples given below.

(2-9) Techniques of Related Art

Patent Literature 51 (International Publication No. WO 2011/040530 pamphlet) discloses combined use of a chelating agent and a reducing agent for preventing coloration and additionally discloses inorganic microparticles, methoxyphenol, and moisture content. However, a specific internal gas bubbles ratio or the control method of the present invention is not disclosed.

In Patent Literature 52 (International Publication No. WO 2011/078298 pamphlet), which is a unpublished prior application at the priority date of the present application, discloses a water absorbent resin powder with a internal gas bubbles ratio of 2.8 to 6.6% by specific foaming polymerization for the water absorbent speed and liquid permeability (claim 32, Table 3, or the like), and a water absorbent resin powder with a internal gas bubbles ratio of 0.60% or 1.21% is disclosed as a conventional product (commercially available product) in Comparative examples 17 and 18. However, the water absorbent resin powder with a internal gas bubbles ratio of 0.1 to 2.5% (preferably, containing inorganic microparticles), which is based on the control method of the internal gas bubbles ratio of the present invention, is not disclosed.

Patent Literature 52 discloses a water absorbent resin powder with internal gas bubbles ratio of 2.8 to 6.6%. However, the water absorbent resin powder with various physical properties as defined in the present invention and internal gas bubbles ratio of 0.1 to 2.5% of the present invention are not disclosed. In the present invention, the internal gas bubbles ratio is controlled to a lower level than Patent Literature 52 and also the water absorption capacity (CRC) after surface crosslinking is increased so that impact resistance and water absorption performance of a paper diaper are improved.

In Patent Literature 53 (International Publication No. WO 2011/126079 pamphlet), which is a unpublished prior application at the priority date of the present application, discloses a water absorbent resin powder with a internal gas bubbles ratio of 0.1 to 2.5% by specific gel-crushing (claim 21, Table 3, or the like). However, use of methoxyphenol is not disclosed and a water absorbent resin powder with a internal gas bubbles ratio of 0.7 to 2.5% which contains p-methoxyphenol (MQ) or inorganic microparticles is not disclosed. According to the present invention, by additionally using p-methoxyphenol (MQ) to Patent Literature 52, weather resistance is improved and, by increasing the water absorption capacity (CRC) after surface crosslinking, water absorption performance of a paper diaper is improved.

Further, foaming polymerization of a water absorbent resin for increasing water absorbent speed has been conventionally known in Patent Literature 18 to 35 or the like. However, with the conventional foaming polymerization represented by Patent Literature 45 (U.S. Patent No. 61/007,358), Comparative example 8 of the present invention or the like, it was difficult to control the internal gas bubbles ratio. Accordingly, it was more than 6.6% to contain an excess amount of closed-cells or, a large amount of a surfactant (for example, 0.1 to 10% by weight) is used for foaming like Patent Literatures 43 and 44, and thus the obtained water absorbent resin powder had lower surface tension (in particular, less than 60 [mN/m] or less than 55 [mN/m]) or there was a problem of having fine dust (in particular, 10% by weight or more) due to excessive foaming.

Further, in Non-Patent Literature 1, pages 197 to 199 and Table 5.6, regarding a commercially available (polyacrylic acid-based) water absorbent resin (5 types), BET surface area, water absorbent speed, water absorption capacity, bulk specific gravity, and apparent density are disclosed for a 40 to 60 mesh-Cut (powder with upper and lower limit of 425 to 250 µm) product.

Non-Patent Literature 1 discloses that, as a specific number of apparent density measured by a methanol wet method, 1.500 [g/cm$^3$] for Product Name Arasorb720 (Arakawa Chemical Industries Ltd.) and Sanwet 1M-1000 (Sanyo Chemical Industries Ltd.); 1.250 [g/cm$^3$] for Aridall 1078 (American Colloid Company), 1.667 [g/cm$^3$] for Aquakeep (Sumitomo Seika Chemicals Co. Ltd.) and DryTech510 (Dow Chemicals Co., Ltd). That is, Non-Patent Literature 1 discloses five commercially available water absorbent resin with apparent densities in a range of 1.250 to 1.667 [g/cm$^3$]. Specifically, apparent density (methanol wet method) having been subjected to 40 to 60 mesh-cut in Non-Patent Literature 1 is different from the dry density measured for the whole particle size in the present invention. Further, Non-Patent Literature 1 does not provide the true density or the chemical composition of each. Assuming that Aquakeep (reverse-phase suspension polymerization, spherical particles) has a true density of 1.667 [g/cm$^3$] which is substantially a true density, and all the five commercially available water absorbent resins listed in Table 5.6 have the same chemical composition, the internal gas bubbles ratio of the commercially available water absorbent resins (Table 5.6) can be divided into a type having a internal gas bubbles ratio of 0% or close to 0% (Aquakeep, DryTech510) and another type having a internal gas bubbles ratio approximately in a range of 10% to 25% (Arasorb720, Sanwet 1M-1000, Aridall 1078). On the other hand, the present invention is characterized in that the internal gas bubbles ratio (2.8% to 6.6%) and the particle size (the ratio of the particles with particle sizes within 850 µm to 150 µm is 95% by weight or more) are controlled within the particular narrow ranges.

Moreover, Patent Literature 31 (U.S. Pat. No. 5,856,370) does not disclose the particular internal gas bubbles ratio of 0.1 to 2.5% and particle size of the present invention, while it discloses a porous water absorbent resin obtained by using an azo compound so as to attain a density of more than 1.0 [g/cm$^3$] in a dry state and a density of 1.0 [g/cm$^3$] in a swollen state (wherein the density when swollen is measured by using a pycnometer).

With a water absorbent resin which is not disclosed in Patent Literatures 1 to 50, in particular Patent Literatures 51 to 53, both coloration and water absorbent speed are obtained in the present invention.

Further, in the examples of Patent Literatures 52 and 53, there is a large amount of polyethylene glycol diacrylate as an internal crosslinking agent in the polymerization step, and the water absorbent resin powder having little amount of degradable soluble component like the present invention is not disclosed.

[3] Method for Producing Polyacrylic Acid (Salt)-Based Water Absorbent Resin Powder The method for producing a polyacrylic acid (salt)-based water absorbent resin powder according to an embodiment of the present invention (a first method) is a method for producing a water absorbent resin powder which has internal gas bubbles ratio of 0.1% to 2.5% as specified by the following equation, in which the method includes steps of performing foaming polymerization or boiling polymerization of an aqueous monomer solution including p-methoxyphenol and also acrylic acid as a main component, kneading and grain refining a water-containing gel-like polymer having gas bubbles obtained from the polymerization, drying after gel-crushing, and surface crosslinking the pulverized and classified product with internal gas bubbles ratio 0.1% to 2.5% to have the water absorption capacity without load (CRC) of 30 [g/g] to 45 [g/g], the water absorption capacity under load (AAP 0.3) of 20 [g/g] to 35 [g/g], and the water absorption capacity under load (AAP 0.7) of 10 [g/g] to 28 [g/g].

$$(\text{internal gas bubbles ratio})[\%]=\{(\text{True density})(\text{Apparent density})\}/(\text{True density})\times 100$$

Further, the method for producing a polyacrylic acid (salt)-based water absorbent resin powder of the present invention (a second method) provides a method for producing a water absorbent resin powder which has internal gas bubbles ratio of 0.1% to 2.5% as specified by the following equation, in which the method includes steps of performing foaming polymerization or boiling polymerization of an aqueous monomer solution containing p-methoxyphenol and also acrylic acid as a main component, obtaining a water absorbent resin which contains p-methoxyphenol and has internal gas bubbles ratio of 0.1% to 2.5%, adding a chelating agent during the polymerization or after the polymerization, and adjusting to have the water absorption capacity without load (CRC) of 30 [g/g] to 45 [g/g], the water absorption capacity under load (AAP 0.3) of 20 [g/g] to 35 [g/g] and the water absorption capacity under load (AAP 0.7) of 10 [g/g] to 28 [g/g].

$$(\text{internal gas bubbles ratio})[\%]=\{(\text{True density})-(\text{Apparent density})\}/(\text{True density})\times 100$$

Preferably, it additionally includes inorganic microparticles. The step for obtaining a water absorbent resin powder with internal gas bubbles ratio of 0.1 to 2.5%, preferably includes polymerization and gel-crushing described below.

From the viewpoint of the water absorption capacity, according to both the first method and the second method, soluble component of the water adsorbent resin powder is preferably 40% by weight or less, 30% by weight or less, and 20% by weight or less. The lower limit of about 10% by weight or so is sufficient. Fe ion amount in the monomer is preferably 3 ppm or less, and more preferably 0.1 to 3 ppm. Further, an inorganic reducing agent is blended in, and a polyvalent metal ion is additionally blended in. Also preferably, a chelating agent and water-insoluble inorganic microparticles are used in combination.

Hereinafter, each step will be described.

(3-1) Polymerization Step

The present step is a step of polymerizing an aqueous solution containing acrylic acid (salt) as a main component to obtain a water-containing gel-like crosslinked polymer (hereinafter, it may be also referred to as "hydrogel" or "water-containing gel-like polymer"). Specifically, the present step is a step of performing foaming polymerization or boiling polymerization of an aqueous monomer solution containing p-methoxyphenol and acrylic acid (salt) as a main component. Meanwhile, the boiling polymerization indicates polymerization via 100° C. or higher, which is boiling temperature of water as a polymerization solvent (in particular, boiling under polymerization heat), and the foaming polymerization indicates polymerization including having or generating gas bubbles in a polymer or a monomer at the time of polymerization or during polymerization (for example, using a foaming agent for monomer or dispersing inert gas). Preferred examples of the polymerization method include the method of prior application • Patent Literatures 52 and 53.

(Monomer)

The water absorbent resin powder obtained by the present invention uses, as a raw material (monomer), a monomer containing acrylic acid (salt) as a main component, which is generally polymerized in an aqueous solution state. Concentration of the monomer in an aqueous monomer solution is preferably 10 to 80% by weight, more preferably 20 to 80% by weight, still more preferably 30 to 70% by weight, further still more preferably 40 to 60% by weight, and particularly preferably 30 to 55% by weight.

Further, it is preferable from the viewpoint of the water absorption performance and residual monomers that the hydrogel obtained by the polymerization of the aqueous monomer solution have acid groups, at least some of which are neutralized. Such partial neutralization salt is not limited to a specific one but is, from the viewpoint of the water absorption performance, preferably monovalent salt selected from a group consisting of alkali metal salt, ammonium salt, and amine salt, more preferably alkali metal salt, still more preferably alkali metal salt selected from a group consisting of sodium salt, lithium salt, and potassium salt, and particularly preferably sodium salt. Therefore, a basic substance to be used for such neutralization is not limited to a specific one but is preferably a monovalent basic substance such as a hydroxide of alkali metal including sodium hydroxide, potassium hydroxide, lithium hydroxide, and the like or (hydrogen) carbonate such as sodium (hydrogen) carbonate or potassium (hydrogen) carbonate, and particularly preferably sodium hydroxide.

The neutralization can be carried out in various ways and under various conditions before, during, and after the polymerization. For example, hydrogel obtained by polymerizing unneutralized or low-neutralized (for example, from 0 to 30% by mol) acrylic acid can be neutralized, particularly neutralized simultaneously with gel-crushing. It is, however, preferable from the viewpoint of improvement in productivity, physical properties, and the like that unpolymerized acrylic acid be neutralized. That is, it is preferable that neutralized acrylic acid (partial neutralization salt of acrylic acid) be used as a monomer.

A neutralization rate at the neutralization is not limited to a specific one but is, as a final water absorbent resin powder, preferably 10% by mol to 100% by mol, more preferably 30% by mol to 95% by mol, still more preferably 45% by mol to 90% by mol, and particularly preferably 60% by mol to 80% by mol. Temperature of the neutralization is neither limited to a specific one but is preferably 10° C. to 100° C., and more preferably 30° C. to 90° C.

In order to improve physical properties of the water absorbent resin powder to be produced in the present invention, it is possible to add an arbitrary component such as a water soluble resin or a water absorbent resin including starch, cellulose, polyvinyl alcohol (PVA), polyacrylic acid (salt), polyethyleneimine and the like, a foaming agent including carbonate, an azo compound, gas bubble and the like, a surfactant, or an additive, to the aqueous monomer solution, the hydrogel, a dried polymer, the water absorbent resin, and the like in any step of a production process of the present invention. In a case where the water soluble resin or the water absorbent resin is added, an amount of the arbitrary component is preferably 0 to 50% by weight, more preferably 0 to 20% by weight, still more preferably 0 to 10% by weight, and particularly preferably 0 to 3% by weight relative to monomer. In a case where the foaming agent, the surfactant, or the additive is added, it is preferably 0 to 5% by weight, and more preferably 0 to 1% by weight. Note that a graft polymer or a water absorbent resin composition can be obtained by addition of the water soluble resin or the water absorbent resin. A polymer of starch and acrylic acid, a polymer of PVA and acrylic acid, and the like are also regarded as polyacrylic acid (salt)-based water absorbent resin powder in the present invention.

Further, in the present invention, in a case where acrylic acid (salt) is employed as a main component, a hydrophilic or hydrophobic unsaturated monomer(s) (hereinafter, referred to as "other monomer") other than the acrylic acid (salt) may be used in combination with the acrylic acid (salt). Such other monomer is not limited to a specific one. Examples of the other monomer encompass methacrylic acid, (anhydrous) maleic acid, 2-(meth)acrylamide-2-methyl propanesulfonic acid, (meth)acryloxyalkanesulfonic acid, N-vinyl-2-pyrolidone, N-vinylacetamide, (meth)acrylamide, N-isopropyl (meth)acrylamide, N,N-dimethyl(meth)acrylamide, 2-hydroxyethyl(meth)acrylate, methoxypolyethylene glycol (meth)acrylate, polyethylene glycol (meth)acrylate, stearyl acrylate, salts thereof, and the like. An amount of the other monomer to be used is suitably determined, and is preferably, but not limited to, 0 to 50% by mol, more preferably 0 to 30% by mol, and still more preferably 0 to 10% by mol relative to the total monomer.

(Internal Crosslinking Agent)

It is preferable from the viewpoint of the water absorption performance of the water absorbent resin powder to be produced in the present invention that a crosslinking agent (hereinafter, may be referred to as an "internal crosslinking agent") be used. The internal crosslinking agent is not limited to a specific one. Examples of the internal crosslinking agent encompass a polymerizable crosslinking agent, which is polymerizable with acrylic acid, a reactive crosslinking agent which is reactive with a carboxyl group, a crosslinking agent which is polymerizable with acrylic acid and reactive with a carboxyl group, and the like.

Examples of the polymerizable crosslinking agent encompass compounds each having at least two polymerizable double bonds in a molecule, such as N,N'-methylene bisacrylamide, (poly)ethylene glycol di(meth)acrylate, (polyoxyethylene)trimethylolpropane tri(meth)acrylate, and poly(meth)allyloxy alkanes. Examples of the reactive crosslinking agent encompass a covalent bonding crosslinking agent such as polyglycidyl ether (for example, ethylene glycol diglycidyl ether) and polyvalent alcohol (for example, propanediol, glycerin, and sorbitol), and an ionic bonding crosslinking agent such as a polyvalent metal compound (for example, aluminum salt). Among these, from the viewpoint of the absorption performance, the crosslinking agent is more preferably the polymerizable crosslinking agent, which is polymerizable with acrylic acid, and particularly preferably an acrylate, allyl or acrylamide polymerizable crosslinking agent. One or more types of the internal crosslinking agents can be employed. Note that in a case where the polymerizable crosslinking agent and the covalent-bonding crosslinking agent are used in combination, a combination ratio thereof is preferably 10:1 through 1:10.

The amount of the internal crosslinking agent to be used is, from the viewpoint of the physical properties, preferably 0.001% by mol to 5% by mol, more preferably 0.002% by mol to 2% by mol, still more preferably 0.04% by mol to 1% by mol, particularly preferably 0.06% by mol to 0.5% by mol, and most preferably 0.06% by mol to 0.08% by mol relative to the total monomer excluding a crosslinking agent. Moreover, in an especially preferable embodiment of the present invention, an amount of the polymerizable crosslinking agent to be used is preferably 0.01% by mol to 1% by mol, more preferably 0.04% by mol to 0.5% by mol, still more preferably 0.05% by mol to 0.1% by mol, and particularly preferably 0.06 to 0.08% by mol.

(Polymerization Initiator)

The polymerization initiator for use in the present invention is selected as appropriate, considering how the polymerization is carried out. However, the present invention is not limited thereto. For example, a photolytic polymerization initiator, a thermally degradable polymerization initiator, a redox polymerization initiator, and the like can be exemplified. An amount of the polymerization initiator to be used is preferably 0.0001% by mol to 1% by mol, more preferably 0.0005% by mol to 1% by mol, still more preferably 0.001% by mol to 1% by mol, and particularly preferably 0.001% by mol to 0.5% by mol, relative to the monomer. In a case where the use amount of the polymerization initiator is equal to or less than 1% by mol, deterioration of a color hue of the water absorbent resin powder can be prevented. Further, when the use amount of the polymerization initiator is higher than or equal to 0.0001% by mol, an increase in residual monomers can be prevented. Further, to contain internal gas bubbles at a constant amount, a monomer with gas bubbles included therein may be used or polymerization may be carried out by using a foaming agent (for example, a water soluble azo compound, carbonate (hydrogen) salt, and ureas) or by boiling polymerization.

Examples of the photolytic polymerization initiator encompass benzoin derivative, benzyl derivative, acetophenone derivative, benzophenone derivative, azo compound, and the like. Moreover, examples of the thermally degradable polymerization initiator encompass persulfates such as sodium persulfate, potassium persulfate, and ammonium persulfate, peroxides such as hydrogen peroxide, t-butyl peroxide, and methyl-ethyl-ketone peroxide, azo compounds such as 2,2'-azobis(2-amidino propane)dihydrochloride, and 2,2'-azobis[2-(2-imidazoline 2-yl)propane] dihydrochloride, and the like.

Furthermore, examples of the redox polymerization initiator encompass mixtures having persulfate or peroxide together with a reducing compound, such as L-ascorbic acid or sodium hydrogen sulfite in combination. Moreover, it is one preferable embodiment to use the above-mentioned photolytic polymerization initiator and thermally degradable polymerization initiator in combination.

(Polymerization Method)

Particulated hydrogel can be obtained by spraying droplet polymerization or reverse-phase suspension polymerization in the method for producing the water absorbent resin powder of the present invention. Meanwhile, from the viewpoint of the liquid permeability (SFC) and the water absorbent speed (FSR) of the water absorbent resin powder to be obtained, in order to easily control the polymerization, and the like, aqueous solution polymerization is carried out. The aqueous solution polymerization can be tank-type (silo-type) un-stirring polymerization but preferably kneader polymerization or belt polymerization, more preferably continuous aqueous solution polymerization, still more preferably high-concentration continuous aqueous solution polymerization, and particularly preferably high-concentration high-temperature starting continuous aqueous solution polymerization. Note here that what is meant by stirring polymerization is polymerizing carried out under stirring of the hydrogel, especially under stirring and grain refining of the hydrogel (wherein the hydrogel is particularly hydrogel having a polymerization ratio of not less than 10% by mol, further particularly hydrogel having a polymerization ratio of not less than 50% by mol). The stirring of the aqueous monomer solution (having a polymerization ratio of from 0 to less than 10% by mol) may be carried out as appropriate before and/or after the un-stirring polymerization.

Examples of the continuous aqueous solution polymerization encompass continuous kneader polymerization (disclosed in U.S. Pat. Nos. 6,987,171, 6,710,141, and the like), and continuous belt polymerization (disclosed in U.S. Pat. Nos. 4,893,999 and 6,241,928, US Patent Application Publication No. 2005/215734, and the like). These aqueous solution polymerizations can produce the water absorbent resin powder with high productivity.

(3-2) Gel-Crushing Step

The present step is a step of kneading and grain refining the water-containing gel-like polymer with gas bubbles obtained by the polymerization. Specifically, it is a gel-crushing step of a water-containing gel-like crosslinked polymer during or after the polymerization, and according to the step, the water-containing gel-like crosslinked polymer during or after the polymerization is subjected to grain-refining to obtain a particulated water-containing gel-like crosslinked polymer (hereinafter, it may be also referred to as "particulated hydrogel").

The present step is a step of grain-refining the water-containing gel-like crosslinked polymer during or after polymerization to obtain a particulated water-containing gel-like crosslinked polymer (hereinbelow, it may be also referred to as a "particulated hydrogel"). Meanwhile, the gel-crushing step is preferably performed after the polymerization. Meanwhile, to distinguish from "pulverizing" of the pulverizing step classification step described below, the present step is referred to as "gel-crushing". Type of gel-crushing device is not particularly limited, and examples thereof include a gel crusher having a plurality of rotational stirring blades such as a batch-type or continuous double-armed kneader, a single- or twin-screw extruder, a meat chopper, particularly a screw extruder, and the like. The gel-crushing technique is described in U.S. Pat. Nos. 7,694,900, 6,565,768, 6,140,395, and the like.

(Patent Literature 53)

As for the method of controlling internal gas bubbles ratio of the present invention, the gel-crushing described in (2-2) Gel-crushing step of Patent Literature 53 (International Publication No. WO 2011/126079 pamphlet), which is a unpublished prior application on the priority date of the present application, is preferably applied, and in the present invention, for the internal gas bubbles ratio and control thereof, a production method including applying higher shear force than conventional technique and shearing to the extent such that the weight average molecular weight of the water soluble component is increased is applied.

Hereinafter, (2-2) Gel-crushing step of Patent Literature 53 can be directly applied to the present invention, and the disclosures are considered as the disclosure of the present application.

(Physical Properties of Hydrogel Before Gel-Crushing)

According to the preferred method for producing the water absorbent resin powder of the present invention (first producing method), the gel grinding energy (GGE) is controlled in a specific range. In the producing method, it is preferable to subject, to gel-crushing, a water-containing gel-like crosslinked polymer (also referred to as "polyacrylic acid (salt) crosslinked polymer"), in which at least one of which gel temperature, resin solid content, gel CRC, gel Ext, and weight average molecular weight of water soluble component is controlled in the following range.

Preferably, the water-containing gel-like crosslinked polymer with resin solid content of 10 to 80% by weight is subjected to gel-crushing which satisfies at least one of the following (1) to (4).

(1) the gel-crushing is carried out with gel grinding energy (GGE) of 18 [J/g] to 60 [J/g], (2) the gel-crushing is carried out with gel grinding energy (2) (GGE (2)) of 9 [J/g] to 40 [J/g], (3) weight average molecular weight of water soluble component of the water-containing gel-like crosslinked polymer is increased by 10,000 [Da] to 500,000 [Da], and (4) the gel-crushing is carried out until the water-containing gel-like crosslinked polymer has a weight average particle diameter (D50) of 350 μm to 2,000 μm, and logarithmic standard deviation ($\sigma\zeta$) of particle size distribution of 0.2 to 1.0.

However, in a case in which the gel-crushing so that the item (4) is met, a through-flow (belt type) dryer is used for drying and the particulated water-containing gel-like crosslinked polymer to be supplied into a through-flow (belt type) dryer has resin solid content of 10 to 80% by weight, and the through-flow belt-type dryer sends hot air at drying temperature of 150° C. to 250° C. at a wind velocity of 0.8 [m/s] to 2.5 [m/s] in a direction vertical (up-and-down direction).

Herein, the gel-crushing of the present invention essentially satisfies at least one of the items (1) through (4), preferably two or more, further three or more, and particularly all of them. Further, for the drying step, the gel-crushing is not limited to the item (4), and also for the gel-crushing of the items (1) to (3), drying by through-flow belt-type dryer and the drying condition (such as the hot air velocity) are also preferably applied. Moreover, it is still more preferable that surface crosslinking be performed especially by combination of a covalent bonding surface crosslinking agent and an ionic bonding surface crosslinking agent which is later described.

Further, in the present invention, by use of the chelating agent or reducing agent and/or control of the amount of an internal crosslinking agent, the degradable soluble component is controlled.

Specifically, the preferred method for producing a water absorbent resin powder of the present invention (first production method) is a method for producing a polyacrylic acid (salt)-based water absorbent resin powder including a polymerization step for an aqueous monomer solution containing an acrylic acid (salt)-based monomer, a gel-crushing step for water-containing gel-like crosslinked polymer (water-containing gel-like polymer) during or after the polymerization, and a drying step after the gel-crushing, in which, during the gel-crushing step, the water-containing gel-like crosslinked polymer with resin solid matter of 10 to 80% by weight is subjected to gel-crushing with gel grinding energy (GGE) of 18 to 60 [J/g], dried at drying temperature of 150 to 250° C., and again subjected to a surface treatment.

Further, according to the preferred method for producing a water absorbent resin powder of the present invention (preferred second production method), the gel grinding energy (2) (GGE (2)) is controlled in a constant range. According to the production method, water-containing gel-like crosslinked polymer (polyacrylic acid (salt)-based crosslinked polymer), in which at least one of the physical properties of gel temperature, resin solid content, gel CRC, gel Ext, and weight average molecular weight of water soluble component are controlled in the following range, is preferably subjected to gel-crushing.

Specifically, the method for producing a water absorbent resin powder of the present invention (a second production method) is a method for producing a polyacrylic acid (salt)-based water absorbent resin powder including a polymerization step for an aqueous monomer solution containing an acrylic acid (salt)-based monomer, a gel-crushing step for water-containing gel-like crosslinked polymer during or after the polymerization, and a drying step after the gel-crushing, in which, during the gel-crushing step, the water-containing gel-like crosslinked polymer with resin solid content of 10 to 80% by weight is subjected to gel-crushing with gel grinding energy (2) (GGE (2)) of 9 to 40 [J/g], dried at drying temperature of 150 to 250° C., and further subjected to a surface treatment.

As for the following (a) to (e), and descriptions of "gel crusher" to "physical properties of particulated hydrogel after gel-crushing", the publication of Patent Literature 53 (paragraphs from [0080] to [0127]) can be directly applied except "(b) Gel CRC after gel-crushing" and "(c) Gel Ext after gel-crushing", and the disclosures are considered as the disclosure of the present application ((a) Gel temperature, (b) Resin solid content, (c) Gel CRC, (d) Gel Ext, (e) Weight average molecular weight of water soluble component, (Gel crusher), (Porous dies), (Gel grinding energy (GGE)/Gel grinding energy (2) (GGE2)), (Gel-crushing region), (Operation condition of gel-crushing device), (Use of water), (Use of additives), (Physical properties of particulated hydrogel after gel-crushing)).

In the present invention, an upper limit of the gel grinding energy (GGE) for gel-crushing the hydrogel is preferably 60 [J/g] or less, more preferably 50 [J/g] or less, and still more preferably 40 [J/g] or less. A lower limit of the GGE is preferably 18 [J/g] or more, more preferably 20 [J/g] or more, and still more preferably 25 [J/g] or more. Therefore, in the present invention, the gel grinding energy (GGE) for gel-crushing the hydrogel is, for example, in a range of 18 [J/g] to 60 [J/g], preferably in a range of 20 [J/g] to 50 [J/g], and more preferably in a range of 25 [J/g] to 40 [J/g]. Controlling the GGE in the above range makes it possible to perform gel-crushing the hydrogel while applying appropriate shearing stress and compressive force to the hydrogel. Note that the gel grinding energy (GGE) is defined by including energy during idling of the gel-crushing device.

According to the present invention, the gel grinding energy (2) that excludes the energy during idling of the gel-crushing device can be defined. In other words, in the present invention, an upper limit of the gel grinding energy (2) (GGE (2)) for gel-crushing the hydrogel is preferably 40 [J/g] or less, more preferably 32 [J/g] or less, and still more preferably 25 [J/g] or less. A lower limit of the GGE (2) is preferably 9 [J/g] or more, more preferably 12 [J/g] or more, and still more preferably 15 [J/g] or more. Therefore, in the present invention, the gel grinding energy (2) (GGE (2)) for gel-crushing the hydrogel is, for example, 9 [J/g] to 40 [J/g], preferably 12

[J/g] to 32 [J/g], and more preferably 15 [J/g] to 25 [J/g]. Controlling the GGE in the above range makes it possible to perform gel-crushing the hydrogel while applying appropriate shearing stress and compressive force to the hydrogel.

Weight average molecular weight of water soluble component of hydrogel before gel-crushing is preferably in a range of 50,000 to 450,000 [Da], more preferably in a range of 100,000 to 430,000 [Da], and still more preferably in a range of 150,000 to 400,000 [Da].

Weight average molecular weight of water soluble component of higher than or equal to 50,000 [Da] results in non-excessive reduction in particle diameter of particulated hydrogel obtained after the gel-crushing, thereby making it impossible to produce the water absorbent resin powder having a desired physical property. Moreover, hydrogel having weight average molecular weight of water soluble component of equal to or less than 450,000 [Da] has enough crosslinking points, and a damage caused by shearing stress can be suppressed. This possibly prevents deterioration of properties such as increase in the water soluble component after the gel-crushing. The weight average molecular weight of the water soluble component of the hydrogel can be appropriately controlled by, for example, an amount of crosslinking agent to be added during polymerization, polymerization concentration, if necessary, a chain transfer agent, or the like.

The resin solid content in hydrogel before gel-crushing is, from the viewpoint of physical properties, 10 to 80% by weight, preferably 30 to 80% by weight, more preferably 40 to 80% by weight, still more preferably 45 to 60% by weight, and particularly preferably 50 to 60% by weight. Resin solid content of equal to or higher than 10% by weight is preferable because it may suppress an excessive increase in softness of the hydrogel. On the other hand, resin solid content of equal to or less than 80% by weight is preferable because it can suppress an excessive increase in hardness of the hydrogel, thereby making it easy to control the particle shape and the particle size distribution. The resin solid content of the hydrogel can be appropriately controlled by polymerization concentration, moisture vaporization during polymerization, addition of water absorbent resin fine powder (fine powder recycling step) to the polymerization step, if necessary, addition of water or partial drying after polymerization, or the like.

CRC (gel CRC) of hydrogel before gel-crushing is preferably 10 [g/g] to 50 [g/g], more preferably 15 [g/g] to 45 [g/g], still more preferably 15 [g/g] to 42 [g/g], and particularly preferably 15 [g/g] to 40 [g/g]. Gel CRC less than 10 [g/g] or more than 50 [g/g] is not preferable because it makes it difficult to control the particle shape and the particle size distribution during the gel-crushing. The gel CRC can be appropriately controlled by an amount of crosslinking agent to be added during polymerization, polymerization concentration, or the like. Note that it is conventionally well-known that it is preferable for a water absorbent resin powder to have a high CRC. It was, however, found in the present invention that the gel CRC more than 50 [g/g] makes it difficult to control the particle shape and the particle size distribution.

Water soluble component of hydrogel before gel-crushing (gel Ext) is preferably 0.1% by weight to 10% by weight, more preferably 0.5% by weight to 8% by weight, and still more preferably 1% by weight to 5% by weight. Gel Ext of equal to or less than 10% by weight can prevent excessive increase in weight average molecular weight of water soluble component due to shearing stress during the gel-crushing, thereby a desired liquid permeability is obtained.

In a case where the gel-crushing device used in the gel-crushing step of the present invention is a screw extruder, the number of revolutions of a screw axis of the screw extruder cannot be simply defined. This is because a rate of a periphery of a rotational blade varies depending on an internal diameter of a cylindrical body (casing) of the screw extruder. However, the number of revolutions of the axis is preferably in a range of 90 rpm to 500 rpm, more preferably in a range of 100 rpm to 400 rpm, and still more preferably in a range of 120 rpm to 200 rpm. The number of revolutions of the axis of equal to or greater than 90 rpm is preferable because shearing stress and compressive force required for the gel-crushing can be obtained. The number of revolutions of the axis of equal to or lower than 500 rpm is also preferable because no excessive shearing stress and compressive force is applied to the hydrogel so that a decrease in physical properties can be suppressed and breaking or the like caused by high load applied to a gel crusher can be prevented.

Further, the preferred method for producing the water absorbent resin powder of the present invention (fourth producing method) is carried out such that the particulated hydrogel thus obtained by the gel-crushing has a weight average particle diameter (D50) of 350 μm to 2000 μm, logarithmic standard deviation (σζ) of particle size distribution of 0.2 to 1.0, and resin solid content of 10% by weight to 80% by weight.

That is, in order to attain the object of the present invention, the method for producing water absorbent resin powder of the present invention (a fourth producing method) is a method for producing a polyacrylic acid (salt)-based water absorbent resin powder including the steps of polymerizing an acrylic acid (salt)-based aqueous monomer solution, performing gel-crushing of a water-containing gel-like crosslinked polymer during or after the polymerization step, and drying after the gel-crushing, in which particulated water-containing gel-like crosslinked polymer obtained by the gel-crushing has a weight average particle diameter (D50) of 350 μm to 2,000 μm and logarithmic standard deviation (σζ) of particle size distribution of 0.2 to 1.0, the particulated water-containing gel-like polymer to be supplied into the through-flow belt-type dryer in the drying step has resin solid content of 10% by weight to 80% by weight, drying temperature is 150° C. to 250° C. and wind velocity is 0.8 [m/s] to 2.5 [m/s] in a vertical direction in a through-flow belt-type dryer, and a step of carrying out a surface treatment is additionally included.

As for the following (a) to (e), and descriptions of "gel crusher" to "physical properties of particulated hydrogel after gel-crushing", the publication of Patent Literature 53 (paragraphs from [0080] to [0127]) can be directly applied, and the disclosures are considered as the disclosure of the present application ((a) Particle size, (b) Gel CRC after gel-crushing, (c) Gel Ext after gel-crushing, (d) Weight average molecular weight of water soluble component after gel-crushing, and (e) Resin solid content after gel-crushing).

(Number of Measurement Point)

For the measurement of the physical properties of the hydrogel before the gel-crushing, or the physical properties of the particulated hydrogel after the gel-crushing, it is necessary to perform the measurement by sampling and measuring at a necessary frequency and a necessary amount in a production device. In the present invention, the measurement is carried out on the basis of the weight average molecular weight of the water soluble component of the hydrogel before the gel-crushing. It is necessary that the value should be a numeric value that is sufficiently averaged. For this reason, in order to calculate the numeric value, for example, the following sampling and measurement are carried out. In a case where the water absorbent resin powder is produced by 1 [t/hr] to [t/hr], or 1 [t/hr] to 10 [t/hr] by use of a continuous gel-crushing device such as a continuous kneader or a meat chopper, two or more points relative to 100 kg of the hydrogel, at least ten or more points in total are sampled and measured. In a case of batch-type gel-crushing (such as a batch-type kneader), at least ten or more points are sampled from a batch sample, and measured. The physical properties of the particulated hydrogel are estimated on the basis of the sampling and the measurement.

(3-3) Drying Step (Heating and Drying Step)

Examples of the drying method in the drying step of the present invention encompass heat drying, hot air drying, drying under reduced pressure, infrared drying, microwave drying, drying by use of a drum dryer, drying by azeotropic dehydration with a hydrophobic organic solvent, high humidity drying with use of high temperature water vapor, and the like. Among the drying methods, the hot air drying, particularly with a dew point of 40° C. to 100° C., more preferably a dew point of 50° C. to 90° C., is preferably adopted.

Drying temperature in the drying step of the present invention is in a range of 150° C. to 250° C., preferably in a range of 160° C. to 220° C., and more preferably in a range of 170° C. to 200° C. A drying temperature in the range of 150° C. to 250° C. makes it possible to reduce drying time and coloration of the dried polymer to be produced. Further, such a drying temperature tends to bring an effect of improving the permeability potential and the water absorbent speed of the water absorbent resin powder thus obtained. Meanwhile, a drying temperature of equal to or lower than 250° C. can prevent damage on a polymer chain, thereby exhibiting a tendency of improving the physical properties. Moreover, a drying temperature of equal to or higher than 150° C. yields an increase in the water absorbent speed, and thus can prevent clogging caused by production of non-dried products during a subsequent pulverizing step.

(Drying Time)

Drying time in the drying step of the present invention depends on a surface area of the particulated hydrogel, types of a dryer, and the like, and may be appropriately determined so that an objective moisture content is attained. However, the drying time is preferably in a range of 1 minute to 10 hours, more preferably in a range of 5 minutes to 2 hours, still more preferably in a range of 10 minutes to 120 minutes, and particularly preferably in a range of 20 minutes to 60 minutes.

(Wind Velocity)

With regard to the drying step of the present invention, in order to achieve the object of the present invention, the through-flow dryer, especially the belt-type dryer sends hot air in the vertical direction (up-and-down direction) with a wind velocity of 0.8 [m/s] to 2.5 [m/s], preferably 1.0 [m/s] to 2.0 [m/s]. The wind velocity in the above range makes it possible not only to control the moisture content of the dried polymer thus obtained to be in a desired range but also to improve the water absorbent speed. It was found that the wind velocity of equal to or higher than 0.8 [m/s] can prevent extension of the drying time, thereby can prevent deterioration of the water absorbent speed. It was also found that the wind velocity of equal to or less than 2.5 [m/s] can keep the particulated hydrogel from being blown up during drying, thereby enabling stable drying.

(3-4) Pulverizing Step and Classification Step

The present step is a step of obtaining water absorbent resin particles by pulverizing • classifying the dry polymer (dried product) obtained from the drying step. Preferably, pulverizing • classifying are performed until that the water absorbent resin particles after pulverizing • classifying have a particle size described in the above (2-8) (f).

(Internal Gas Bubbles Ratio)

The water absorbent resin powder of the present invention obtained by gel-crushing, more preferably by drying at specific temperature and wind velocity may have a specific internal gas bubbles ratio. The internal gas bubbles ratio of the water absorbent resin powder and preferred range thereof are described in the above (2-1), and the same applies to a water absorbent resin particles that are obtained by the pulverizing • classifying. Specifically, according to the water absorbent resin particles before surface crosslinking, it is preferable that ratio of the particle having a particle diameter of equal to or more than 150 μm but less than 850 μm is 95% by weight or higher, the logarithmic standard deviation ($\sigma\zeta$) of the particle size distribution is 0.25 to 0.50, and the internal gas bubbles ratio as defined by the following equation is 0.1 to 2.5%. The lower limit of internal gas bubbles ratio is, within the above range, is 0.2% or more, 0.3% or more, 0.5% or more, 0.7% or more, or 0.8% or more, which is more preferable in that order. Further, the upper limit of internal gas bubbles ratio is, within the above range, is 2.0% or less, 1.7% or less, 1.5% or less, 1.3% or less, or 1.2% or less, which is more preferable in that order. For example, the internal gas bubbles ratio is preferably 0.2 to 2.0%, more preferably 0.3 to 1.7%, still more preferably 0.5 to 1.5%, and most preferably 0.8 to 1.2%.

By performing surface crosslinking the water absorbent resin particles having the aforementioned internal gas bubbles ratio or particle size distribution, in particular, performing surface crosslinking until water absorption capacity under load (AAP 0.3) becomes 20 [g/g] or more, the water absorbent resin powder with improved water absorbent speed (FSR) can be provided, and thus the object of the invention can be achieved. When the internal gas bubbles ratio is excessively high, an anti-damaging property after surface crosslinking is lowered so that the physical properties are deteriorated due to disrupted particle surface during the production step thereafter or actual application (for example, production of a paper diaper), dust or fine dust is generated, or it is disadvantageous in terms of shipping cost as the bulk specific gravity of the water absorbent resin powder is lowered.

$$(\text{internal gas bubbles ratio})[\%] = \{(\text{True density}) - (\text{Apparent density})\}/(\text{True density}) \times 100$$

Meanwhile, the water absorbent resin particles before surface crosslinking are not limited by the above internal gas bubbles ratio or particle size distribution. Hereinafter, the surface crosslinking of the present invention will be described.

(3-5) Surface Treatment Step

The method for producing the polyacrylic acid (salt)-based water absorbent resin powder according to the present invention preferably further includes a surface treatment step in order to improve the absorption performance (water absorption capacity under load, liquid permeability, water absorbent speed, and the like). The surface treatment step includes a surface crosslinking step performed by use of a conventional surface crosslinking agent and a conventional surface crosslinking method, and if necessary, further includes an addition step.

(Covalent Bonding Surface Crosslinking Agent)

Various organic or inorganic crosslinking agents can be exemplified as the surface crosslinking agent for use in the present invention, but it is preferable that the surface crosslinking agent be an organic surface crosslinking agent. For the sake of the physical properties, it is preferable to use a surface crosslinking agent such as a polyvalent alcohol compound, an epoxy compound, a polyvalent amine compound or its condensed product with a halo epoxy compound, an oxazoline compound, a (mono, di, or poly)oxazolidinone compound, and an alkylene carbonate compound. Especially, a dehydrative reactive crosslinking agent such as a polyvalent alcohol compound, an alkylene carbonate compound, or an oxazolidinone compound, which needs high-temperature reaction can be used. In a case where a dehydrative reactive crosslinking agent is not used, more specifically, the compounds described in U.S. Pat. Nos. 6,228,930, 6,071,976, 6,254,990, and the like can be exemplified. For example, polyvalent alcohol compounds, such as mono-, di-, tri-, tetra-, or propylene glycol, 1,3-propanediol, glycerin, 1,4-butanediol, 1,3-butanediol, 1,5-pentanediol, 1,6-hexanediol, and sorbitol; epoxy compounds, such as ethylene glycol diglycidyl ether, and glycidol; alkylene carbonate compounds such as ethylene carbonate; oxetane compounds; cyclic urea compounds, such as 2-imidazolidinone; and the like are exemplified.

(Solvent or the Like)

An amount of the surface crosslinking agent to be used is determined as appropriate, preferably 0.001 parts by weight to 10 parts by weight, and more preferably 0.01 parts by weight to 5 parts by weight relative to 100 parts by weight of the water absorbent resin particles. In addition to the surface crosslinking agent, water is used in combination preferably. An amount of the water used herein is preferably in the range of 0.5 parts by weight to 20 parts by weight, and more preferably 0.5 parts by weight to 10 parts by weight relative to 100 parts by weight of the water absorbent resin particles. In case where an inorganic surface crosslinking agent and an organic surface crosslinking agent are used in combination, the surface crosslinking agents are respectively used in an amount preferably 0.001 parts by weight to 10 parts by weight, and more preferably 0.01 parts by weight to 5 parts by weight relative to 100 parts by weight of the water absorbent resin particles.

In this case, a hydrophilic organic solvent may be used in an amount preferably in a range of 0 to 10 parts by weight, more preferably in a range of 0 to 5 parts by weight, relative to 100 parts by weight of the water absorbent resin particles. In adding a surface crosslinking agent solution to the water absorbent resin particles, water-insoluble fine particle powder or a surfactant may be added as well in an amount not adversely affecting the effect of the present invention, for example, preferably in a range of 0 to 10 parts by weight, more preferably in a range of 0 to 5 parts by weight, and still more preferably in a range of 0 to 1 part by weight. Examples of usable surfactants and an amount of the surfactant to use are exemplified in U.S. Pat. No. 7,473,739 or the like.

(Mixing)

In a case where the surface crosslinking agent solution is mixed with the water absorbent resin particles, the water absorbent resin particles swell with, for example, water or the like, of the surface crosslinking agent solution. Swollen water absorbent resin particles are dried by heating. The preferred heating temperature is 80° C. to 220° C. Further, the preferred heating time is 10 minutes to 120 minutes.

The mixing of the surface crosslinking agent with the water absorbent resin particles is carried out preferably by using a vertical or horizontal high-speed rotation stirring mixer. The number of revolutions of the mixer is preferably 100 rpm to 10,000 rpm, and more preferably 300 rpm to 2,000 rpm. Further, the retention time is preferably within 180 seconds, more preferably 0.1 to 60 seconds, and still more preferably 1 to 30 seconds.

(Ionic Bonding Surface Crosslinking Agent)

The present invention additionally includes an addition step for adding at least one of a polyvalent metal salt, a cationic polymer, and inorganic microparticles, either simultaneously or separately with the surface crosslinking step described above. That is, the liquid permeability, the water absorbent speed, and the like may be improved by solely using the inorganic surface crosslinking agent other than the organic surface crosslinking agent, or by using them in combination. The inorganic surface crosslinking agent and the organic surface crosslinking agent may be used concurrently or separately. Examples of the inorganic surface crosslinking agent to use encompass divalent or greater, preferably polyvalent like trivalent or tetravalent metal salt (organic salt or inorganic salt), and hydroxide. Usable polyvalent metals may include aluminum, zirconium and the like. Aluminum lactate and aluminum sulfate may be also exemplified. An aqueous solution containing aluminum sulfate is preferably employed.

(3-6) Other Steps

Besides those steps described above, a second classification step, an evaporated monomer recycling step, a granulation step, a fine powder removing step, or the like may be provided, if necessary. For example, the water absorbent resin powder preferably contains a granulated product or a recycled fine powder. Further, the additive may be used for a monomer or a polymer thereof in order to attain the effect of color stability with the lapse of time or prevent gel deterioration, and the like.

By containing a granulated product or a recycled fine powder, it is possible to control the particle size or improve the water absorbent speed. The granulation can be achieved by adding water (for example, 1 to 200% by weight) to the water absorbent resin powder, and by drying, if necessary. Further, fine powder recycling is a step of recycling the water absorbent resin microparticles after classification (for example, those passing through a sieve with 150 μm mesh/1 to 30% by weight) to the polymerization step or the drying step.

Further, depending on the purpose, a reducing agent, a chelating agent, an oxidizing agent, an anti-oxidant, water, a deodorant, an antimicrobial agent, a polyvalent metal compound, a water-insoluble inorganic or organic powder such as silica or metal soap, a deodorant, an antimicrobial agent, pulp, a thermoplastic fiber, or the like may be added to the water absorbent resin powder in an amount of more than 0% by weight but equal to or less than 3% by weight, and preferably more than 0% by weight but equal to or less than 1% by weight. The preferred amount of surfactant in the water absorbent resin powder is in the above range.

[4] Use of Polyacrylic Acid (Salt)-Based Water Absorbent Resin Powder

The water absorbent resin powder obtainable by the production method of the present invention is not limited to particular applications, but is preferably applicable to absorbent articles such as a paper diaper, feminine napkins, and an incontinence pad. The water absorbent resin powder exhibits an excellent property in a case where it is used in a high concentration diaper (a paper diaper in which a lot of water absorbent resin powder is used per piece) having problems such as malodor derived from a material, and coloration, particularly in a case where it is used in an upper layer part of the absorbent body of the above absorbent article.

As to these absorbent articles, the absorbent body, which may arbitrary contain other absorbing material (such as pulp or fibers), have water absorbent resin powder content (core concentration) preferably 30% by weight to 100% by weight, more preferably 40% by weight to 100% by weight, still more preferably 50% by weight to 100% by weight, further still more preferably 60% by weight to 100% by weight, particularly preferably 70% by weight to 100% by weight, and most preferably 75% by weight to 95% by weight. For example, in a case where the water absorbent resin powder obtainable by the production method of the present invention is used with the above core concentration particularly in the upper part of the absorbent body, liquid is efficiently distributed in the absorbent article, and an amount of the liquid to be absorbed by the entire absorbent article is improved because it has an excellent diffusivity of absorbed liquid such as urine thanks to a high liquid permeability of the absorbent article. It is further possible to provide the absorbent articles which maintain white color hue, thus giving an impression of cleanness. The core concentration is defined by the weight ratio [% by weight] of the water absorbent resin powder [g] relative to the total amount [g] of the water absorbent resin powder [g] and hydrophilic fiber materials [g] in core.

EXAMPLES

Hereinafter, the present invention will be described in view of the examples. The present invention is, however, not construed limitedly to the examples. The physical properties mentioned in the claims of the present invention or in the examples were determined under the conditions of room temperature (20 to 25° C.) and a humidity of 50 RH % by an EDANA method or the measurement methods below unless otherwise stated. The electric devices mentioned in Examples and Comparative Examples were operated at 200 V or 100 V with use of a 60 Hz power supply. The description below may, for convenience, use the letter "L" to mean "liter" and the sign "wt %" to mean "percent by weight".

(Measurement of Physical Properties of Water Absorbent Resin Powder)

(A) CRC (Water Absorption Capacity without Load)

CRC (water absorption capacity without load) of the water absorbent resin powder according to the present invention was measured with reference to EDANA method (ERT 441.2-02).

(B) AAP (Water Absorption Capacity Under Load)

AAP (water absorption capacity under load) of the water absorbent resin powder according to the present invention was measured with reference to EDANA method (ERT 442.2-02). Meanwhile, it may be also measured after modifying load condition to 4.83 kPa (0.7 psi). For such case, it is expressed as AAP 0.7. Further, when the load condition includes 2.07 kPa (0.3 psi) according to EDANA method, it is expressed as AAP 0.3.

(C) Ext (Water Soluble Component)

Ext (water soluble component) of the water absorbent resin powder according to the present invention was measured with reference to paragraphs [0134] to [0146] of JP-A No. 2006-055833 or EDANA method (ERT 470.2-02).

(D) Moisture Content

Moisture content of the water absorbent resin powder according to the present invention was measured with reference to EDANA method (ERT 430.2-02). Meanwhile, in the present examples, measurement was made after changing the water absorbent resin powder to 1 g and temperature condition to 180° C.

(E) Degradable Soluble Component

Degradable soluble component of the water absorbent resin powder according to the present invention was measured according to the following method.

Specifically, to physiological saline prepared in advance, L-ascorbic acid was added to 0.05% by weight to prepare a solution for deterioration test. Specifically, by dissolving 0.5 g of L-ascorbic acid in 999.5 g of physiological saline, 1,000.0 g of solution for deterioration test was prepared.

The solution for deterioration test (200 ml) was added to a 250 ml polypropylene cup with lid, and by adding 1.0 g of the water absorbent resin powder, a swollen gel was formed. The container was covered with a lid and hermetically closed, and the swollen gel was kept for 2 hours in an atmosphere of 60° C. After 2 hours, a cylindrical stirrer chip with a length of 30 mm and a thickness of 8 mm was added, and the soluble component after deterioration was extracted with stirring for 1 hour from the hydrogel with the same method as above (Ext (water soluble component)).

After extracting for 1 hour with stirring, filtration was performed in the same manner as the method for measuring soluble component. By performing pH titration, the degradable soluble component [% by weight] was obtained from the solution for deterioration test using the same equation.

(F) FSR (Water Absorbent Speed)

FSR (water absorbent speed) of the water absorbent resin powder according to the present invention was measured with reference to the method described at lines 5 to 20, column 15 of Patent Literature 11 (U.S. Pat. No. 6,849,665).

(G) Evaluation of Powder Flowability After Water Absorption

As an evaluation of powder flowability of the water absorbent resin powder according to the present invention after water absorption, there are "blocking ratio against moisture absorption" according to the following measurement method and "powder flowability" obtained from the blocking ratio against moisture absorption.

Specifically, for the blocking ratio against moisture absorption, 2 g of the water absorbent resin powder was evenly sprayed on a bottom of an aluminum cup whose an inside diameter was 52 mm and a height was 22 mm, and was quickly placed in a constant-temperature-and-moisture apparatus (PLATINOUS LUCIFER PL-2 G, product of TABAI ESPEC CORPORATION) in which temperature had been adjusted to 25° C. and relative humidity had been adjusted to 90% in advance. Then, it was left in the constant-temperature-and-moisture apparatus for 60 minutes. Thereafter, the water absorbent resin powder that had absorbed moisture was moved onto a JIS standard sieve (a diameter is 7.5 cm, and a mesh size is 2,000 μm). At that time, when the water absorbent resin powder that had absorbed moisture is strongly adhered onto the aluminum cup, it was removed and transferred to the sieve while being careful not to disrupt as much as possible the blocked water absorbent resin powder after water absorption.

Subsequently, the sieve containing the water absorbent resin powder after water absorption was sieved for 8 seconds by using a sieve shaker (IIDA SIEVE SHAKER, TYPE: ES-65, SER. No. 0501). Then, a weight W1 [g] of the water absorbent resin powder which remained on the sieve and a weight W2 [g] of the water absorbent resin powder which passed through the sieve were measured. According to the following equation, the blocking ratio against moisture absorption and powder flowability were calculated. Smaller blocking ratio against moisture absorption indicates better flowability during water absorption and more improved handlability of the powder, or the like.

(Blocking ratio against moisture absorption)[%]=$W1/(W1+W2) \times 100$ (Powder flowability)[%]=100−(Blocking ratio against moisture absorption)

(H) p-Methoxyphenol, Chelating Agent, and Reducing Agent Contained in Water Absorbent Resin Powder Content of each of p-methoxyphenol, chelating agent, and reducing agent contained in the water absorbent resin powder according to the present invention was measured with reference to the method described in paragraphs [0317] to [0319] of Patent Literature 51 (International Publication No. WO 2011/040530 pamphlet).

(I) Internal Gas Bubbles Ratio

Internal gas bubbles ratio of the water absorbent resin powder according to the present invention was calculated from the following apparent density ($\rho 1$) and true density ($\rho 2$) based on the following equation.

(Internal gas bubbles ratio)[%]=($\rho 2-\rho 1$)/$\rho 2 \times 100$ (Apparent Density)

After removing moisture from the water absorbent resin powder, the apparent density that takes into consideration gas bubbles (internal gas bubbles/also referred to as closed-cells) present inside the water absorbent resin powder was measured with use of a dry densimeter (dry measurement of the volume of a water absorbent resin powder having a predetermined weight).

Specifically, 6.0 g of the water absorbent resin powder was weighed, placed in an aluminum cup having a bottom surface with a diameter of approximately 5 cm, and then dried the water absorbent resin in a no-air flow dryer at 180° C. The water absorbent resin powder was left for 3 hours or longer until its moisture content was not greater than 1% by weight, and thus sufficiently dried the water absorbent resin powder. After the drying, the apparent density (unit: [g/cm$^3$]) of 5.00 g of the water absorbent resin after drying was measured with use of a dry automatic densimeter (AccuPycII 1340TC-10CC, produced by Shimadzu Corporation, carrier gas: helium). The measurement was repeated until the measured values were the same continuously for 5 or more times.

(True Density)

Figure 3:
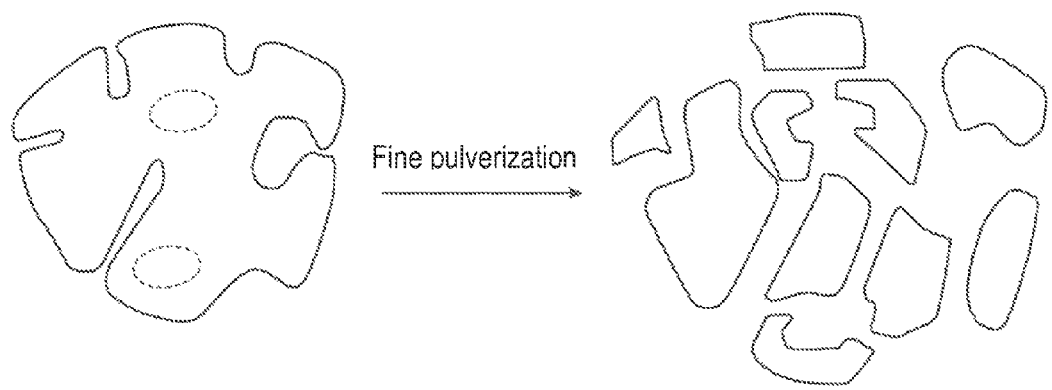
FIG. 3 is a cross-sectional view schematically illustrating an operation of fine pulverization of the water absorbent resin powder (for example, the ratio of the particle size of 850 to 150 μm is 95% by weight or more) to less than 45 μm, for measurement of the true density of the present invention.

Internal gas bubbles (closed-cells) present inside a water absorbent resin powder normally have a diameter of 1 μm to 300 μm. However, at the time of pulverization, it is pulverized preferentially at portions close to closed-cells. In the case where a water absorbent resin powder has been pulverized to have a particle diameter of less than 45 μm, the resulting water absorbent resin has almost no closed-cells (see FIG. 3). The present invention thus evaluated, as a true density, a dry density of a water absorbent resin powder that had been pulverized to have a particle diameter of less than 45 μm.

Specifically, 15.0 g of the water absorbent resin powder and 400 g of columnar ceramic balls (each with a diameter of 13 mm and a length of 13 mm) were added to a ball mill pot (produced by Teraoka Corporation, type No. 90/an internal size, a diameter: 80 mm, a height: 75 mm; an external size, a diameter: 90 mm, a height: 110 mm), and operated the ball mill pot at 60 Hz for 2 hours to prepare a water absorbent resin powder that would pass through a JIS standard sieve having a mesh size of 45 μm (that is, a particle diameter of less than 45 μm). Then, 6.0 g of that water absorbent resin powder with a particle diameter of less than 45 μm was dried in a manner similar to the manner described under [Apparent density] above, that is, at 180° C. for 3 hours or longer, and then the dry density was measured. The value thus measured was designated as the "true density" of the present invention.

(J) Anti-Damaging Property Test

Anti-damaging property test of the water absorbent resin powder according to the present invention was performed according to mechanical damaging test method described at lines 23 to 45, column 21 of Patent Literature 24 (U.S. Pat. No. 6,562,879). However, the vibration time was changed to 10 minutes.

(K) Accelerated Weather Resistance Test

Accelerated weather resistance test of the water absorbent resin powder according to the present invention was performed according to the accelerated weather resistance test described in paragraphs [0305] to [0312] of Patent Literature 51 (International Publication No. WO 2011/040530 pamphlet) (Gel deterioration test 1).

(L) Initial Color Hue and Color Hue with the Lapse of Time (YI Value)

Color hue of the water absorbent resin powder according to the present invention was evaluated as YI (Yellow Index) value. As a measurement apparatus, a spectral colorimeter SZ-Σ80 (product of NIPPON DENSHOKU INDUSTRIES Co., LTD) was used, and reflective measurement was selected as a measurement condition. Meanwhile, the spectral colorimeter is equipped with a sample container for a powder • paste sample (an internal diameter of 30 mm and a height of 12 mm), standard rounded white plate No. 2 for a powder • paste sample, and 30φ light-transmitting pipe.

Next, 5 g of the water absorbent resin powder was filled in the container for powder • paste sample, and a YI value (Yellow Index) on a surface of the water absorbent resin powder was measured at room temperature (20 to 25° C.) and humidity of 50 RH %. Meanwhile, when the water absorbent resin powder is a (common) water absorbent resin powder after production or before factory shipment, or a water absorbent resin powder which has been stored under condition including temperature of 30° C. or less and humidity of 50 RH % or lower and it is within 1 year from the production, its color hue was expressed as "initial color hue." Further, when the water absorbent resin powder is a water absorbent resin powder after the accelerated coloration test described below, its color hue is expressed as "color hue with the lapse of time."

(Accelerated Coloration Test)

Accelerated coloration test means a test including exposing the water absorbent resin powder (5 g filled in a sample container for powder • paste) for 7 days in a constant temperature and constant humidity incubator (mini environment testing device: SH-641, manufactured by ESPEC Corporation) which has been adjusted to the temperature of 70±1° C. and relative humidity of 65±1% RH.

(M) Evaluation of Absorbent Body • Absorbent Articles

The water absorbent resin powder according to the present invention was evaluated by producing various absorbent bodies (mini adsorbent body, absorbent body of paper diaper type) • absorbent articles listed below.

(a) Absorption Amount by Absorbent Articles 50 g of the water absorbent resin powder and 50 g of wood-crushed pulp were mixed by dry mixing using a mixer and then, the obtained mixture was applied onto a wire screen of 400 mesh (mesh size of 38 μm), and by using air flow by using a batch-type aerial application web-maker, so as to form a web (sheet). Meanwhile, the amount per area was controlled to 526 [g/m$^2$] according to an aerial application web-making time. After that, it was cut to a rectangular shape (120 mm×380 mm in size). Then, by pressing the web with pressure of 196.14 kPa (2 [kgf/cm$^2$]) for 5 seconds, an absorbent body of a paper diaper type was obtained.

Subsequently, a back sheet (liquid impermeable sheet) with a size of 120 mm×380 mm made of liquid impermeable polypropylene with so-called leg gather, the absorbent body of a paper diaper type, and a top sheet (liquid permeable sheet) with a size of 120 mm×380 mm made of liquid permeable polypropylene are combined together in this order by using a two-side sticky tape. By further attaching two tape fasteners, an absorbent article (that is, a paper diaper) was produced.

This absorbent article was fitted up to each of four units of so-called kewpie dolls (three units of which had a body length of 55 cm and a weight of 5 kg, and the other one unit had a body length of 65 cm and a weight of 6 kg), and these dolls were laid on their faces at room temperature of 37° C. Then, a tube was inserted to a position corresponding to where urine is discharged from the human body.

Subsequently, physiological saline containing L-ascorbic acid in a concentration of 0.005% by weight was sequentially injected through the tube in an amount of 50 g per injection with an interval of 90 minutes. Then, this injection operation was ended when the injected physiological saline began leaking without being absorbed by the absorbent article, and the amount of the physiological saline, as had been injected until then, was measured. The average value thereof for the above-mentioned four units of kewpie dolls was regarded as the absorption amount of the absorbent articles of the present invention.

(b) Absolute Absorption Amount of Mini Absorbent Body 5 g of the water absorbent resin powder and 5 g of wood-crushed pulp were mixed by dry mixing using a mixer and then, the obtained mixture was applied onto a wire screen of 400 mesh (a mesh size of 38 μm), and formed into a rectangular web (size: 100 mm×167 mm). Then, by pressing the web with pressure of 196.14 kPa (2 [kgf/cm$^2$]) for 1 minute, a mini absorbent body was obtained (amount per area: 0.06 [g/m$^2$]).

First, the mini absorbent body (a size: 100 mm×167 mm/core concentration of 50%) was placed into a non-woven bag (size: 120 mm×180 mm). After heat-sealing, it was then immersed in 2 L of a 0.9% by weight aqueous solution of sodium chloride containing L-ascorbic acid at 0.005% by weight, which has been adjusted to 25±3° C. Thirty minutes later, the bag was pulled up and hung for 10 minutes to remove moisture, and then weight of the bag (W3 [g]) was measured.

The same operation was performed without adding the mini absorbent body, and the weight of the bag at that time (W4 [g]) was measured, and the difference between them (W3−W4) was calculated as an absolute absorption amount [g] of the mini absorbent body.

(c) Absolute Absorption Amount of Absorbent Body of Paper Diaper Type 60 g of the water absorbent resin powder and 40 g of wood-crushed pulp were mixed by dry mixing using a mixer and then, the obtained mixture was applied onto a wire screen of 400 mesh (a mesh size of 38 μm), and by using air flow by using a batch-type aerial application web-maker, so as to form a web (sheet). Meanwhile, the amount per area was controlled to 439 [g/m$^2$] according to an aerial application web-making time. After that, it was cut to a rectangular shape (120 mm×380 mm in size). Then, by pressing the web with pressure of 196.14 kPa (2 [kgf/cm$^2$]) for 1 minute, an absorbent body of a paper diaper type was obtained. A content of the water absorbent resin powder in the obtained absorbent body of a paper diaper type was 12 g and it had core concentration of 60%.

The absorbent body of a paper diaper type (size: 120 mm×380 mm/core concentration of 60%) was placed into a non-woven bag (size: 130 mm×400 mm). After heat-sealing, it was then immersed in 5 L of a 0.9% by weight aqueous solution of sodium chloride including L-ascorbic acid at 0.005% by weight, which has been adjusted to 25±3° C. Thirty minutes later, the bag was pulled up and hung for 10 minutes to remove moisture, and then weight of the bag (W5 [g]) was measured.

The same operation was performed without adding the absorbent body of a paper diaper type, the weight of the bag at that time (W6 [g]) was measured, and the difference between them (that is, W5−W6) was calculated as an absolute water absorption amount [g] of the absorbent body of a paper diaper type.

(d) Reversion Amount of Absorbent Body of a Paper Diaper Type

A simulated paper diaper was produced according to the following method.

Specifically, on a back sheet (liquid impermeable sheet) with a size of 120 mm×380 mm made of liquid impermeable polypropylene, the above absorbent body of a paper diaper type was placed, and on top of it, a non-woven fabric with a size of 120 mm×380 mm and a top sheet (liquid permeable sheet) with the same size and made of liquid permeable polypropylene are placed, and thus a simulated paper diaper consisting of 4 layers was produced.

Subsequently, an acrylic plate (size: 120 mm×380 mm) having at the center a liquid injection hole with diameter of 70 mm was placed on top of the simulated paper diaper, and a weight was further placed thereon to have a load of 2.1 kPa can be uniformly applied on the entire surface.

Subsequently, 75 ml of physiological saline including L-ascorbic acid at 0.005% by weight (a 0.9% by weight aqueous solution of sodium chloride) was added through the liquid injection hole, total five times with an interval of 30 minutes (a total addition amount: 375 ml). The time required for the fifth-added physiological saline to get absorbed by the absorbent body of paper diaper type (that is, time for injection of physiological saline from the liquid permeable sheet) was recorded as "liquid absorption time."

After measuring the liquid absorption time and thirty minutes thereafter, the weight and acrylic plate were removed, 30 pieces of a kitchen towel (size: 120 mm×380 mm, manufactured by Oji Nepia Co., Ltd.) of which total weight has been measured in advance (W7 [g]) were placed thereon, and an acrylic plate (size: 120 mm×380 mm) and a weight (total weight: 10 kg) with easily applicable weight were quickly placed thereon.

One minute later, weight of the 30 pieces of a kitchen towel (W8 [g]) was measured, and the difference (that is, W8−W7) was measured as the reversion amount [g] of the absorbent body of paper diaper type.

Comparative Example 1

Based on Example 18 of Patent Literature 45

Based on Example 18 of Patent Literature 45 (U.S. Pat. No. 6,107,358), the following operation was performed to obtain the comparative water absorbent resin powder (1).

Specifically, an aqueous monomer solution was prepared by mixing 306 g of acrylic acid, 3240 g of 37% sodium acrylate, 8.2 g of polyethylene glycol (n=8) diacrylate, 0.3 g of polyoxyethylene sorbitan monostearate (trade name: Rheodol TW-5120, produced by Kao Co., Ltd.), 1420 g of deionized water, and 10 g of a 10% aqueous solution of sodium persulfate. This aqueous monomer solution and nitrogen were subjected to fluid mixing by the use of a device Whip Auto Z produced by AICOHSHA to disperse gas bubbles of nitrogen gas in the aqueous monomer solution and perform polymerization of the monomer having the gas bubbles dispersed therein. To be specific, this aqueous monomer solution was supplied by means of the aspirator at a rate of 1 kg per minute from the nozzle side and the nitrogen gas was supplied via the lateral pipe at a rate of 2 liters per minute and they were subjected to fluid mixing. The resultant mixture was passed through the mixing zone provided with irregularities (protrusions) and led to the polymerization bath. The aqueous monomer solution which had passed the mixing zone had gas bubbles of nitrogen dispersed therein and had the volume thereof increased to 1.5 times the original volume. To this aqueous monomer solution containing gas bubbles, 10 g of a 10% aqueous solution of sulfite was added to initiate polymerization immediately. The stationary polymerization was continued at a temperature in the range of 25 to 95° C. for 1 hour with the gas bubbles dispersed therein to obtain the comparative water-containing gel-like crosslinked polymer (1).

Subsequently, the comparative hydrogel (1) was subjected to gel-crushing by using a meat chopper (Iizuka Kogyo Co. Ltd. MEAT-CHOPPER TYPE: 12VR-400KSOX, die pore diameter: 6.4 mm, pore number: 38, die thickness: 8 mm) followed by drying, pulverizing, and classifying to obtain the comparative water absorbent resin powder (1) in pulverized non-uniformly shape which has solid content of 95% by weight, weight average particle diameter (D50) of 450 μm, and logarithmic standard deviation ($\sigma\zeta$) of the particle size distribution of 0.39. The comparative water absorbent resin powder (1) has CRC of 37.8 [g/g], FSR of 0.48 [g/g/s], bulk specific gravity of 0.53 [g/cm$^3$], and internal gas bubbles ratio of 6.8%. Various physical properties of the comparative water absorbent resin powder (1) are shown in Table 1.

Comparative Example 2

Surface Crosslinking of Comparative Example 1

Relative to 100 parts by weight of the comparative water absorbent resin powder (1) obtained in Comparative example 1, a surface crosslinking agent solution containing 0.48 parts by weight of 1,4-butanediol, 0.75 parts by weight of propylene glycol, and 4.0 parts by weight of deionized water was uniformly sprayed to the comparative water absorbent resin powder (1) and mixed. The comparative water absorbent resin particles (2') mixed with the surface crosslinking agent solution was subjected to heat-surface crosslinking treatment of 45 minutes by using a hot-air dryer (temperature: 180° C.). After the heat treatment, the resultant comparative water absorbent resin particles (2') were pulverized until the particles became small enough to pass the JIS standard sieve of 850 μm in mesh size, thereby obtaining the surface crosslinked comparative water absorbent resin particles (2).

Relative to 100 parts by weight of the surface crosslinked comparative water absorbent resin particles (2) thus obtained, a mixture solution containing 0.80 parts by weight of a 27% by weight aqueous solution of aluminum sulfate (8% by weight based on aluminum oxide) as a multivalent metal cation, 0.134 parts by weight of a 60% by weight aqueous solution of sodium lactic acid as α-hydroxycarboxylic acid, and 0.016 parts by weight of propylene glycol was added. After the addition, the particles were dried at 60° C. for 1 hour with no air flow. Then, the resultant particles was sieved with the JIS standard sieve of 850 μm in mesh size, thereby obtaining the comparative water absorbent resin powder (2).

The comparative water absorbent resin powder (2) has CRC of 27.6 [g/g], SFC of 48 [×10$^{-7}$·s·cm$^3$·g$^{-1}$], FSR of 0.50 [g/g/s], bulk specific gravity of 0.55 [g/cm$^3$], and internal gas bubbles ratio of 6.8%. Various physical properties of the comparative water absorbent resin powder (2) are shown in Table 1.

Comparative Example 3

Based on Comparative Example 2 of Patent Literature 52

Based on Comparative example 2 of Patent Literature 52 (International Publication No. WO 2011/078298 pamphlet), the following operation was performed to obtain the comparative water absorbent resin powder (3).

Into a polypropylene vessel of 2 L in capacity, 356.1 g of acrylic acid, 2.17 g of polyethylene glycol diacrylate (molecular weight 523) as an internal crosslinking agent, 94.6 g of a 0.1% by weight aqueous solution of diethylenetriamine pentaacetic acid trisodium as chelating agent, 144.9 g of a 48.5% by weight aqueous solution of sodium hydroxide, and 242.5 g of deionized water (i.e., ion exchange water) were added followed by dissolving (mixing) to produce the comparative aqueous monomer solution (3'). The temperature of the comparative aqueous monomer solution (3') was increased up to 65° C. by the neutralization heat at the first step right after production.

Next, the comparative aqueous monomer solution (3') was cooled under stirring, and when the liquid temperature is 53° C., 148.9 g of a 48.5% by weight aqueous solution of sodium hydroxide adjusted to 30° C. was added and mixed therein to produce the comparative aqueous monomer solution (3). At that time, temperature of the comparative aqueous monomer solution (3) was increased up to 83.5° C. by the neutralization heat at the second step right after production.

Next, when the temperature of the comparative aqueous monomer solution (3) is lowered to 83° C., 15.3 g of a 3.8% by weight aqueous solution of sodium persulfate was added thereto under stirring. Immediately after that, it was poured into a stainless vat type vessel (340 mm×340 mm bottom, 25 mm height with Teflon (registered trademark) coated inner surface) under atmospheric pressure. Note that the vat type vessel had been heated to a surface temperature of 40° C. by using a hot plate (NEO HOTPLATE HI-1000, manufactured by AS ONE Corporation). Further, dissolved oxygen amount in the comparative aqueous monomer solution (3) before adding an aqueous solution of sodium persulfate was 6.53 [ml/L].

Fifteen seconds after the comparative aqueous monomer solution (3) was poured into the vat type vessel, polymerization was started. The polymerization proceeded with generating a water steam, and foaming and swelling in various directions. Then, it was shrunken to a size slightly larger than the vat type vessel. The swelling and shrinking was completed within about 1 minute. Three minutes later from the start of the polymerization, a comparative water-containing gel-like crosslinked polymer (comparative hydrogel) (3) was taken out of the vat type vessel. Meanwhile, these processes were performed under atmospheric pressure. A peak temperature in the polymerization was 108° C.

The water-containing gel-like crosslinked polymer, (the comparative hydrogel (3)) obtained from above polymerization reaction was subjected to gel-crushing by using a meat chopper (Iizuka Kogyo Co. Ltd., MEAT-CHOPPER TYPE: 12VR-400KSOX, die pore diameter: 6.4 mm, pore number: 38, die thickness: 8 mm), thereby obtaining crushed comparative water-containing gel-like crosslinked polymer (3) (particulated comparative hydrogel (3)). At that time, the addition amount of the comparative hydrogel (3) was 350 [g/min] and the gel-crushing was performed by adding deionized water adjusted to 90° C. at a rate of 80 [g/min] concurrently with the addition of the comparative hydrogel (3).

The particulated hydrogel (3) obtained with the gel-crushing operation described above was spread on a stainless mesh of 850 µm in mesh size, and dried with hot air of 180° C. for 30 minutes. Then, the obtained comparative dry product (3) was pulverized by using a roll mill (Inoguchi Giken Ltd., WML-type roll pulverizing device), and classified by using JIS standard sieves of 850 µm and 45 µm in mesh size. According to the above operations, the comparative water absorbent resin powder (3) pulverized non-uniformly shape having solid content of 97% by weight, weight average particle diameter (D50) of 460 µm, and logarithmic standard deviation (σζ) of the particle size distribution of 0.40 was obtained.

The comparative water absorbent resin powder (3) has CRC of 34.0 [g/g], FSR of 0.27 [g/g/s], bulk specific gravity of 0.66 [g/cm³], and internal gas bubbles ratio of 2.6%. Various physical properties of the comparative water absorbent resin powder (3) are shown in Table 1.

Comparative Example 4

Surface Crosslinking of Comparative Example 3

The comparative water absorbent resin powder (3) which has been obtained from Comparative example 3 was subjected to the same operations as Comparative example 2 to obtain the comparative water absorbent resin powder (4). The comparative water absorbent resin powder (4) has CRC of 26.6 [g/g], SFC of 150 [×10⁻⁷·s·cm³·g⁻¹], FSR of 0.26 [g/g/s], bulk specific gravity of 0.66 [g/cm³], and internal gas bubbles ratio of 2.6%. Various physical properties of the comparative water absorbent resin powder (4) are shown in Table 1.

Production Example 1

Based on Production Example 1 of Patent Literature 53

Based on Preparation example 1 of Patent Literature 53 (International Publication No. WO 2011/126079 pamphlet), the following operations were performed to obtain the belt-like water-containing gel-like crosslinked polymer (a). Hereinbelow, the water-containing gel crosslinked polymer is referred to as a "hydrogel."

First, an aqueous monomer solution (a) containing 193.3 parts by weight of acrylic acid, 64.4 parts by weight of a 48% by weight aqueous solution of sodium hydroxide, 1.26 parts by weight of polyethylene glycol diacrylate (average number of n=9) (0.09% by mol relative to acrylic acid), 52 parts by weight of a 0.1% by weight aqueous solution of pentasodium ethylenediamine tetra(methylene phosphonate), and 134 parts by weight of deionized water was prepared.

Next, with use of a constant rate pump, the above aqueous monomer solution (a) with a temperature adjusted to 40° C. was continuously fed, and 97.1 parts by weight of a 48% by weight aqueous solution of sodium hydroxide was continuously added by line mixing. Meanwhile, at that time, the temperature of the above aqueous monomer solution (a) was increased to 85° C. due to heat of neutralization.

Further, 8.05 parts by weight of a 4% by weight aqueous solution of sodium persulfate was continuously added by line mixing, and then continuously fed to a continuous polymerization device equipped with a planar polymerization belt provided with an ingate at each end, so that it would have a thickness of approximately 7.5 mm. After that, the polymerization was carried out continuously (polymerization period: 3 minutes/polymerization peak temperature of 110° C.) to obtain the belt-like hydrogel (a). The belt-like hydrogel (a) had CRC of 28.0 [g/g], resin solid content of 53.0% by weight, water soluble component of 4.0% by weight, and weight average molecular weight of the water soluble component of 218,377 [Da]. Further, it contained gas bubbles due to boiling at the time of polymerization.

Production Example 2

Having High CRC and Use of p-methoxyphenol

The belt-like hydrogel (b) was obtained by performing the same operations as Production example 1 except that polyethylene glycol diacrylate (average number of n=9) of Production example 1 is changed to 0.88 parts by weight (i.e., about 0.06% by mol relative to acrylic acid) and p-methoxyphenol is used at 70 ppm (relative to acrylic acid) during polymerization. The belt-like hydrogel (b) had CRC of 30.1 [g/g], resin solid content of 53% by weight, water soluble component of 5.5% by weight, and weight average molecular weight of the water soluble component of 310,000 [Da].

Production Example 3

Increased Amount of p-Methoxyphenol for Production Example 2

The belt-like hydrogel (c) was obtained by performing the same operations as Production example 2 except that p-methoxyphenol of Production example 2 is changed to 250 ppm (relative to acrylic acid). Various physical properties of the belt-like hydrogel (c) were at almost the same level as the hydrogel (b) of Production example 2.

Production Example 4

No Use of p-Methoxyphenol for Production Example 2

The belt-like hydrogel (d) was obtained by performing the same operations as Production example 2 except that p-methoxyphenol of Production example 2 is not used at the time of polymerization. Various physical properties of the belt-like hydrogel (d) were at almost the same level as the hydrogel (b) of Production example 2.

Production Example 5

No Use of Chelating Agent for Production Example 2

The belt-like hydrogel (e) was obtained by performing the same operations as Production example 2 except that a chelating agent of Production example 2 is not used. Various physical properties of the belt-like hydrogel (e) were at almost the same level as the hydrogel (b) of Production example 2.

Production Example 6

Having High CRC for Production Example 2 (Reducing Crosslinking Agent Amount)

The belt-like hydrogel (f) was obtained by performing the same operations as Production example 2 except that polyethylene glycol diacrylate (average number of n=9) of Production example 2 is changed to 0.41 parts by weight (about 0.03% by mol relative to acrylic acid). The belt-like hydrogel (f) had CRC of 38.1 [g/g], resin solid content of 53% by weight, water soluble component of 8.5% by weight, and weight average molecular weight of the water soluble component of 550,000 [Da].

Production Example 7

Having High CRC for Production Example 2 (Reducing Crosslinking Agent Amount)

The belt-like hydrogel (g) was obtained by performing the same operations as Production example 2 except that polyethylene glycol diacrylate (average number of n=9) of Production example 2 is changed to 0.27 parts by weight (about 0.02% by mol relative to acrylic acid). The belt-like hydrogel (g) had CRC of 40.9 [g/g], resin solid content of 53% by weight, water soluble component of 8.5% by weight, and weight average molecular weight of the water soluble component of 651,000 [Da].

Production Example 8

Having High CRC for Production Example 2 (Use of Chain Transfer Agent)

The belt-like hydrogel (h) was obtained by performing the same operations as Production example 2 except that 0.1% by mol of sodium phosphite (relative to acrylic acid (salt)) is added as a water soluble chain transfer agent to the monomers. The belt-like hydrogel (h) had CRC of 30.1 [g/g], resin solid content of 53% by weight, water soluble component of 5.0% by weight, and weight average molecular weight of the water soluble component of 200,000 [Da].

Production Example 9

Use of p-Methoxyphenol for Production Example 1

The belt-like hydrogel (i) was obtained by performing the same operations as Production example 1 except that p-methoxyphenol is used at 70 ppm in the monomers. Various physical properties of the belt-like hydrogel (i) were at almost the same level as the hydrogel (a) of Production example 1.

Comparative Example 5

Gel-Crushing of Comparative Example 1 of Patent Literature 53

Based on Comparative example 1 of Patent Literature 53 (International Publication No. WO 2011/126079 pamphlet), the belt-like hydrogel (b) obtained from Production example 2 was subjected to gel-crushing, drying, pulverizing, classifying, surface crosslinking, and sizing, and as a result, the comparative water absorbent resin powder (5) with internal gas bubbles ratio of 2.6% was obtained.

Specifically, according to continuous cut of belt-like hydrogel (b) obtained from Production example 2 with a cutting length of approximately 300 mm at equal intervals along the width direction relative to the direction in which the polymerization belt moves, the comparative hydrogel (5) was obtained.

The comparative hydrogel (5) with the cutting length of approximately 300 mm was supplied to a screw extruder to gel-crush. As a screw extruder, a meat chopper having, at an end, a porous die having a diameter of 340 mm, a hole diameter of 22 mm, 105 holes, an open hole ratio of 52%, and a thickness of 20 mm and a screw axis with a diameter of 152 mm was used. In the state where the meat chopper was set so that the number of revolutions of the screw axis was 96 rpm, 132,800 [g/min] of the comparative hydrogel (5) was simultaneously fed with 855.8 [g/min] of 70° C. hot water and 3333 [g/min] of water vapor, respectively. At that time, gel grinding energy (GGE) was 17.9 [J/g] and gel grinding energy (2) (GGE (2)) was 8.7 [J/g]. Meanwhile, the comparative hydrogel (5) had a temperature of 90° C. before the gel-crushing, whereas the comparative crushed gel (5) after the gel-crushing, i.e., the comparative particulated hydrogel (5), had a temperature increased to 110° C.

The comparative particulated hydrogel (5) was then scattered on (at this stage, the comparative particulated hydrogel (5) had a temperature of 80° C.) a through-flow belt within 1 minute from the end of the gel-crushing and then subjected to drying at 185° C. for 30 minutes. As a result, 246 parts by weight of the comparative dry polymer (5) (the total amount of output during the drying step) was obtained. The through-flow belt had a moving rate of 1 [m/min]. The hot air had an average wind velocity of 1.0 [m/s] relative to the direction perpendicular to the direction in which the through-flow belt moved. Meanwhile, wind velocity of the hot air was measured with use of constant-temperature thermal anemometer Anemomaster 6162 produced by KANOMAX JAPAN Inc.

Subsequently, the entire amount of the comparative dry polymer (5) which has been obtained prepared through the drying step and having a temperature of approximately 60° C. was fed continuously to a three-stage roll mill to pulverize it, and then classified with use of JIS standard sieves having respective mesh sizes of 710 μm and 175 μm to obtain the comparative water absorbent resin (5) pulverized non-uniformly shape. The comparative water absorbent resin (5) has weight average particle diameter (D50) of 350 μm, and logarithmic standard deviation (σζ) of the particle size distribution of 0.33, CRC of 42.1 [g/g], and water soluble component of 14.1% by weight, and includes 150 μm passing particles (the proportion of particles that would pass through a sieve having a mesh size of 150 μm) at 0.6% by weight.

Next, relative to 100 parts by weight of the comparative water absorbent resin (5), a (covalent bonding) surface crosslinking agent solution containing 0.3 parts by weight of 1,4-butandiol, 0.6 parts by weight of propylene glycol, and 3.0 parts by weight of deionized water was uniformly mixed, and it was heat-treated at 208° C. for approximately 40 minutes so that the comparative water absorbent resin powder (5) would have CRC of about 32 [g/g].

After that, according to crush (sizing) until it passes through JIS standard sieve having a mesh size of 710 μm, the comparative water absorbent resin powder (5) with internal gas bubbles ratio of 2.6% was obtained. Various physical properties of the comparative water absorbent resin powder (5) are described in Table 1.

Example 1

Gel-Crushing for Example 1 of Patent Literature 53

Gel-crushing of the belt-like hydrogel (b) obtained from Production example 2 was performed based on Example 1 of Patent Literature 53. After that, by performing the same drying, pulverizing, classifying, surface crosslinking, and sizing as Comparative example 5, the water absorbent resin powder (1) was obtained.

Specifically, the crushed gel (1), i.e., the particulated hydrogel (1), and the water absorbent resin powder (1) were obtained by performing the same operations as Comparative example 5 except that gel-crushing of the belt-like hydrogel (b) obtained from Production example 2 is performed while the cutting length is changed to 200 mm, hot water and water vapor are not supplied, and screw axis revolution number of the meat chopper is changed to 115 rpm.

In Example 1, the gel grinding energy (GGE) was 27.8 [J/g] and the gel grinding energy (2) (GGE (2)) was 15.5 [J/g]. Meanwhile, temperature of the hydrogel (1) before gel-crushing was 90° C. and temperature of the particulated hydrogel (1) after gel-crushing was lowered to 85° C. Further, temperature of the particulated hydrogel (1) at the time of introduction to a dryer was 75° C.

The water absorbent resin powder (1) has weight average particle diameter (D50) of 340 μm, and logarithmic standard deviation (σζ) of the particle size distribution of 0.32, and includes 150 μm passing particles (the proportion of particles that would pass through a sieve having a mesh size of 150 μm) at 0.7% by weight. Internal gas bubbles ratio of the water absorbent resin powder (1) was 1.9% and other physical properties are shown in Table 1.

Example 2

Gel-Crushing for Example 2 of Patent Literature 53 (Controlling Internal Gas Bubbles Ratio)

Gel-crushing of the belt-like hydrogel (b) obtained from Production example 2 was performed based on Example 2 of Patent Literature 53. After that, by performing the same drying, pulverizing, classifying, surface crosslinking, and sizing as Comparative example 5, the water absorbent resin powder (2) was obtained.

Specifically, the crushed gel (2), i.e., the particulated hydrogel (2), and the water absorbent resin powder (2) were obtained by performing the same operations as Comparative example 5 except that gel-crushing of the belt-like hydrogel (b) obtained from Production example 2 is performed while the cutting length is changed to 200 mm, hot water and water vapor are not supplied, and screw axis revolution number of the meat chopper is changed to 134 rpm.

In Example 2, the gel grinding energy (GGE) was 28.2 [J/g] and the gel grinding energy (2) (GGE (2)) was 15.8 [J/g]. Meanwhile, temperature of the hydrogel (2) before gel-crushing was 90° C. and temperature of the particulated hydrogel (2) after gel-crushing was lowered to 86° C. Further, temperature of the particulated hydrogel (2) at the time of introduction to a dryer was 76° C.

The water absorbent resin powder (2) has weight average particle diameter (D50) of 331 μm, and logarithmic standard deviation (σζ) of the particle size distribution of 0.32, and includes 150 μm passing particles (the proportion of particles that would pass through a sieve having a mesh size of 150 μm) at 0.6% by weight. Internal gas bubbles ratio of the water absorbent resin powder (2) was 1.1% and other physical properties are shown in Table 1.

Example 3

Gel-Crushing for Example 3 of Patent Literature 53 (Controlling Internal Gas Bubbles Ratio)

Gel-crushing of the belt-like hydrogel (b) obtained from Production example 2 was performed based on Example 3 of Patent Literature 53. After that, by performing the same drying, pulverizing, classifying, surface crosslinking, and sizing as Comparative example 5, the water absorbent resin powder (3) was obtained.

Specifically, the crushed gel (3), i.e., the particulated hydrogel (3), and the water absorbent resin powder (3) were obtained by performing the same operations as Comparative example 5 except that gel-crushing of the belt-like hydrogel (b) obtained from Production example 2 is performed while the cutting length is changed to 200 mm, hot water and water vapor are not supplied, and screw axis revolution number of the meat chopper is changed to 153 rpm.

In Example 3, the gel grinding energy (GGE) was 31.9 [J/g] and the gel grinding energy (2) (GGE (2)) was 19.2 [J/g]. Meanwhile, temperature of the hydrogel (3) before gel-crushing was 90° C. and temperature of the particulated hydrogel (3) after gel-crushing was lowered to 87° C. Further, temperature of the particulated hydrogel (3) at the time of introduction to a dryer was 77° C.

The water absorbent resin powder (3) has weight average particle diameter (D50) of 356 μm, and logarithmic standard deviation (σζ) of the particle size distribution of 0.34, and includes 150 μm passing particles (the proportion of particles that would pass through a sieve having a mesh size of 150 μm) at 0.6% by weight. Internal gas bubbles ratio of the water absorbent resin powder (3) was 0.8% and other physical properties are shown in Table 1.

Example 4

Gel-Crushing for Example 4 of Patent Literature 53 (Controlling Internal Gas Bubbles Ratio)

Gel-crushing of the belt-like hydrogel (b) obtained from Production example 2 was performed based on Example 4 of Patent Literature 53. After that, by performing the same drying, pulverizing, classifying, surface crosslinking, and sizing as Comparative example 5, the water absorbent resin powder (4) was obtained.

Specifically, the crushed gel (4), i.e., the particulated hydrogel (4), and the water absorbent resin powder (4) were obtained by performing the same operations as Comparative example 5 except that gel-crushing of the belt-like hydrogel (b) obtained from Production example 2 is performed while hot water and water vapor are not supplied.

In Example 4, the gel grinding energy (GGE) was 23.5 [J/g] and the gel grinding energy (2) (GGE (2)) was 13.2 [J/g]. Meanwhile, temperature of the hydrogel (4) before gel-crushing was 90° C. and temperature of the particulated hydrogel (4) after gel-crushing was lowered to 87° C. Further, temperature of the particulated hydrogel (4) at the time of introduction to a dryer was 77° C.

The water absorbent resin powder (4) has weight average particle diameter (D50) of 351 μm, and logarithmic standard deviation (σζ) of the particle size distribution of 0.33, and includes 150 μm passing particles (that is, the proportion of particles that would pass through a sieve having a mesh size of 150 μm) at 0.5% by weight. Internal gas bubbles ratio of the water absorbent resin powder (4) was 2.3% and other physical properties are shown in Table 1.

Example 5

Addition of Anti-Caking Agent

According to dry stirring and mixing of 0.5 parts by weight of the water-insoluble inorganic microparticles (AEROSIL 200; Nippon Aerosil Company) with 100 parts by weight of the water absorbent resin powder (1) obtained from Example 1, the water absorbent resin powder (5) having the surface coated with water-insoluble inorganic microparticles was obtained. Meanwhile, the internal gas bubbles ratio of the water absorbent resin powder (5) was 1.9%, and the particle size was at almost the same level as Example 1. Other physical properties are shown in Table 1.

Comparative Example 6

No Use of Chelating Agent

By performing the same gel-crushing, drying, pulverizing, classifying, surface crosslinking, and sizing as Example 1 of the belt-like hydrogel (e) obtained from Production example 5, the comparative water absorbent resin powder (6) was obtained. Meanwhile, internal gas bubbles ratio of the comparative water absorbent resin powder (6) was 1.9%, and the particle size was at almost the same level as Example 1. Other physical properties are shown in Table 1.

Comparative Example 7

No Use of p-Methoxyphenol

By performing the same gel-crushing, drying, pulverizing, classifying, surface crosslinking, and sizing as Example 1 of the belt-like hydrogel (d) obtained from Production example 4, the comparative water absorbent resin powder (7) was obtained. Meanwhile, internal gas bubbles ratio of the comparative water absorbent resin powder (7) was 1.9%, and the particle size was at almost the same level as Example 1. Other physical properties are shown in Table 1.

Example 6

Use of p-Methoxyphenol at 250 ppm

By performing the same gel-crushing, drying, pulverizing, classifying, surface crosslinking, and sizing as Example 1 of the belt-like hydrogel (c) obtained from Production example 3, the water absorbent resin powder (6) was obtained. Meanwhile, internal gas bubbles ratio of the water absorbent resin powder (6) was 1.9%, and the particle size was at almost the same level as Example 1. Other physical properties are shown in Table 1.

Example 7

Having High CRC (Use of Reducing Agent)

The water absorbent resin powder (7) was obtained by performing the same operations as Example 2 except that, after performing the same gel-crushing, drying, pulverizing, and classifying as Example 2 of the belt-like hydrogel (h) obtained from Production example 8, the crosslinking density is lowered by shortening the reaction time for the surface crosslinking to 25 minutes. Meanwhile, internal gas bubbles ratio of the water absorbent resin powder (7) was 1.6%, and the particle size was at almost the same level as Example 2. Other physical properties are shown in Table 1.

Example 8

Having High CRC (Reduced Amount of Crosslinking Agent)

By performing the same gel-crushing, drying, pulverizing, classifying, surface crosslinking, and sizing as Example 2 of the belt-like hydrogel (f) obtained from Production example 6, the water absorbent resin powder (8) was obtained. Meanwhile, internal gas bubbles ratio of the water absorbent resin powder (8) was 0.8%, and the particle size was at almost the same level as Example 2. Other physical properties are shown in Table 1.

Example 9

Having High CRC (Reduced Amount of Crosslinking Agent)

By performing the same gel-crushing, drying, pulverizing, classifying, surface crosslinking, and sizing as Example 2 of the belt-like hydrogel (g) obtained from Production example 7, the water absorbent resin powder (9) was obtained. Meanwhile, internal gas bubbles ratio of the water absorbent resin powder (9) was 0.9%, and the particle size was at almost the same level as Example 2. Other physical properties are shown in Table 1.

Comparative Example 8

Based on Example 2 of Patent Literature 52

After performing polymerization based on Example 2 (i.e., a surfactant is used) of Patent Literature 52 (International Publication No. WO 2011/078298 pamphlet), the comparative water absorbent resin powder (8) was obtained by performing the same gel-crushing, drying, pulverizing, and classifying as Comparative example 3.

Specifically, the comparative water absorbent resin powder (8) was obtained by performing the same operations as Comparative example 3 except that, in Comparative example 3, the deionized water is changed to 236.0 g and foaming polymerization is carried out after further adding, as a surfactant, 6.45 g of a 1.0% by weight aqueous solution of polyoxyethylene (20) sorbitan monostearate (produced by Kao Corporation) (polymerization peak temperature of 108° C.). Meanwhile, internal gas bubbles ratio of the comparative water absorbent resin powder (8) was 3.9% and other physical properties are shown in Table 1.

Comparative Example 9

Based on Example 8 of Patent Literature 52

After performing polymerization based on Example 8 (i.e., a surfactant is used) of Patent Literature 52 (International Publication No. WO 2011/078298 pamphlet), the comparative water absorbent resin powder (9) was obtained by performing the same gel-crushing, drying, pulverizing, and classifying as Comparative example 3.

Specifically, the comparative water absorbent resin powder (9) was obtained by performing the same operations as Comparative example 3 except that, in Comparative example 3, the deionized water is changed to 236.0 g and foaming polymerization is carried out after further adding, as a surfactant, 6.45 g of a 1.0% by weight aqueous solution of polyether modified silicone (side chain-modified terminal OH type) (manufactured by Dow Corning Toray Co., Ltd.) (polymerization peak temperature of 108° C.). Meanwhile, internal gas bubbles ratio of the comparative water absorbent resin powder (9) was 6.4% and other physical properties are shown in Table 1.

Comparative Example 10

Surface Crosslinking for Comparative Example 8

The comparative water absorbent resin powder (10) was obtained by performing the same operations as Comparative example 4 for the comparative water absorbent resin powder (8), which has been obtained from Comparative example 8. Various physical properties of the comparative water absorbent resin powder (10) are shown in Table 1.

Comparative Example 11

Surface Crosslinking for Comparative Example 9

The comparative water absorbent resin powder (11) was obtained by performing the same operations as Comparative example 4 for the comparative water absorbent resin powder (9), which has been obtained from Comparative example 9. Various physical properties of the comparative water absorbent resin powder (11) are shown in Table 1.

Comparative Example 12

Use of p-Methoxyphenol at 70 ppm (Production Example 1)

By performing the same gel-crushing, drying, pulverizing, classifying, surface crosslinking, and sizing as Example 1 of the belt-like hydrogel (i) obtained from Production example 9, the comparative water absorbent resin powder (12) was obtained. Meanwhile, the comparative water absorbent resin powder (12) has internal gas bubbles ratio of 1.9% and other physical properties are shown in Table 1.

Example 10

Using Less Amount of Anti-Caking Agent

The water absorbent resin powder (10) was obtained by performing the same operations as Example 5 except that the water-insoluble inorganic microparticles (AEROSIL 200; Nippon Aerosil Company) of Example 5 are reduced to 0.2 parts by weight. Meanwhile, internal gas bubbles ratio of the water absorbent resin powder (10) was 1.9% and the particle size was at almost the same level as Example 1. Other physical properties are shown in Table 1.

Examples 11 to 13

Addition of Anti-Caking Agent

According to dry stirring and mixing of 0.5 parts by weight of the water-insoluble inorganic microparticles (AEROSIL 200; Nippon Aerosil Company) with 100 parts by weight of each of the water absorbent resin powders (2) to (4) obtained from Examples 2 to 4, the water absorbent resin powders (11) to (13) having the surface coated with water-insoluble inorganic microparticles and particle size almost identical to the particle size before the mixing was obtained. Various physical properties of the water absorbent resin powders (11) to (13) are shown in Table 1.

Examples 14 to 16

Addition of Anti-Caking Agent

According to dry stirring and mixing of 0.5 parts by weight of the water-insoluble inorganic microparticles (AEROSIL 200; Nippon Aerosil Company) with 100 parts by weight of each of the water absorbent resin powders (6) to (8) obtained from Examples 6 to 8, the water absorbent resin powders (14) to (16) having the surface coated with water-insoluble inorganic microparticles and particle size almost identical to the particle size before the mixing was obtained. Various physical properties of the water absorbent resin powders (14) to (16) are shown in Table 1.

Example 17

Addition of Polyvalent Metal Cation

An aqueous solution of aluminum sulfate with the same compositional ratio as Comparative example 2 was added to the water absorbent resin powder (9) obtained from Example 9 followed by drying for 1 hour at 60° C. with no wind in the same manner as Comparative example 2. Subsequently, by having the obtained particles pass through a JIS standard sieve with mesh of 850 μm, the water absorbent resin powder (17) having the particle size almost identical to the particle size before the mixing was obtained. According to granulation using an aqueous solution of aluminum sulfate, the amount of fine powder in the water absorbent resin powder (17) was reduced to 0.2% by weight. Meanwhile, internal gas bubbles ratio of the water absorbent resin powder (17) was 0.9% and other physical properties are shown in Table 1.

Example 18

Addition of Reducing Agent 5 parts by weight of 0.1% by weight sodium hydrogen sulfite was mixed by spraying relative to 100 parts by weight of the water absorbent resin powder (9) obtained from Example 9 followed by drying for 1 hour at 60° C. Subsequently, by having the obtained particles pass through a JIS standard sieve with mesh of 850 μm, the water absorbent resin powder (18) was obtained. The water absorbent resin powder (18) is granulated particles granulated by addition of water, and it has a weight average particle diameter (D50) of 360 μm. The amount of fine powder in the water absorbent resin powder (18) was reduced to 0.2% by weight. Meanwhile, internal gas bubbles ratio of the water absorbent resin powder (18) was 0.9% and other physical properties are shown in Table 1.

Example 19

Further Addition of Chelating Agent 5 parts by weight of a 0.1% by weight aqueous solution of diethylenetriamine pentaacetic acid was mixed by spraying relative to 100 parts by weight of the water absorbent resin powder (9) obtained from Example 9 followed by drying for 1 hour at 60° C. Subsequently, by having the obtained particles pass through a JIS standard sieve with mesh of 850 μm, the water absorbent resin powder (19) was obtained. Meanwhile, internal gas bubbles ratio of the water absorbent resin powder (19) was 0.9%, and the particle size was at almost the same level as Example 18. Other physical properties are shown in Table 1.

Examples 20 to 22

Addition of Anti-Caking Agent

According to dry stirring and mixing of 0.5 parts by weight of the water-insoluble inorganic microparticles (AEROSIL 200; Nippon Aerosil Company) with 100 parts by weight of each of the water absorbent resin powders (17) to (19) obtained from Examples 17 to 19, the water absorbent resin powders (20) to (22) having the surface coated with water-insoluble inorganic microparticles and particle size almost identical to the particle size before the mixing were obtained. Various physical properties of the water absorbent resin powders (20) to (22) are shown in Table 1.

Example 23

Addition of Chelating Agent

The water absorbent resin powder (23) was obtained by performing the same operations as Comparative example 6 except that, for the surface crosslinking step of Comparative example 6, sodium triethylenepentamine hexaacetic acid is added at 500 ppm (relative to water absorbent resin) as a chelating agent to the surface crosslinking agent. The water absorbent resin powder (23) is granulated particles granulated by addition of water, and it has a weight average particle diameter (D50) of 360 μm. The amount of fine powder was reduced to 0.2% by weight. Meanwhile, other physical properties are shown in Table 1.

Example 24

Addition of Reducing Agent

The water absorbent resin powder (24) was obtained by performing the same operations as Comparative example 6 except that 1% by weight of sodium hydrogen sulfite (relative to water absorbent resin) as an inorganic reducing agent is added after the surface crosslinking to the comparative water absorbent resin powder (6) obtained from Comparative example 6. Meanwhile, the particle size of the water absorbent resin powder (24) was at almost the same level as Example 24. Other physical properties are shown in Table 1.

TABLE 1

| | | CRC [g/g] | $AAP_{0.7}$ [g/g] | $AAP_{0.3}$ [g/g] | Ext [wt %] | Chelating agent [wt %] | Degradable soluble component [wt %] |
|---|---|---|---|---|---|---|---|
| Comp. example 1 | Comp. water absorbent resin powder (1) | 37.8 | 7.8 | 9.8 | 8 | 0 | 42 |
| Comp. example 2 | Comp. water absorbent resin powder (2) | 27.6 | 20.1 | 27.3 | 8 | 0 | 48 |
| Comp. example 3 | Comp. water absorbent resin powder (3) | 34.0 | 8.1 | 10.5 | 7 | 0.022 | 13 |
| Comp. example 4 | Comp. water absorbent resin powder (4) | 26.6 | 24.6 | 26.1 | 7 | 0.022 | 17 |
| Comp. example 5 | Comp. water absorbent resin powder (5) | 32.4 | 24.1 | 32.0 | 14 | 0.022 | 23 |
| Example 1 | Water absorbent resin powder (1) | 32.3 | 24.2 | 32.1 | 14 | 0.022 | 23 |
| Example 2 | Water absorbent resin powder (2) | 32.5 | 24.3 | 31.8 | 14 | 0.022 | 23 |
| Example 3 | Water absorbent resin powder (3) | 32.4 | 24.2 | 31.9 | 14 | 0.022 | 23 |
| Example 4 | Water absorbent resin powder (4) | 32.4 | 24.1 | 31.9 | 14 | 0.022 | 23 |
| Example 5 | Water absorbent resin powder (5) | 32.3 | 20.9 | 27.8 | 14 | 0.022 | 23 |
| Comp. example 6 | Comp. water absorbent resin powder (6) | 32.1 | 24.1 | 31.9 | 14 | 0 | 60 |
| Comp. example 7 | Comp. water absorbent resin powder (7) | 32.1 | 24.1 | 32.1 | 14 | 0.022 | 24 |
| Example 6 | Water absorbent resin powder (6) | 32.3 | 24.2 | 32.1 | 14 | 0.022 | 23 |
| Example 7 | Water absorbent resin powder (7) | 35.1 | 24.1 | 34.5 | 16 | 0.022 | 17 |
| Example 8 | Water absorbent resin powder (8) | 36.0 | 25.0 | 35.0 | 23 | 0.022 | 24 |
| Example 9 | Water absorbent resin powder (9) | 40.0 | 17.0 | 34.0 | 30 | 0.022 | 31 |
| Comp. example 8 | Comp. water absorbent resin powder (8) | 35.2 | 9.0 | 10.5 | 7 | 0.022 | 13 |
| Comp. example 9 | Comp. water absorbent resin powder (9) | 34.0 | 9.0 | 10.6 | 7 | 0.022 | 13 |
| Comp. example 10 | Comp. water absorbent resin powder (10) | 27.1 | 24.6 | 26.9 | 7 | 0.022 | 13 |
| Comp. example 11 | Comp. water absorbent resin powder (11) | 27.2 | 24.4 | 27.2 | 7 | 0.022 | 13 |
| Comp. example 12 | Comp. water absorbent resin powder (12) | 27.2 | 23.6 | 27.1 | 7 | 0.022 | 13 |
| Example 10 | Water absorbent resin powder (10) | 32.5 | 24.1 | 30.0 | 14 | 0.022 | 23 |
| Example 11 | Water absorbent resin powder (11) | 32.4 | 22.2 | 28.5 | 14 | 0.022 | 23 |
| Example 12 | Water absorbent resin powder (12) | 32.4 | 22.2 | 28.4 | 14 | 0.022 | 23 |
| Example 13 | Water absorbent resin powder (13) | 32.3 | 22.0 | 28.3 | 14 | 0.022 | 23 |
| Example 14 | Water absorbent resin powder (14) | 32.1 | 21.9 | 28.3 | 14 | 0.022 | 23 |
| Example 15 | Water absorbent resin powder (15) | 36.0 | 16.0 | 28.0 | 23 | 0.022 | 24 |
| Example 16 | Water absorbent resin powder (16) | 40.0 | 10.0 | 25.0 | 30 | 0.022 | 31 |
| Example 17 | Water absorbent resin powder (17) | 40.0 | 16.0 | 32.1 | 30 | 0.022 | 33 |
| Example 18 | Water absorbent resin powder (18) | 39.0 | 17.0 | 34.0 | 30 | 0.022 | 31 |
| Example 19 | Water absorbent resin powder (19) | 40.0 | 17.0 | 34.0 | 30 | 0.027 | 28 |
| Example 20 | Water absorbent resin powder (20) | 40.0 | 10.0 | 25.0 | 30 | 0.022 | 33 |
| Example 21 | Water absorbent resin powder (21) | 39.0 | 9.3 | 24.1 | 29 | 0.022 | 31 |
| Example 22 | Water absorbent resin powder (22) | 40.0 | 10.0 | 25.0 | 30 | 0.022 | 28 |
| Example 23 | Water absorbent resin powder (23) | 32.1 | 24.1 | 31.9 | 14 | 0.050 | 20 |
| Example 24 | Water absorbent resin powder (24) | 30.8 | 22.8 | 30.7 | 29 | 0 | 21 |

| | | FSR [g/g/s] | Inorganic microparticles or Inorganic cross-linking agent [wt %] | Blocking ratio against moisture absorption [%] | MQ (in SAP) [ppm] | internal gas bubbles ratio [%] |
|---|---|---|---|---|---|---|
| Comp. example 1 | Comp. water absorbent resin powder (1) | 0.48 | 0 | 100 | 0 | 6.8 |
| Comp. example 2 | Comp. water absorbent resin powder (2) | 0.50 | 0 | 100 | 0 | 6.8 |
| Comp. example 3 | Comp. water absorbent resin powder (3) | 0.27 | 0 | 100 | 0 | 2.6 |
| Comp. example 4 | Comp. water absorbent resin powder (4) | 0.26 | 0 | 100 | 0 | 2.6 |

TABLE 1-continued

| | | | | | | |
|---|---|---|---|---|---|---|
| Comp. example 5 | Comp. water absorbent resin powder (5) | 0.29 | 0 | 100 | 12 | 2.6 |
| Example 1 | Water absorbent resin powder (1) | 0.36 | 0 | 100 | 12 | 1.9 |
| Example 2 | Water absorbent resin powder (2) | 0.37 | 0 | 100 | 12 | 1.1 |
| Example 3 | Water absorbent resin powder (3) | 0.38 | 0 | 100 | 12 | 0.8 |
| Example 4 | Water absorbent resin powder (4) | 0.32 | 0 | 100 | 12 | 2.3 |
| Example 5 | Water absorbent resin powder (5) | 0.38 | 0.5 | 0 | 12 | 1.9 |
| Comp. example 6 | Comp. water absorbent resin powder (6) | 0.36 | 0 | 100 | 12 | 1.9 |
| Comp. example 7 | Comp. water absorbent resin powder (7) | 0.36 | 0 | 100 | 0 | 1.9 |
| Example 6 | Water absorbent resin powder (6) | 0.36 | 0 | 100 | 55 | 1.9 |
| Example 7 | Water absorbent resin powder (7) | 0.34 | 0 | 100 | 12 | 1.6 |
| Example 8 | Water absorbent resin powder (8) | 0.35 | 0 | 100 | 12 | 0.8 |
| Example 9 | Water absorbent resin powder (9) | 0.36 | 0 | 100 | 12 | 0.9 |
| Comp. example 8 | Comp. water absorbent resin powder (8) | 0.38 | 0 | 100 | 12 | 3.9 |
| Comp. example 9 | Comp. water absorbent resin powder (9) | 0.45 | 0 | 100 | 12 | 6.4 |
| Comp. example 10 | Comp. water absorbent resin powder (10) | 0.39 | 0 | 100 | 12 | 3.9 |
| Comp. example 11 | Comp. water absorbent resin powder (11) | 0.39 | 0 | 100 | 12 | 6.4 |
| Comp. example 12 | Comp. water absorbent resin powder (12) | 0.36 | 0 | 100 | 12 | 1.9 |
| Example 10 | Water absorbent resin powder (10) | 0.38 | 0.2 | 30 | 12 | 1.9 |
| Example 11 | Water absorbent resin powder (11) | 0.39 | 0.5 | 0 | 12 | 1.1 |
| Example 12 | Water absorbent resin powder (12) | 0.39 | 0.5 | 0 | 12 | 0.8 |
| Example 13 | Water absorbent resin powder (13) | 0.34 | 0.5 | 0 | 12 | 2.3 |
| Example 14 | Water absorbent resin powder (14) | 0.38 | 0.5 | 0 | 12 | 1.9 |
| Example 15 | Water absorbent resin powder (15) | 0.37 | 0.5 | 0 | 12 | 0.8 |
| Example 16 | Water absorbent resin powder (16) | 0.38 | 0.5 | 0 | 12 | 0.9 |
| Example 17 | Water absorbent resin powder (17) | 0.36 | (Sulfuric acid AL) | 90 | 12 | 0.9 |
| Example 18 | Water absorbent resin powder (18) | 0.36 | 0 | 100 | 12 | 0.9 |
| Example 19 | Water absorbent resin powder (19) | 0.36 | 0 | 100 | 12 | 0.9 |
| Example 20 | Water absorbent resin powder (20) | 0.38 | 0.5 | 0 | 12 | 0.9 |
| Example 21 | Water absorbent resin powder (21) | 0.38 | 0.5 | 0 | 12 | 0.9 |
| Example 22 | Water absorbent resin powder (22) | 0.38 | 0.5 | 0 | 12 | 0.9 |
| Example 23 | Water absorbent resin powder (23) | 0.36 | 0 | 100 | 12 | 1.9 |
| Example 24 | Water absorbent resin powder (24) | 0.36 | 0 | 100 | 12 | 1.9 |

Note)
Weather resistance (soluble component after deterioration test) of Comp. example 7 (without MQ) was 10% higher than Example 1 (MQ = 12 ppm/SAP)

Note)
Moisture content of water absorbent resin was 1 [% by weight] (with the proviso that, Examples 18, 19, 21, and 24 have water added at 5% so that moisture content is about 5% and CRC/AAP is also lowered. Particles are granulated in water)

Note)
SFC of Examples 11 to 14 is 14 [$\times 10^{-7} \cdot s \cdot cm^3 \cdot g^{-1}$]

Note)
Residual monomers of Examples 18, 21, and 24 that are added with sulfite salt are 190 ppm (Summary)

As shown in Table 1, it was found that, by performing the polymerization in the presence of p-methoxyphenol (in particular, continuous belt polymerization), adding a cheating agent or an inorganic reducing agent either during or after the polymerization, and by performing gel-crushing with specific gel grinding energy, a novel water absorbent resin powder having low internal gas bubbles ratio and containing a specific amount of p-methoxyphenol, in which the degradable soluble component is controlled to low level, can be provided. It was also found that, by mixing water-insoluble inorganic microparticles on a surface of the water absorbent resin powder, a novel water absorbent resin powder containing a specific amount of p-methoxyphenol which exhibits an excellent anti-caking property and low internal gas bubbles ratio can be provided.

Compared to other Examples (except Example 6 in which p-methoxyphenol is used in an increased amount and Example 29 in which Fe is used in an increased amount are excluded) in which residual monomers are 290 to 310 ppm, it was found that the residual monomers are reduced to about 190 ppm in Examples 18, 21, and 24, to which a reducing agent (sulfite hydrogen salt) and 5% by weight of water are added.

It was also found that Examples of the present invention have bulk specific gravity of about 0.6 [$g/cm^3$], which is higher than Comparative examples 1 and 2, indicating a compact state. Further, the surface tension is as high as 71 [N/m] and the reversion amount of paper diaper described below (Re-Wet) is small.

Example 25

Impact Resistance Test

The aforementioned anti-damaging property test was performed for the water absorbent resin powders (1) to (3) and the comparative water absorbent resin powders (2), (4), and (5), which have been obtained from Examples 1 to 3 and Comparative examples 2, 4, and 5, respectively, to cause a damage on each of the water absorbent resin powders.

AAP 0.7 and amount of fine powder were measured for the water absorbent resin powder given with the damage, and the reduced AAP amount and increase amount of fine powder were obtained. The results are shown in Table 2.

TABLE 2

| | | $AAP_{0.7}$ [g/g] | internal gas bubbles ratio [%] | Reduced AAP amount after anti-damaging property test [g/g] | Increase ratio of fine powder after anti-damaging property test [wt %] |
|---|---|---|---|---|---|
| Comp. example 2 | Comp. water absorbent resin powder (2) | 20.1 | 6.8 | −3.1 | +7.1 |
| Comp. example 4 | Comp. water absorbent resin powder (4) | 24.6 | 2.6 | −1.0 | +1.1 |
| Comp. example 5 | Comp. water absorbent resin powder (5) | 24.1 | 2.6 | −0.9 | +1.1 |
| Example 1 | Water absorbent resin powder (1) | 24.2 | 1.8 | −0.5 | +0.7 |
| Example 2 | Water absorbent resin powder (2) | 24.3 | 1.1 | −0.4 | +0.6 |
| Example 3 | Water absorbent resin powder (3) | 24.2 | 0.8 | −0.3 | +0.5 |

(Summary)

As shown in Table 2, as having little decrease in physical properties (AAP and fine powder) and internal gas bubbles ratio controlled at low level, the water absorbent resin powder according to the present invention has improved impact resistance. Such water absorbent resin powder shows little decrease in physical properties that are caused by damage during air transport or production of paper diaper, and it maintains high physical properties after production of a paper diaper, in particular, high concentration paper diaper. When water-insoluble inorganic microparticles are used, in particular, not only an anti-caking property is enhanced but also an absolute absorption amount of a paper diaper is enhanced even when CRC (water absorption capacity without load) is at the same level or so (see, Table 4 given below).

Example 26

Accelerated Weather Resistance Test

By performing an accelerated weather resistance test for the water absorbent resin powders (1) and (6) and the comparative water absorbent resin powder (7), which have been obtained from Examples and 6 and Comparative example 7, respectively, deterioration ratio (weather resistance) was obtained. Results of measuring the initial color hue are also shown in Table 3.

(Summary)

As shown in Table 3, it is found that, by containing a specific amount of p-methoxyphenol, weather resistance of the water absorbent resin powder according to the present invention is enhanced (i.e., amount of soluble components is lowered). However, when the amount of p-methoxyphenol is the same or higher than a pre-determined amount (50 ppm), the initial color hue (YI value) or residual monomers are adversely affected.

Example 27

Evaluation of Paper Diaper

By using each of the water absorbent resin powders (1), (5), (15) to (17) and the comparative water absorbent resin powders (6), (10), and (11) obtained from Examples 1, 5, 15 to 17 and Comparative examples 6, 10, and 11, respectively, an absorbent article, a mini absorbent body, and a paper diaper type absorbent body were produced.

For the absorbent article, mini absorbent body, and paper diaper type absorbent body, an absorption amount of the absorbent article, an absolute absorption amount of the mini absorbent body, an absolute absorption amount of the paper diaper type absorbent body, and a reversion amount of the paper diaper type absorbent body were measured. The results are shown in Table 4.

TABLE 3

| | | CRC [g/g] | $AAP_{0.7}$ [g/g] | $AAP_{0.3}$ [g/g] | MQ [ppm] | Weather resistance [wt %] | Initial color hue [YI] | Residual monomers [ppm] |
|---|---|---|---|---|---|---|---|---|
| Example 1 | Water absorbent resin powder (1) | 32.3 | 24.2 | 32.1 | 12 | 32.4 | 9.1 | 290 |
| Comp. example 7 | Comp. water absorbent resin powder (7) | 32.1 | 24.1 | 32.1 | ND | 40.1 | 3.1 | 270 |
| Example 6 | Water absorbent resin powder (6) | 32.3 | 24.2 | 32.1 | 55 | 28.5 | 20.1 | 400 |

TABLE 4

| | | CRC [g/g] | AAP$_{0.7}$ [g/g] | AAP$_{0.3}$ [g/g] | Degradable soluble component [wt %] | Absorption amount of absorbent article [g] | Absolute absorption amount of mini absorbent body [g] | Absolute absorption amount of disposable diaper-type absorbent body [g] | Reversion amount of disposable diaper-type absorbent body [g] |
|---|---|---|---|---|---|---|---|---|---|
| Example 1 | Water absorbent resin powder (1) | 32.3 | 24.2 | 32.1 | 23 | 275 | 280 | 680 | 10 |
| Example 5 | Water absorbent resin powder (5) | 32.3 | 20.9 | 27.8 | 23 | 275 | 310 | 772 | 12 |
| Example 15 | Water absorbent resin powder (15) | 36.0 | 16.0 | 28.0 | 24 | 288 | 360 | 820 | 12 |
| Example 16 | Water absorbent resin powder (16) | 40.0 | 10.0 | 25.0 | 31 | 288 | 400 | 860 | 12 |
| Example 17 | Water absorbent resin powder (17) | 40.0 | 16.0 | 32.1 | 33 | 288 | 390 | 845 | 11 |
| Comp. example 1 | Comp. water absorbent resin powder (1) | 37.8 | 7.8 | 9.8 | 42 | 200 | 300 | 740 | 25 |
| Comp. example 2 | Comp. water absorbent resin powder (2) | 27.6 | 20.1 | 27.3 | 48 | 250 | 260 | 600 | 22 |
| Comp. example 6 | Comp. water absorbent resin powder (6) | 32.1 | 24.1 | 31.9 | 60 | 250 | 280 | 664 | 13 |
| Comp. example 10 | Comp. water absorbent resin powder (10) | 27.1 | 24.6 | 26.9 | 13 | 250 | 260 | 605 | 20 |
| Comp. example 11 | Comp. water absorbent resin powder (11) | 27.2 | 24.4 | 27.2 | 13 | 250 | 260 | 610 | 19 |

(Summary)

As shown in Table 4, by controlling the degradable soluble component to low level, it is found that, the absorption amount, absolute absorption amount are increased (enhanced) and the reversion amount (Re-Wet) is lowered in an absorbent article or an absorbent body.

Example 28

Fe Amount in an Aqueous Solution of Sodium Hydroxide

The water absorbent resin powder (28) was obtained by performing the same operations as Example 8 except that Fe amount in an aqueous solution of sodium hydroxide of Example 8 is changed to 5 ppb. Meanwhile, the Fe amount (in terms of Fe ion) in an aqueous solution of sodium hydroxide that is used in Examples 1 to 24 is 1 ppm, and the water absorbent resin powders (1) to (24) obtained from the corresponding Example contain Fe in an amount of about 0.3 ppm originating from sodium hydroxide as raw material.

Results of the initial color hue, color hue with the lapse of time, degradable soluble component that are measured for the water absorbent resin powder (28) are shown in Table 5.

Example 29

Fe Amount in an Aqueous Solution of Sodium Hydroxide

The water absorbent resin powder (29) was obtained by performing the same operations as Example 8 except that Fe amount in an aqueous solution of sodium hydroxide of Example 8 is changed to 14 ppm. Results of the initial color hue, color hue with the lapse of time, degradable soluble component that are measured for the water absorbent resin powder (29) are shown in Table 5.

TABLE 5

| | | Fe amount in NaOH [ppm] | Initial coloration [YI] | Coloration with lapse of time [YI] | Degradable soluble component [wt %] | Residual monomers [ppm] |
|---|---|---|---|---|---|---|
| Example 8 | Water absorbent resin powder (8) | 1 | 8.3 | 42 | 24 | 290 |
| Example 28 | Water absorbent resin powder (28) | 0.005 | 8.2 | 20 | 19 | 270 |
| Example 29 | Water absorbent resin powder (29) | 14 | 9.8 | 47 | 31 | 420 |

(Summary)

As shown in Table 5, controlling the Fe amount is important from the viewpoint of residual monomers, and color hue and deterioration of the water absorbent resin powder. Further, as shown in Table 1, from the comparison with Comparative example 6 (no chelating agent), it was found that the deterioration is suppressed by use of a chelating agent even when Fe is present at 0.3 ppm. Meanwhile, since excessive purification may yield slower polymerization speed, and thus the acceptable lower limit is 0.1 ppm or so from the viewpoint of cost related to purification or polymerization speed.

Example 30

In the above Examples 18, 19, 21, and 24, the water absorbent resin powder was added with 5% by weight of water and a chelating agent (or reducing agent). As a result, the water absorbent resin powder (18), (19), (21), and (24) obtained by using water as a binder was confirmed to have granulation (i.e., average particle diameter is increased by 20 to 30 μm) and reduced fine powder (0.1 to 0.3%). According to addition of a chelating agent or a reducing agent, granulated particles with controlled internal gas bubbles ratio and moisture content are obtained.

INDUSTRIAL APPLICABILITY

The water absorbent resin powder produced by the production method of the present invention is useful for a hygiene product such as paper diaper, feminine napkin, or anti-anemic agent for medical use.

EXPLANATION OF SYMBOLS

11 Casing
12 Base
13 Screw
14 Feed inlet
15 Hopper
16 Extrusion outlet
17 Porous die
18 Rotating blade
19 Ring
20 Backflow preventing member
20a Belt-like protrusions (backflow preventing member)
21 Motor
22 Linear protrusions

The invention claimed is:

1. A polyacrylic acid (salt)-based water absorbent resin powder in which the water absorption capacity without load (CRC) is 30 to 45 [g/g], the water absorption capacity under load (AAP 0.3) is 20 to 35 [g/g], the water absorption capacity under load (AAP 0.7) is 10 to 28 [g/g], and the weight average particle diameter (D50) is 300 to 500 μm, wherein the water absorbent resin powder comprises p-methoxyphenol, has a degradable soluble component (0.05% L-A (saline) for 2 hours/60° C., one hour extraction rinse/room temperature) of 40% by weight or less, and an internal gas bubbles ratio of 0.1 to 2.5%, as specified by the following equation (Internal gas bubbles ratio)[%]={(True density)−(Apparent density)}/(True density)×100.

2. The water absorbent resin powder according to claim 1, further comprising water-insoluble inorganic microparticles, a water soluble polyvalent metal salt (with the proviso that, iron salt is excluded), an inorganic or organic reducing agent, or a combination thereof.

3. The water absorbent resin powder according to claim 1, further comprising a metal chelating agent.

4. The water absorbent resin powder according to claim 1, wherein content of an iron ion is 0.1 to 3 ppm.

5. The water absorbent resin powder according to claim 1, wherein content of p-methoxyphenol is 5 to 50 ppm.

6. The water absorbent resin powder according to claim 1, wherein residual monomers are 500 ppm or less.

7. The water absorbent resin powder according to claim 1, wherein the degradable soluble component (0.05% L-A (saline) for 2 hours/60° C., one hour extraction rinse/room temperature) is 20% by weight or less.

8. The water absorbent resin powder according to claim 1, wherein powder flowability after moisture absorption test is 70% by weight or more.

9. The water absorbent resin powder according to claim 3, wherein the metal chelating agent is comprised at 0.001 to 2% by weight relative to the water absorbent resin powder.

10. The water absorbent resin powder according to claim 1, wherein an increase amount of degradable soluble component (defined as degradable soluble component (%)−16 hour soluble component (%)) is 20% by weight or less.

11. The water absorbent resin powder according to claim 3, wherein the chelating agent is a water soluble non-polymeric chelating agent selected from amino polyvalent carboxylic acid and amino polyvalent phosphoric acid.

12. A method for producing a water absorbent resin powder which has internal gas bubbles ratio of 0.1 to 2.5% as specified by the following equation, the method comprising:
a polymerization step wherein performing foaming polymerization or boiling polymerization of an aqueous monomer solution containing p-methoxyphenol and also acrylic acid as a main component;
a gel-crushing step wherein kneading and grain refining a water-containing gel-like polymer having gas bubbles obtained from the polymerization;
a drying step wherein heating and drying it at 150 to 250° C. after gel-crushing,
a pulverizing and classification step wherein pulverizing and classifying a dried product to have a weight average particle diameter of 300 to 500 μm; and
surface crosslinking the pulverized and classified product with internal gas bubbles ratio 0.1 to 2.5% to have the water absorption capacity without load (CRC) of 30 to 45 [g/g], the water absorption capacity under load (AAP 0.3) of 20 to 35 [g/g], and the water absorption capacity under load (AAP 0.7) of 10 to 28 [g/g]

(Internal gas bubbles ratio)[%]={(True density)−(Apparent density)}/(True density)×100.

13. A method for producing a water absorbent resin powder which has internal gas bubbles ratio of 0.1 to 2.5% as specified by the following equation, the method comprising steps of:
performing foaming polymerization or boiling polymerization of an aqueous monomer solution containing p-methoxyphenol and also acrylic acid as a main component;
adding a chelating agent during the polymerization or after the polymerization step; and
surface crosslinking a water absorbent resin containing p-methoxyphenol and having internal gas bubbles ratio of 0.1 to 2.5% to have the water absorption capacity without load (CRC) of 30 to 45 [g/g], the water absorption capacity under load (AAP 0.3) of 20 to 35 [g/g] and the water absorption capacity under load (AAP 0.7) of 10 to 28 [g/g]

(Internal gas bubbles ratio)[%]={(True density)−(Apparent density)}/(True density)×100.

14. The method according to claim 12, wherein, for the gel-crushing step, the water-containing gel-like crosslinked polymer with resin solid content of 10 to 80% by weight is subjected to gel-crushing which satisfies at least one of the following (1) to (4):
(1) the gel-crushing is carried out with gel grinding energy (GGE) of 18 to 60 [J/g];
(2) the gel-crushing is carried out with gel grinding energy (2) (GGE (2)) of 9 to 40 [J/g];
(3) the weight average molecular weight of water soluble component of the water-containing gel-like crosslinked polymer is increased by 10,000 to 500,000 [Da]; and
(4) the gel-crushing is carried out until the water-containing gel-like crosslinked polymer has a weight average particle diameter (D50) of 350 to 2,000 μm, and logarithmic standard deviation (σζ) of particle size distribution of 0.2 to 1.0.

15. The method according to claim 12, wherein water-insoluble inorganic microparticles, a water soluble polyvalent metal salt (with the proviso that, iron salt is excluded), an inorganic or organic reducing agent, or a combination thereof are additionally mixed after the drying step.

16. The method according to claim 12, wherein a metal chelating agent is additionally mixed after the polymerization step.

17. The method according to claim 12, wherein content of iron ion in monomer is 0.1 to 3 ppm.

18. The method according to claim 12, wherein content of p-methoxyphenol in monomer is 5 to 200 ppm (relative to monomer solid content).

19. The method according to claim 12, further comprising a step of neutralizing whole or part of acrylic acid with a base having a Fe content of 0 to 7 ppm before the polymerization step, wherein the polymerization step is a step of performing, under condition including maximum temperature of 130° C. or less and polymerization time of between 0.5 minutes to 3 hours, aqueous solution polymerization or reverse-phase suspension polymerization of an aqueous monomer solution with monomer concentration of 30 to 55% by weight, in which acrylic acid (salt) is contained at 90 to 100% by mol in the monomer, by using 0.001 to 1% by mol of a polymerization initiator (relative to the monomer), the drying step is a step of drying the water-containing gel-like crosslinked polymer, which has been obtained in particle form by polymerization, to have a moisture content of 20% by weight or less with drying temperature of 100 to 250° C. and drying time of 10 to 120 minutes, and the surface crosslinking is a step of mixing 0.001 to 10 parts by weight of a surface crosslinking agent relative to 100 parts by weight of the water absorbent resin powder after completion of the pulverizing and classification step and performing a heating treatment for 1 minute to 2 hours at 70 to 300° C.

20. An absorbent article comprising the water absorbent resin powder defined claim 1, wherein core concentration as defined by weight ratio of the water absorbent resin relative to total weight of the water absorbent resin and a hydrophilic fiber material is 30 to 100% by weight.

* * * * *